(12) United States Patent
Schechterman et al.

(10) Patent No.: US 8,212,858 B2
(45) Date of Patent: *Jul. 3, 2012

(54) OPTICAL DEVICE

(75) Inventors: Mark Schechterman, Nes-Ziona (IL); Michael Goldstein, Herzelia Pituach (IL); Nadav Horesh, Petah Tikva (IL); Avi Yaron, Givat Shmuel (IL); Martin Abraham, Hod Hasharon (IL)

(73) Assignee: Visionsense Ltd., Petah Tikva (IL)

( * ) Notice: Subject to any disclaimer, the term of this patent is extended or adjusted under 35 U.S.C. 154(b) by 1279 days.

This patent is subject to a terminal disclaimer.

(21) Appl. No.: 11/932,417

(22) Filed: Oct. 31, 2007

(65) Prior Publication Data

US 2008/0055400 A1    Mar. 6, 2008

Related U.S. Application Data

(60) Division of application No. 10/145,418, filed on May 13, 2002, now Pat. No. 7,683,926, which is a continuation-in-part of application No. 09/785,791, filed on Feb. 16, 2001, and a continuation-in-part of application No. 09/785,512, filed on Feb. 16, 2001, now Pat. No. 7,116,352, which is a continuation-in-part of application No. 09/699,624, filed on Oct. 30, 2000, now Pat. No. 7,154,527, which is a continuation-in-part of application No. 09/257,850, filed on Feb. 25, 1999, now Pat. No. 6,396,873.

(51) Int. Cl.
    *H04N 13/00* (2006.01)

(52) U.S. Cl. ............... 348/42; 348/45; 348/51; 348/49; 348/59; 348/46; 348/65; 348/77; 355/22

(58) Field of Classification Search ................ 348/42, 348/45, 51, 49, 59, 46, 65, 77; 355/22
    See application file for complete search history.

(56) References Cited

U.S. PATENT DOCUMENTS

| 2,639,653 | A | 5/1953 | Fischer |
| 3,932,699 | A | 1/1976 | Tripp |
| 4,414,470 | A | 11/1983 | Nakaoka |
| 4,437,764 | A | 3/1984 | Levine et al. |
| 4,873,572 | A | 10/1989 | Miyazaki et al. |

(Continued)

FOREIGN PATENT DOCUMENTS

CA    2157073    6/1996

(Continued)

OTHER PUBLICATIONS

Handbook of Optics, vol. 2, McGraw-Hill Inc., 1995, pp. 15-24 by Norman Greenberg.

*Primary Examiner* — Shawn An
(74) *Attorney, Agent, or Firm* — Merchant & Gould P.C.

(57) ABSTRACT

Stereoscopic device including an image directing assembly, an image differentiator and an image detector, the image directing assembly having a first light inlet for receiving a first image and a second light inlet for receiving a second image, the first light inlet being spaced apart from the second light inlet, the image differentiator differentiating between the first image and the second image, wherein the image directing assembly directs the first image to the image detector via a common path, and wherein the image directing assembly directs the second image to the image detector via the common path.

24 Claims, 55 Drawing Sheets

U.S. PATENT DOCUMENTS

| | | | |
|---|---|---|---|
| 4,945,407 A | | 7/1990 | Winnek |
| 4,959,641 A | | 9/1990 | Bass et al. |
| 5,034,805 A | | 7/1991 | Ishizaka |
| 5,076,687 A | * | 12/1991 | Adelson ..................... 356/4.04 |
| 5,121,452 A | | 6/1992 | Stowe et al. |
| 5,192,969 A | * | 3/1993 | Igarashi et al. ................. 355/22 |
| 5,233,416 A | | 8/1993 | Inoue |
| 5,428,386 A | | 6/1995 | D'Alfonso et al. |
| 5,490,015 A | | 2/1996 | Umeyama |
| 5,527,263 A | | 6/1996 | Zobel et al. |
| 5,552,840 A | | 9/1996 | Ishii et al. |
| 5,588,948 A | * | 12/1996 | Takahashi et al. ............ 600/111 |
| 5,594,497 A | | 1/1997 | Ahem et al. |
| 5,603,687 A | | 2/1997 | Hori et al. |
| 5,604,531 A | | 2/1997 | Iddan et al. |
| 5,606,436 A | | 2/1997 | Shapiro |
| 5,606,455 A | | 2/1997 | Eichenlaub |
| 5,613,936 A | | 3/1997 | Czarnek et al. |
| 5,653,677 A | | 8/1997 | Okada |
| 5,743,846 A | | 4/1998 | Takahashi et al. |
| 5,743,847 A | | 4/1998 | Nakamura et al. |
| 5,751,341 A | | 5/1998 | Chaleki et al. |
| 5,760,827 A | | 6/1998 | Faris |
| 5,776,049 A | | 7/1998 | Takahashi |
| 5,800,341 A | | 9/1998 | McKenna |
| 5,812,187 A | * | 9/1998 | Watanabe ....................... 348/70 |
| 5,825,534 A | | 10/1998 | Strahle |
| 5,828,487 A | | 10/1998 | Greening et al. |
| 5,835,194 A | | 11/1998 | Morton |
| 5,865,829 A | | 2/1999 | Kitajima |
| 5,868,664 A | | 2/1999 | Speier et al. |
| 5,966,168 A | | 10/1999 | Miyazaki |
| 5,991,074 A | | 11/1999 | Nose et al. |
| 6,075,555 A | | 6/2000 | Street |
| 6,306,082 B1 | | 10/2001 | Takahashi et al. |
| 6,593,957 B1 | | 7/2003 | Christie |
| 7,683,926 B2 | * | 3/2010 | Schechterman et al. ........ 348/42 |

FOREIGN PATENT DOCUMENTS

| | | |
|---|---|---|
| WO | WO 00/22975 | 4/2000 |

* cited by examiner

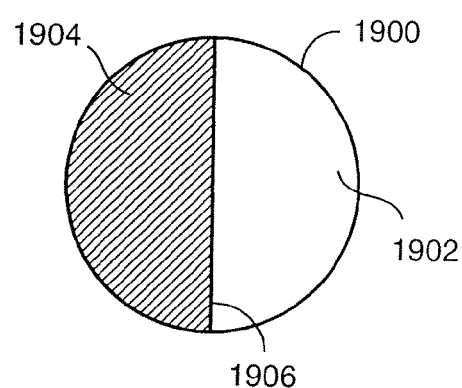
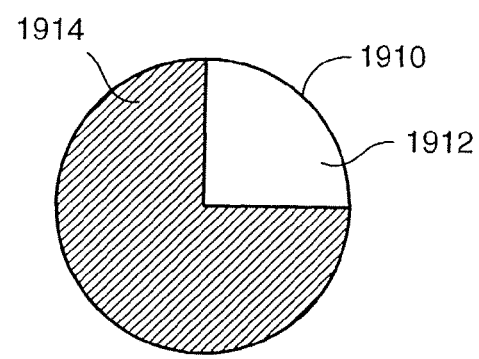
FIG. 39A  FIG. 39B
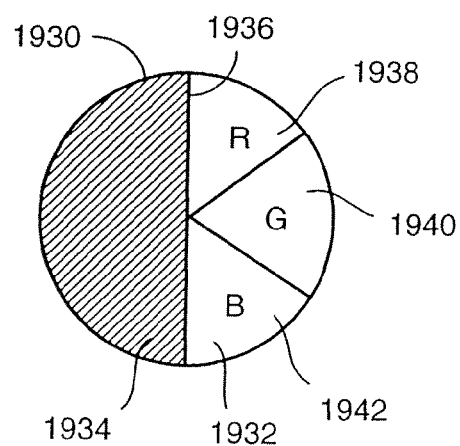
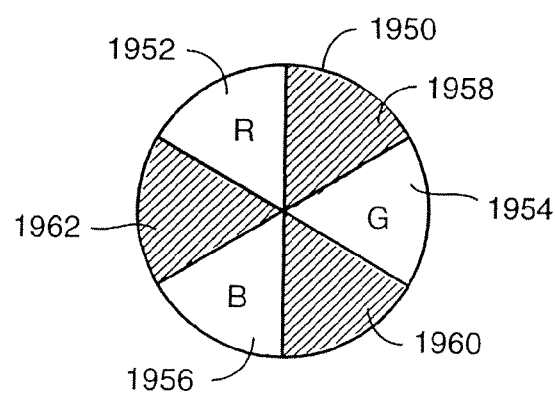
FIG. 40A  FIG. 40B

OPTICAL DEVICE

This application is a divisional of Ser. No. 10/145,418, filed May 13, 2002, which is a continuation-in-part of application Ser. No. 09/785,791, filed on Feb. 16, 2001 and Ser. No. 09/785,512, filed on Feb. 16, 2001, which are continuation-in-parts of application Ser. No. 09/699,624, filed on Oct. 30, 2001, which is a continuation-in-part of application Ser. No. 09/257,850, filed on Feb. 25, 1999 and which application(s) are incorporated herein by reference.

FIELD OF THE DISCLOSED TECHNIQUE

The disclosed technique relates to endoscopes, microscopes and boroscopes, in general and to stereoscopic image pick up devices with color imaging capability, in particular.

BACKGROUND OF THE DISCLOSED TECHNIQUE

Stereoscopic image detection devices are known in the art. Such devices are required to obtain and provide a combination of small cross section and high image quality. It will be appreciated by those skilled in the art that high image quality, in general, is characterized by stereoscopic vision accuracy, color capabilities, high resolution and illumination requirements.

It is noted that conventional methods, which provide stereoscopic images, require a wider optical path than a monocular one. Such a widened optical path enlarges the cross-section required for the detection device considerably. Hence, the requirement for a small cross section is not maintained.

U.S. Pat. No. 5,527,263 to Zobel, et al., is directed to a dual optical path stereo endoscope with simple optical adjustment. U.S. Pat. No. 5,776,049 to Takahashi, is directed to a "Stereo Endoscope and Stereo Endoscope Imaging Apparatus" and provides a device which utilizes a combination of two optical paths with two charge coupled devices (CCD's), capable of variable zoom.

Auto-stereoscopic devices, which utilize one optical system to provide a stereo effect, are also known in the art. Such a device is provided in U.S. Pat. No. 5,603,687 to Hori et al., which is directed to a device with two parallel optical axes and two CCD units. Hori selected an asymmetrical approach, wherein one optical channel has a large aperture for light and details, and the other optical channel provides a parallax image for stereoscopic imagery to the proximal CCD.

U.S. Pat. No. 5,613,936 to Czarnek et al., is directed to a stereoscopic endoscope device which utilizes light polarization and time multiplexing, in order to transmit each different polarized image corresponding to left and right images multiplexed in time, through one optical channel that transfers images from the lateral side of the endoscope shaft. This endoscope has to be inserted deeper into the human cavity to receive a stereo image. It must also be used with a head mounted display device called "switched shutter glasses" that causes eye irritation. It is noted that according to Czarnek each image is received in 25% of the original quality. As much as 50% of the light received from the object, is lost due to polarization considerations and as much as 50% of the remaining information is lost due to channel switching.

U.S. Pat. No. 5,588,948, to Takahashi, et al., is directed to a stereoscopic endoscope. The stereo effect is produced by having a dividing pupil shutter, which splits the optical path onto the left and right sides, and the up and down sides. These sides are alternately projected on a proximal image pick up device, using time multiplexing. According to another aspect of this reference, a distal CCD is included, which is divided to left and right sides with a shading member separating them, for achieving space multiplexing.

U.S. Pat. No. 5,743,847 to Nakamura et al., is directed to a "Stereoscopic Endoscope Having Image Transmitting Optical-System and Pupil Dividing Unit that are Axially Movable With Respect to Each Other", which uses a plural pupil dividing means and one optical channel. U.S. Pat. No. 5,751,341 to Chaleki et al., is directed to a "Stereoscopic Endoscope System", which is basically a two channel endoscope, with one or two proximal image sensors. A rigid sheath with an angled distal tip could be attached to its edge and be rotated, for full view.

U.S. Pat. No. 5,800,341 to Mckenna et al., is directed to an "Electronically Steerable Endoscope", which provides different fields of view, without having to move the endoscope, using a plurality of CCD cells and processing means. U.S. Pat. No. 5,825,534 to Strahle, is directed to a "Stereo Endoscope having a Folded Sight Line" including a stereo-endoscope optical channel, having a sight line folded relative to tube axis.

U.S. Pat. No. 5,828,487 to Greening et al., is directed to a "Stereoscopic Viewing System Using a Two Dimensional Lens System" which in general, provides an alternative R-L switching system. This system uses a laterally moving opaque leaf, between the endoscope and the camera, thus using one imaging system. U.S. Pat. No. 5,594,497 to Ahern, describes a distal color CCD, for monocular view in an elongated tube.

The above descriptions provide examples of auto-stereoscopic disclosed techniques, using different switching techniques (Time division multiplexing) and polarization of channels or pupil divisions (spatial multiplexing), all in an elongated shaft. When color image pick up devices are used within these systems, the system suffers from reduced resolution, loss of time related information or a widened cross section.

The issue of color imagery or the issue of a shaft-less endoscope is not embedded into any solution. To offer higher flexibility and to reduce mechanical and optical constraints it is desired to advance the image pick-up device to the frontal part of the endoscope. This allows much higher articulation and lends itself easily to a flexible endoscope. Having a frontal pick up device compromises the resolution of the color device due to size constraints (at this time).

U.S. Pat. No. 5,076,687 to Adelson, is directed to an "Optical Ranging Apparatus" which is, in general a depth measuring device utilizing a lenticular lens and a cluster of pixels.

U.S. Pat. No. 5,760,827 to Faris, is directed to "Pixel Data Processing System and Method for Producing Spectrally-Multiplexed Images of Three-Dimensional Imagery for Use in Stereoscopic Viewing Thereof" and demonstrates the use of multiplexing in color and as such, offers a solution for having a color stereo imagery with one sensor. Nevertheless, such a system requires several sequential passes to be acquired from the object, for creating a stereo color image.

U.S. Pat. No. 5,812,187 to Watanabe, is directed to an Electronic Endoscope Apparatus. This device provides a multi-color image using a monochromatic detector and a mechanical multi-wavelength-illuminating device. The monochromatic detector detects an image, each time the multi-wavelength-illuminating device produces light at a different wavelength.

U.S. Pat. No. 6,306,082 B1 issued to Takahashi, et al., and entitled "Stereoendoscope wherein images having passed through plural incident pupils are transmitted by common relay optical systems", is directed to an apparatus, namely, an endoscope wherein images, having passed through plural incident pupils, are transmitted by a common relay system, and reconstructed at an observation point to provide a streoscopic image. According to the reference, illuminating light is transmitted by a light guide. Light reflected from the illuminated objects passes through non-superimposed pupils and transmitted to the rear side by a common relay system having a single optical axis. The transmitted images are formed on separate image taking surfaces to allow for a streoscopic image to be formed.

U.S. Pat. No. 5,121,452 issued to Stowe, et al., and entitled "Fiber Optic Power Splitter", is directed to a method for manufacturing fiber optic power splitters. The fiber optic power splitter is a unitary, single-mode fiber, fused structure which is composed of four, up to seventeen or more fibers, which provide uniform splitting of input optical power among the fibers. The fiber optic power splitter includes a central fiber and identical surrounding fibers, which are sized prior to fusion, such that mutual contact is achieved. In this manner, each of the surrounding fibers touches the central fiber and the neighboring fibers. In this construction, the surrounding fibers are of the same diameter and the central fiber has a different diameter. Optical power input in the central fiber distributes among the surrounding fibers. The optical power output in the central fiber and the surrounding fibers is monitored during the fusion process, and the fusion process is stopped when the desired fraction of the optical power appears in a surrounding fiber.

In Handbook of Optics, Volume 2, McGraw-Hill, Inc., 1995, p. 15-24, Norman Goldberg discusses the concept of stereo cameras. The structure of a stereo camera is based on the parallax difference between the views of the right and the left eyes. The two lenses in the classic stereo camera are spaced about 65 mm apart, in order to form two images of the subject. Another type of stereo camera uses a reflection system of four mirrors or an equivalent prism system, placed in front of the lens of a normal camera, thereby forming two images of the subject (FIG. 15 on p. 15-25 of the Handbook). According to another method, the subject is required to remain stationary while two separate exposures are made and the camera is shifted 65 mm between the two exposures. This method is employed in aerial stereo photography in which two views are made of the ground, the views being made so many seconds apart.

According to another method, the right and left views of the subject are restricted to the respective eye of the viewer, where the right and the left views are polarized at 90 degrees to one another. The viewer wears glasses with polarizing filters oriented such that each eye sees the view intended for it. In a parallax stereogram, the right and left images are sliced into narrow, interlaced right and left strips. The viewer perceives a three-dimensional view of the subject, while viewing the image through a series of vertical lenticular prisms with a matching pitch.

U.S. Pat. No. 5,233,416 issued to Inoue and entitled "Electronic Endoscope System", is directed to a system which enables the use of an endoscope having either a normal sensitivity or a high sensitivity solid-state image sensor element. The system includes a rotary color wheel, a light source, a condenser lens, the solid-state image sensor element, such as charge coupled device (CCD), an input switch, a first video processor, a second video processor, an output switch, an analog to digital (A/D) converter, a plurality of storage portions, three digital to analog (D/A) converters, an encoder, a first control means, a second control means, a decoder, a master clock and a CCD drive.

The CCD drive is coupled with the CCD, the first control means, and to the master clock. The first control means is coupled with the input switch, the first video processor, the second video processor, the output switch, the A/D converter, the storage portions, the decoder and to the master clock. The CCD is coupled with the decoder and to the input switch. The input switch is coupled with the first video processor and to the second video processor. The output switch is coupled with the first video processor, the second video processor and to the A/D converter. The storage portions are coupled with the A/D converter, to the three D/A converters and to the second control means. The second control means is coupled with the decoder, the master clock, the D/A converters and to the encoder. The three D/A converters are coupled with the encoder.

The condenser lens is located between the light source and the rotary color wheel. The rotary color wheel is located between the condenser lens and a light guide of the endoscope. The rotary color wheel is provided with three filter zones (red, green and blue). The three filter zones are separated by three color-shifting light-blocking zones. Each filter zone is bisected into uniform halves, by an intermediate light-blocking zone.

The input switch switches the system to the first video processor when the normal sensitivity CCD is employed and to the second video processor, when the high sensitivity CCD is employed. The first control means controls the read-out of the signal charges from the CCD and the second control means controls the display of the images. Each of the first control means and the second control means can operate either in a normal sensitivity mode or a high sensitivity mode. The CCD drive produces pulse signals for the CCD, according to the clock signals of the master clock.

The rotary color wheel provides an image to the CCD in red, green and blue, in sequence. When a normal sensitivity CCD is employed, the system switches to the first video processor, and the first control means, the second control means and the CCD drive switch to the normal sensitivity mode. In this mode, the CCD drive enables the read-out of signal charges from the CCD, between every two color-shifting light-blocking zones. The first controller shifts the resulting image to the storage portions, during each color-shifting light-blocking zone. The second controller constructs a color image for each pulse signal, by combining the three images in red, green and blue which are read-out between every two color-shifting light-blocking zones.

When a high sensitivity CCD is employed, the system switches to the second video processor, and the first control means, the second control means and the CCD drive switch to the high sensitivity mode. In this mode, the CCD drive enables the read-out of signal charges from the CCD, between every two color-shifting light-blocking zones, as well as between every two intermediate light-blocking zones. The first controller shifts the resulting image to the storage portions, during each color-shifting light-blocking zone, as well as during each intermediate light-blocking zone. The second controller constructs a color image for each pulse signal, by combining the three images in red, green and blue which are read-out between every two color-shifting light-blocking zones, as well as between every two intermediate light-blocking zones.

SUMMARY OF THE DISCLOSED TECHNIQUE

It is an object of the disclosed technique to provide a novel system for stereoscopic imaging, by employing an image receiving assembly whose inlets are spaced apart, and a novel method for operating the same, which overcomes the disadvantages of the prior art.

In accordance with one aspect of the disclosed technique, there is thus provided a stereoscopic device which includes an image directing assembly, an image differentiator and an image detector. The image directing assembly includes a first light inlet for receiving a first image and a second light inlet for receiving a second image, wherein the first light inlet and the second light inlet are spaced apart. The image differentiator differentiates between the first image and the second image and the image directing assembly directs the first image and the second image to the image detector via a common path.

A controller coupled with the image detector and to an image processor, enables the image detector to detect the first image and the second image according to the state of the image differentiator. The image processor produces a stereoscopic image, by processing the detected first image and second image.

In accordance with another aspect of the disclosed technique, there is thus provided a method for producing a stereoscopic image. The method includes the procedures of receiving images of different sides of an object through two spaced apart apertures, directing the images to a common path and differentiating between the images. The method further includes the procedures of detecting the images, processing the detected images and displaying a stereoscopic image according to the processed images.

In accordance with a further aspect of the disclosed technique, there is thus provided a stereoscopic device including a first light filter, a second light filter, a sequential wavelength differentiator, an image detector and an optical assembly located in front of the image detector. The first light filter admits light at a plurality of first ranges of filter wavelengths and the second light filter admits light at a plurality of second ranges of filter wavelengths. The sequential wavelength differentiator is associated with a first set of differentiating wavelengths and with a second set of differentiating wavelengths.

The image detector receives images from the first light filter and from the second light filter. The first set of differentiating wavelengths is included in at least one of the first ranges of filter wavelengths and excluded from the second ranges of filter wavelengths. The second set of differentiating wavelengths is included in at least one of the second ranges of filter wavelengths and excluded from the first ranges of filter wavelengths. A controller is coupled with the image detector, to the image processor and to the sequential wavelength differentiator. The controller enables the image detector to detect the first image and the second image according to the state of the sequential wavelength differentiator. The image processor produces a stereoscopic image, by processing the detected first image and second image.

The sequential wavelength differentiator can be a sequential illuminator, sequentially emitting light at least a portion of the first set of differentiating wavelengths and at least a portion of the second set of differentiating wavelengths. Alternatively, the sequential wavelength differentiator can be a filtering differentiator, differentiating between at least a portion of the first ranges of filter wavelengths and at least a portion of the second ranges of filter wavelengths.

Further alternatively, the filtering differentiator can be a multi-wavelength rotating disk located in front of the image detector, wherein the multi-wavelength rotating disk includes a plurality of filtering sectors. Each of the filtering sectors admits light at different wavelengths selected from one of the first set of differentiating wavelengths and the second set of differentiating wavelengths. The multi-wavelength rotating disk sequentially filters light at the common path and the controller enables the image detector to detect images, according to the angular position of the multi-wavelength rotating disk.

In accordance with another aspect of the disclosed technique, there is thus provided a method for detecting a first image and a second image. The method includes the procedure of determining a plurality of first ranges of filter wavelengths for a first pupil and a plurality of second ranges of filter wavelengths for a second pupil. The method further includes the procedure of sequentially differentiating between a first set of differentiating wavelengths and a second set of differentiating wavelengths. The method includes still further, the procedure of detecting the first image when the first set of differentiating wavelengths is present, and detecting the second image when the second set of differentiating wavelengths is present. The first set of differentiating wavelengths is included in the first ranges of filter wavelengths and excluded from the second ranges of filter wavelengths. The second set of differentiating wavelengths is included in the second ranges of filter wavelengths and excluded from the first ranges of filter wavelengths.

BRIEF DESCRIPTION OF THE DRAWINGS

The disclosed technique will be understood and appreciated more fully from the following detailed description taken in conjunction with the drawings in which:

FIG. 39A is a schematic illustration of a partially-transparent rotating disk, constructed and operative in accordance with a further embodiment of the disclosed technique;

FIG. 39B is a schematic illustration of a partially-transparent rotating disk, constructed and operative in accordance with another embodiment of the disclosed technique;

FIG. 40A is a schematic illustration of a multi-wavelength rotating disk, constructed and operative in accordance with a further embodiment of the disclosed technique;

FIG. 40B is a schematic illustration of a multi-wavelength rotating disk, constructed and operative in accordance with another embodiment of the disclosed technique;

DETAILED DESCRIPTION OF THE EMBODIMENTS

The disclosed technique overcomes the disadvantages of the prior art by providing a continuous imaging stereoscopic apparatus, using a generally lenticular lens layer, a light sensor array and an image processing system.

Figure 1:
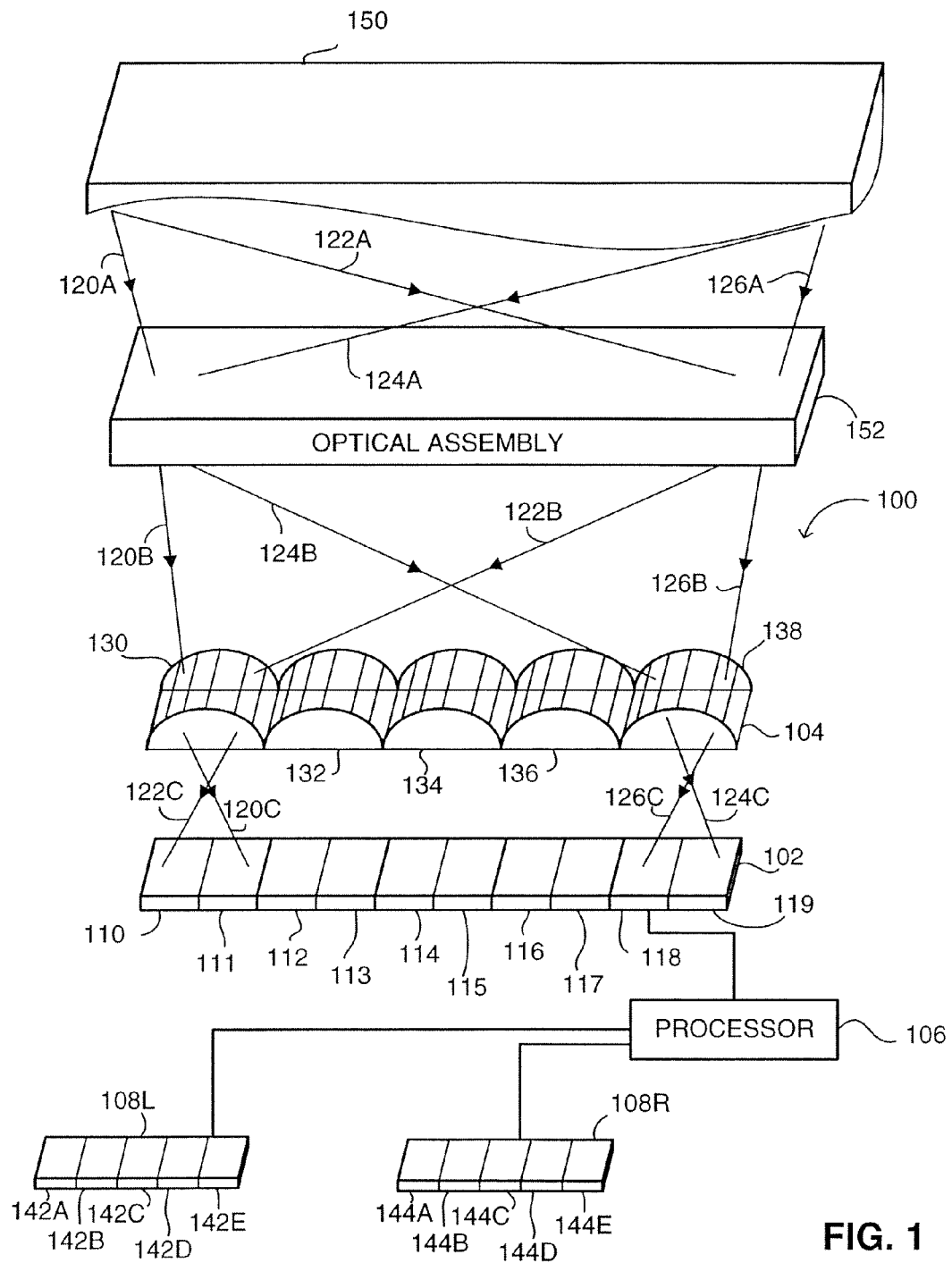
FIG. 1 is a schematic illustration of a three-dimensional object and a stereoscopic imaging apparatus, constructed and operative in accordance with an embodiment of the disclosed technique.

Reference is now made to FIG. 1, which is a schematic illustration of a three-dimensional object 150 and a stereoscopic imaging apparatus, generally referenced 100, constructed and operative in accordance with an embodiment of the disclosed technique. Apparatus 100 includes a lenticular lens layer 104, a light sensor array 102, a processor 106 and two display devices 108R and 108L. Apparatus 100 is placed in front of three-dimensional object 150. An optical assembly 152 is placed between apparatus 100 and object 150, for focusing the image of object 150 on light sensor array 102.

Light sensor array 102 includes a plurality of sensors 110, 111, 112, 113, 114, 115, 116, 117, 118 and 119. Lenticular lens layer 104 includes a plurality of lenticular elements 130, 132, 134, 136 and 138. Each one of the lenticular elements is located above two light sensors, in a way that lenticular element 130 is located above sensors 110 and 111, lenticular element 132 is located above sensors 112 and 113, lenticular element 134 is located above sensors 114 and 115, lenticular element 136 is located above sensors 116 and 117 and lenticular element 138 is located above sensors 118 and 119.

The light sensors 110, 111, 112, 113, 114, 115, 116, 117, 118, and 119, detect light as directed by the lenticular lens elements 130, 132, 134, 136 and 138, and provide respective information to the processor 106. The processor 106 processes this information, produces a pair of images, as will be explained in detail herein below, and provides them to the display units 108R and 108L, which in turn produce visual representations of these images.

In general, each lenticular element directs light rays, which arrive from a predetermined direction to a predetermined location, and light rays which arrive from another predetermined direction, to another predetermined location. Hence, the disclosed technique, utilizes the lenticular lens layer to distinguish between a right view image and a left view image, as is described herein below.

Each of the display units 108R and 108L includes a plurality of display units also known as pixels. Display unit 108L includes pixels 142A, 142B, 142C, 142D and 142E. Display unit 108R includes pixels 144A, 144B, 144C, 144D and 144E. Using these pixels each of the display units 108R and 108L produces an image, according to data provided from the processor 106. The two images, each viewed by a different eye of the user, produce a sensation of a three-dimensional image.

Light rays 124A, and 126A represent a right-side image of the three-dimensional object 150. Light rays 120A, and 122A represent a left side image of the three-dimensional object 150. The optical assembly 152 redirects light rays 120A, 122A, 124A and 126A so as to focus them on a plain which is determined by the light sensor array 102, as light rays 120B, 122B, 124B and 126B, respectively. Hence, light rays 122B and 126B represent a focused right side view of the three-dimensional object 150, and light rays 120B and 124B represent a focused left side view of the three-dimensional object 150.

The lenticular lens layer 104 directs the focused right side view light rays 122B and 126B to light sensors 110 and 118, respectively, as respective light rays 122C and 126C. In addition, the lenticular lens layer 104 directs the focused left side view light rays 120B and 124B to light sensors 111 and 119, respectively. In general, light sensors 111, 113, 115, 117 and 119 detect light rays which relate to a left side view image of object 150, and light sensors 110, 112, 114, 116, and 118, detect light rays which relate to a right side view image of object 150.

Hence, light sensors 110, 112, 114, 116 and 118 detect the right side image of object 150, while light sensors 111, 113, 115, 117 and 119 detect the left side image of object 150. The light sensor array 102 provides data relating to the detected light intensity at each of the light sensors to the processor 106. It is noted that in the following description, the term processor, refers to a control unit which is adapted for a given situation such as a CPU, a controller, a processor, a gated element, a timing unit such as a clock, and the like. Accordingly, the terms CPU, controller, processor, gated element, timing unit, clock, and the like, are interchangeable, with respect to a given architecture or a given method.

The processor 106 processes this data, produces a right side image from the data relating to the right side view and a left side image from the data relating to the left side view, and provides the respective image to the respective display unit 108R and 108L. In the present example, the processor 106 utilizes the data received from sensors 110, 112, 114, 116 and 118 to determine the data provided to pixels 144A, 144B, 144C, 144D and 144E, respectively. Similarly, the processor 106 utilizes the data received from sensors 111, 113, 115, 117 and 119 to determine the data which is to be provided to pixels 142A, 142B, 142C, 142D and 142E, respectively.

According to the disclosed technique, the right side image and the left side image are detected at the same time and hence, can also be displayed at the same time. According to another aspect of the disclosed technique, each of the light sensors 110, 111, 112, 113, 114, 115, 116, 117, 118, and 119, includes a plurality of color sensing elements, which together cover a predetermined spectrum, as will be described in detail herein below.

Figure 2:
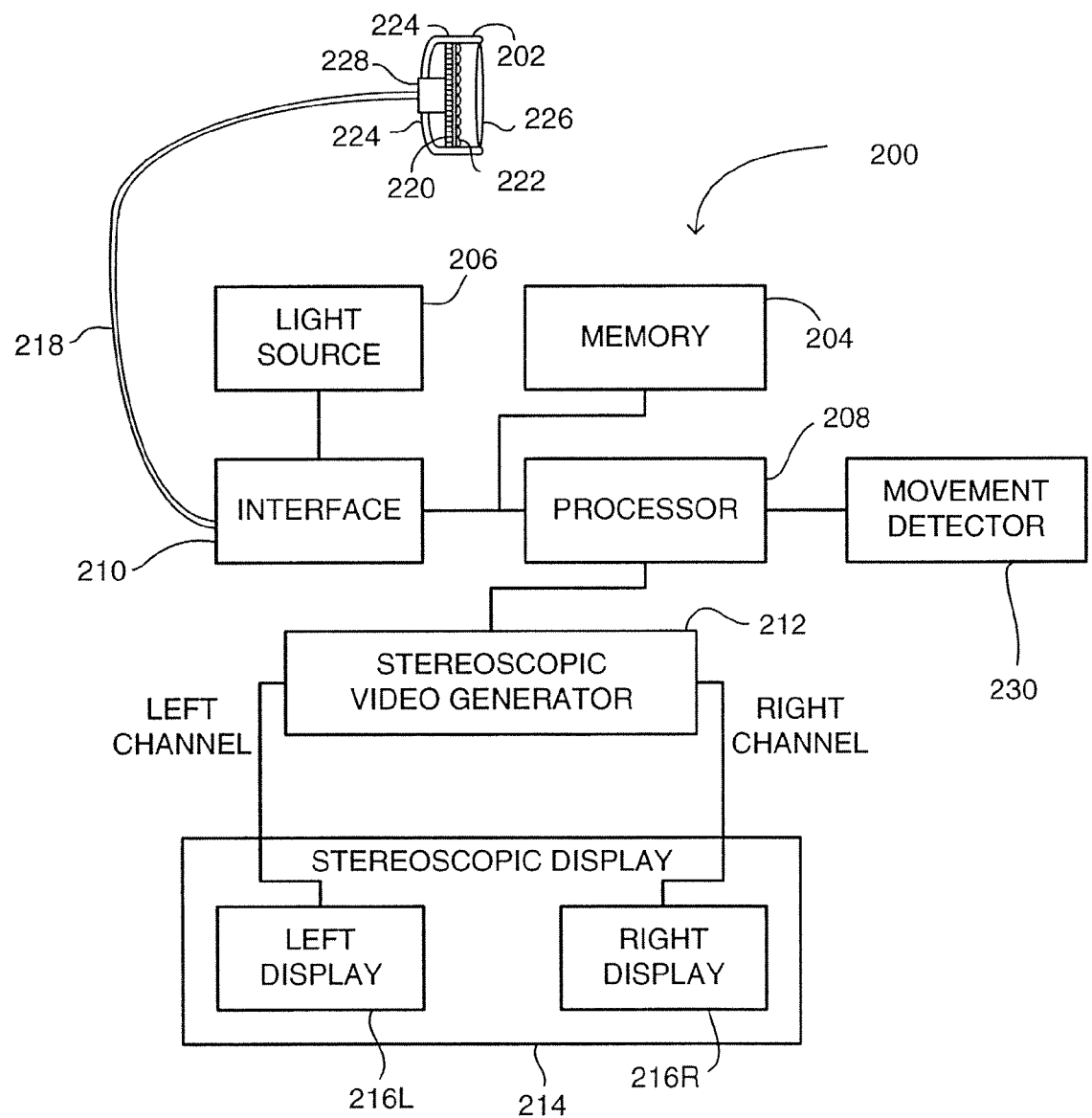
FIG. 2 is a schematic illustration of a stereoscopic imaging apparatus, constructed and operative in accordance with another embodiment of the disclosed technique.

Reference is now made to FIG. 2, which is a schematic illustration of a stereoscopic imaging apparatus, generally referenced 200, constructed and operative in accordance with another embodiment of the disclosed technique. Apparatus 200 includes a sensor assembly 202, an interface 210, a processor 208, a movement detector 230, a light source 206, a memory unit 204, a stereoscopic video generator 212 and a stereoscopic display 214. The sensor assembly 202 is coupled with the interface 210 by a flexible cord 218. The interface 210 is coupled with processor 208, memory unit 204, and with light source 206. The processor 208 is further coupled with the memory unit 204, movement detector 230 and with the stereoscopic video generator 212. The stereoscopic video generator 212 is further coupled with the stereoscopic display 214. Movement detector 230 detects the movement of sensor assembly 202 relative to an object. For this purpose, movement detector 230 is attached to sensor assembly 202. In the case of a rigid endoscope, the movement detector 230 can be attached to any part of the endoscope rod (not shown), since the movement of the endoscope head can be determined according to the movement of any point of the endoscope rod. The operation of system 200, according to data received from movement detector 230, is described herein below.

The sensor assembly 202 includes a focusing element, which in the present example is a lens 226, a lenticular lens layer 222, a light sensor array 220, an interface 228 and a light projecting means 224. The lenticular lens layer 222 is attached to the light sensor array 220. According to the disclosed technique, the light sensor array 220 can be any type of sensing array, such as a CCD detector, a CMOS detector, and the like. The light sensor array 220 is coupled with the interface 228, which can also acts as a supporting base.

The stereoscopic display 214 includes two display units, a left display unit 216L (for placing in front of the left eye of the user) and a right display unit 216R (for placing in front of the right eye of the user). Hence, the stereoscopic display 214 is capable of displaying stereoscopic images continuously. Such a stereoscopic display unit is for example the ProView 50 ST head-mounted display, manufactured and sold by Kaiser Electro-Optics Inc., a US registered company, located in Carlsbad, Calif. Another example for a stereoscopic display unit is the virtual retinal display (VRD) unit, which is provided by MICROVISION Inc., a US registered company, located in Seattle, Wash. It is noted that any method, which is known in the art for displaying stereoscopic, and for that matter three-dimensional images, is applicable for the disclosed technique.

The image received from a three-dimensional object is received at the sensor assembly 202, focused by lens 226, optically processed by the lenticular lens layer 222 and finally detected by the light sensor array 220. The lenticular lens layer 222 directs light coming from one predetermined direction to predetermined light sensors of the light sensor array 220, and light coming from another predetermined direction to other predetermined light sensors of the light sensor array 220. Accordingly, light sensor array 220 detects two images of the same object, a right side image and a left side image, each from a different direction. This aspect of the disclosed technique is described in detail hereinabove, in conjunction with FIG. 1.

An electronic representation of this information is partially processed by the interface 228 and then provided to the interface 210, via flexible cord 218. It is noted that flexible cord 218 may include digital communication linking means such as optic fibers or electrical wires, for transferring data received from light sensor array 220, as well as light guiding conducting means for conducting light from light source 206 to the light projecting means 224. According to the disclosed technique, flexible cord 218 can be replaced with a rigid cord (not shown), if necessary.

The data received at interface 210 includes information, which relates to the two images and has to be processed so as to distinguish them from each other. As the processor 208 processes the information, it uses the memory unit 204 as temporarily storage.

After processing the information, the processor 208 produces two matrices each being a reconstructed representation relating to one of the originally detected images. The processor provides these matrixes to the stereoscopic video generator 212, which in turn produces two respective video signals, one for the left view image and another for the right view image.

The stereoscopic video generator 212 provides the video signals to the stereoscopic display 214, which in turn produces two images, one using right display unit 216R and another using left display unit 216L.

It is noted that the general size of the sensor assembly 202 is dictated by the size of the sensor array and can be in the order of a few millimeters or a few centimeters. This depends on the size of each of the sensors in the array and the total number of sensors (i.e. the required optical resolution).

According to one aspect of the disclosed technique, each of the sensors in light sensor array 220, is a full range sensor, which yields data relating to a gray scale stereoscopic image. According to another aspect of the disclosed technique, each of the sensors in the light sensor array, can be adapted so as to provide full color detection capabilities.

Figure 3A:
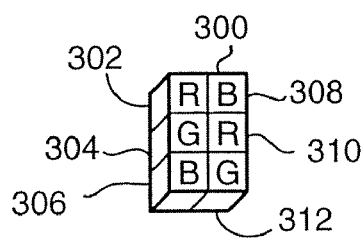
FIG. 3A is a schematic illustration of a super-pixel, constructed and operative in accordance with a further embodiment of the disclosed technique.

Reference is now made to FIG. 3A, which is a schematic illustration of a super-pixel, generally referenced 300, constructed and operative in accordance with a further embodiment of the disclosed technique. Super-pixel 300 includes a left section of sensors which includes three sensors 302, 304 and 306, and a right section of sensors which also includes three sensors 308, 310 and 312. Sensors 302 and 310 detect generally red colored light, sensors 304 and 312 detect generally green colored light and sensors 306 and 308 detect generally blue colored light. Hence, each of the sections includes a complete set of sensors for detecting light in the entire visible spectrum.

Figure 3B:
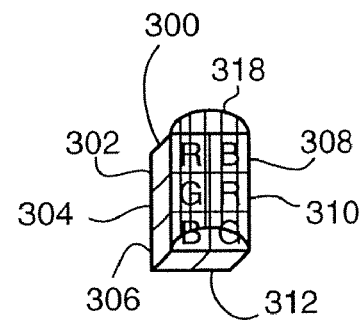
FIG. 3B is a schematic illustration of the super-pixel of FIG. 3A and a lenticular element, constructed and operative in accordance with another embodiment of the disclosed technique.

Reference is further made to FIG. 3B, which is a schematic illustration of the super-pixel 300 of FIG. 3A and a lenticular element, generally referenced 318, constructed and operative in accordance with another embodiment of the disclosed technique. The lenticular element 318 is located on top of super-pixel 300, such that its right side covers the right section of the super-pixel 300, and its left side covers the left section of the super-pixel 300. Accordingly, the lenticular element 318 directs light, which arrives from the right (right view image), to the left section of the super-pixel 300, where it is detected in full spectrum by sensors 302, 304 and 306.

The data provided by these sensors can later be utilized to reconstruct an image in full color. Similarly, the lenticular element 318 directs light, which arrives from the left (left view image), to the right section of the super-pixel 300, where it is detected in full spectrum by sensors 308, 310 and 312.

Figure 3C:
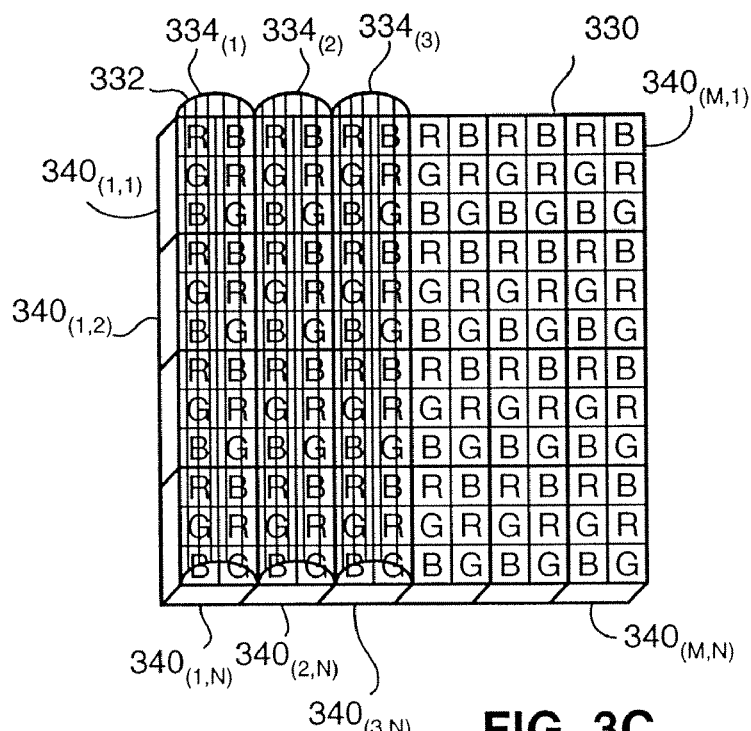
FIG. 3C is a schematic illustration of a sensor array and a lenticular lens layer, constructed and operative in accordance with a further embodiment of the disclosed technique.

Reference is now made to FIG. 3C, which is a schematic illustration of a sensor array, generally referenced 330, and a lenticular lens layer, generally referenced 332, constructed and operative in accordance with a further embodiment of the disclosed technique. Sensor array 330 is a matrix of M×N super-pixels, which are generally referenced 340. For example, the upper left super-pixel is denoted $340_{(1,1)}$, the last super-pixel in the same column is denoted $340_{(1,N)}$ and the lower-right pixel is denoted $340_{(M,N)}$. Lenticular lens layer 332, of which three lenticular elements are shown (referenced 334), is placed over the sensor array 330.

Lenticular element $334_{(1)}$ covers the first column of super-pixels 340 from super-pixel $340_{(1,1)}$ to super-pixel $340_{(1,N)}$. Lenticular element $334_{(2)}$ covers the second column of super-pixels 340 from super-pixel $340_{(2,1)}$ to super-pixel $340_{(2,N)}$. Lenticular element $334_{(3)}$ covers the third column of super-pixels 340 from super-pixel $340_{(3,1)}$ to super-pixel $340_{(3,N)}$. Accordingly, each of the lenticular elements of the lenticular lens layer covers an entire column of super-pixels.

It is noted that a super-pixel according to the disclosed technique can include sensors in any set of colors such as red-green-blue (RGB), cyan-yellow-magenta-green (CYMG), infra-red, ultra-violet, and the like, in any arrangement or scheme such as column, diagonals, and the like. It is noted that such a set of colors can be achieved either by using specific color sensitive detectors or by using color filters over the wide spectrum detectors.

The output of a conventional CYMG sensor array can include a plurality of values, each of which is equal to the sum of two cells in the same column and in adjacent rows. The following sums may apply in a conventional CYMG sensor array—Cyan+Magenta, Yellow+Green, Cyan+Green and Yellow+Magenta.

Figure 4:
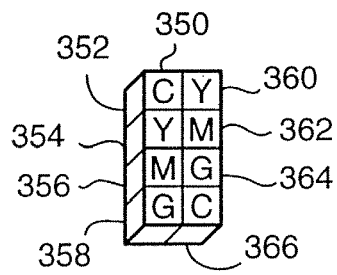
FIG. 4 is a schematic illustration of a super-pixel, constructed and operative in accordance with another embodiment of the disclosed technique.

Reference is further made to FIG. 4, which is a schematic illustration of a super-pixel, generally referenced 350, constructed and operative in accordance with another embodiment of the disclosed technique. Super-pixel 350 includes a left section of sensors which includes four sensors 352, 354, 356 and 358 and a right section of sensors which also includes four sensors 360, 362, 364 and 366. Sensors 352 and 366 detect generally cyan colored light, sensors 354 and 360 detect generally yellow colored light, sensors 356 and 362 detect generally magenta colored light and sensors 358 and 364 detect generally green colored light. Hence, each of the sections includes a complete set of sensors for detecting light in the entire visible spectrum.

Figure 5A:
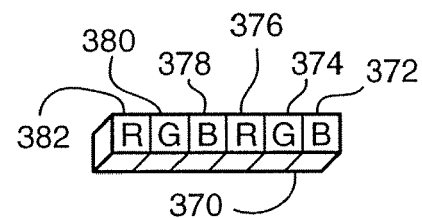
FIG. 5A is a schematic illustration of a color super-pixel, constructed and operative in accordance with a further embodiment of the disclosed technique.
Figure 5B:
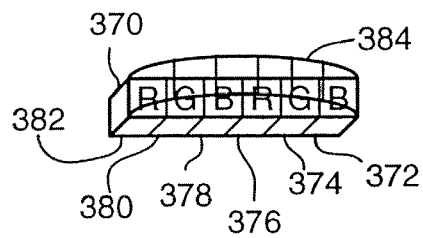
FIG. 5B is a schematic illustration of the color super-pixel of FIG. 5A, with a single lenticular element, constructed and operative in accordance with another embodiment of the disclosed technique.
Figure 5C:
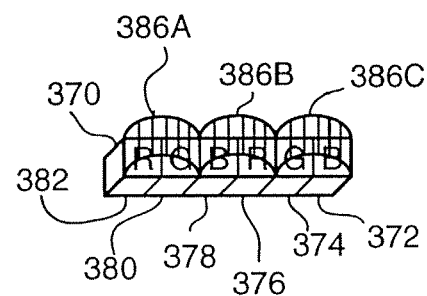
FIG. 5C is a schematic illustration of the color super-pixel of FIG. 5A, combined with three lenticular elements, constructed and operative in accordance with a further embodiment of the disclosed technique.

Reference is further made to FIGS. 5A, 5B and 5C. FIG. 5A is a schematic illustration of a super-pixel, generally referenced 370, constructed and operative in accordance with a further embodiment of the disclosed technique. FIG. 5B is a schematic illustration of super-pixel 370 combined with a single lenticular element, generally referenced 384, constructed and operative in accordance with another embodiment of the disclosed technique. FIG. 5C is a schematic illustration of super-pixel 370 combined with three lenticular elements, generally referenced 386, constructed and operative in accordance with a further embodiment of the disclosed technique.

The color arrangement which is provided for super-pixel 370 is typical for vertical light detection arrays, where each column of sensors is coated with light filtering layer of a different color. As can be seen in FIG. 5A, super-pixel 370 includes a plurality of light sensors 372, 374, 376, 378, 380 and 382. Light sensors 372 and 378 are blue color range sensors. Light sensors 374 and 380 are green color range sensors. Light sensors 376 and 382 are red color range sensors.

Figure 6:
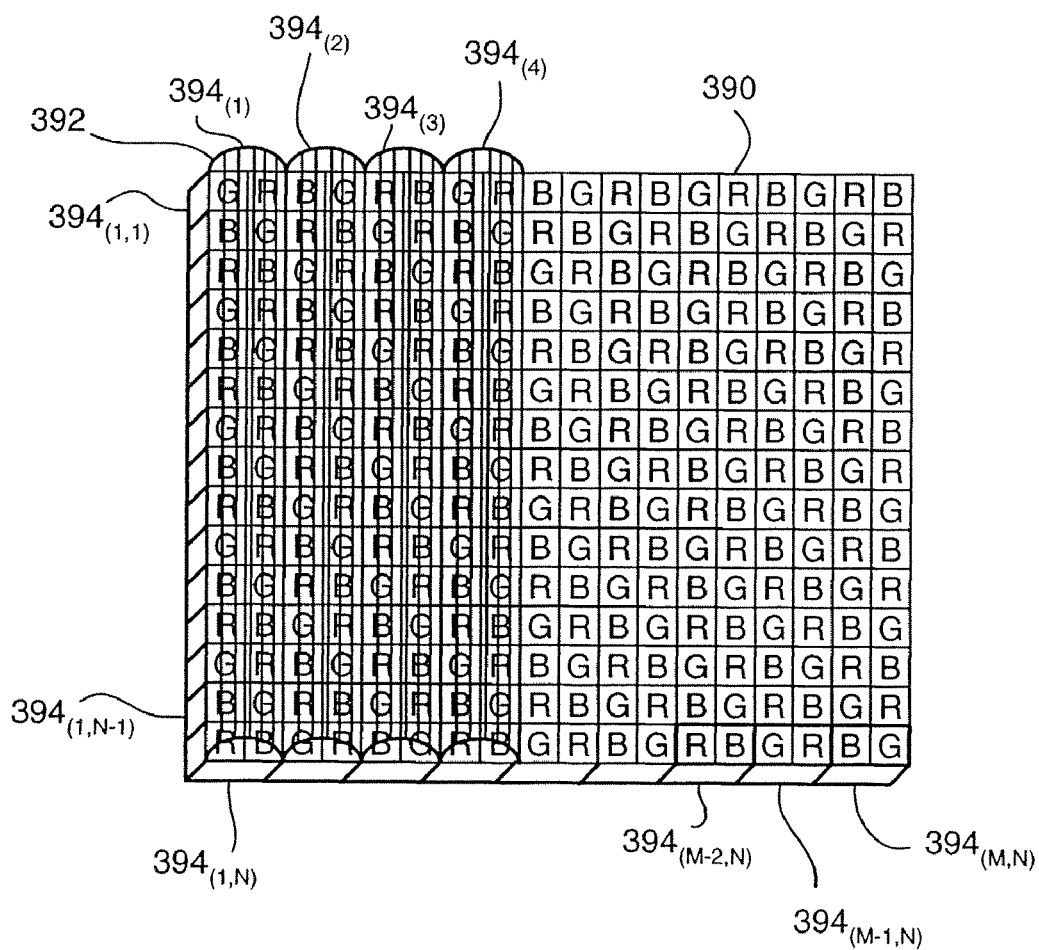
FIG. 6 is a schematic illustration of a sensor array and a lenticular lens layer, constructed and operative in accordance with another embodiment of the disclosed technique.

Reference is now made to FIG. 6, which is a schematic illustration of a sensor, generally referenced 390, and a lenticular lens layer, generally referenced 392, constructed and operative in accordance with another embodiment of the disclosed technique. Sensor 390 is logically divided into a plurality of super-pixels, generally referenced $394_{(x,y)}$. For example, the upper-left super-pixel is referenced $394_{(1,1)}$ and the lower-right side super-pixel is referenced $394_{(M,N)}$. As can be seen from FIG. 6, the color arrangement of sensor 390 is diagonal. Hence, each super pixel has a different color arrangement, and generally speaking, there are several types of super-pixels, such as red-blue (super pixel $394_{(M-2,N)}$), green-red (super pixel $394_{(M-1,N)}$) and blue-green (super pixel $394_{(M,N)}$).

Figure 7A:
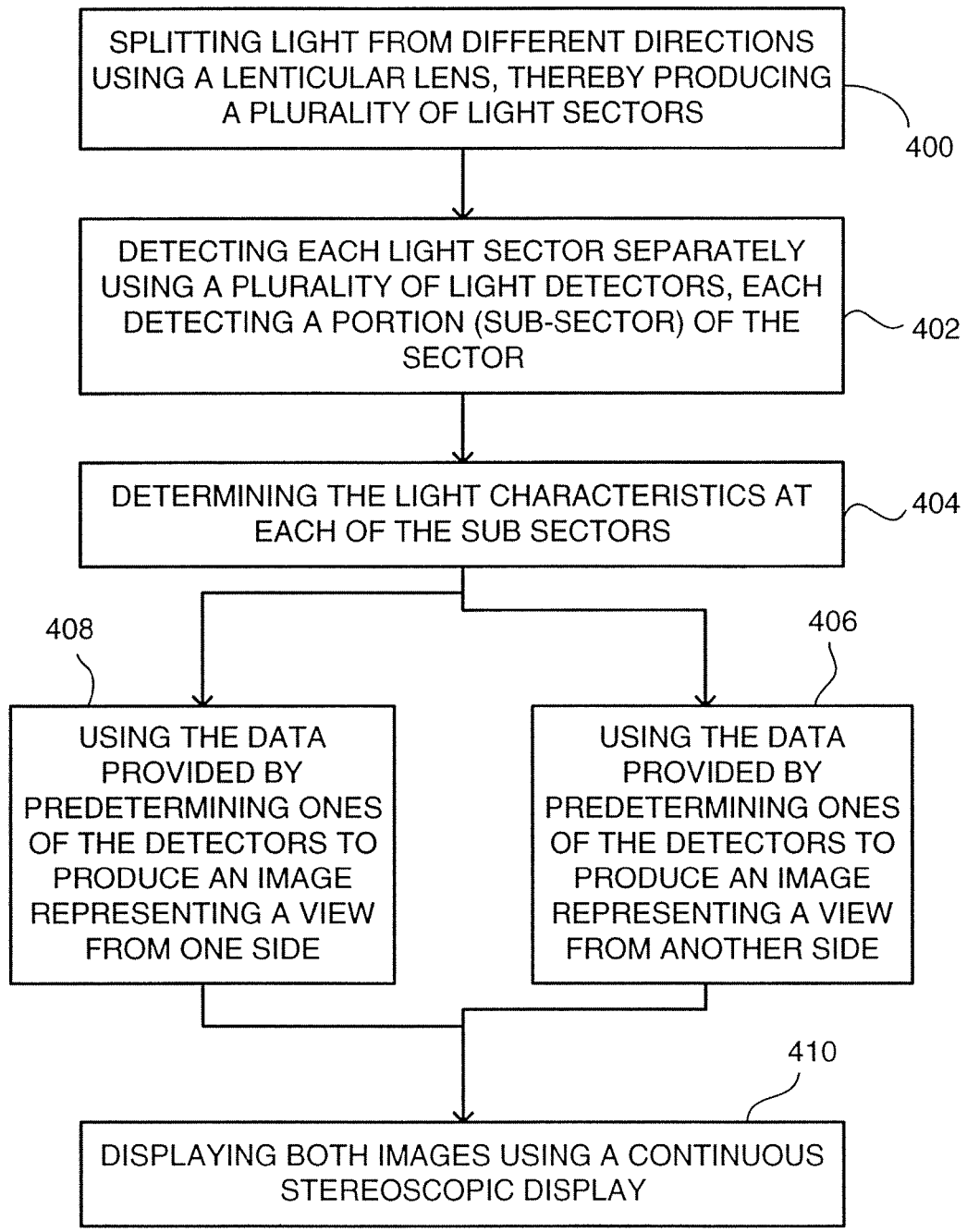
FIG. 7A is a schematic illustration of a method for operating the apparatus of FIG. 2, operative in accordance with a further embodiment of the disclosed technique.

Reference is now made to FIG. 7A, which is a schematic illustration of a method for operating apparatus 200, operative in accordance with a further embodiment of the disclosed technique. In step 400, the apparatus 200 splits light which arrives from different directions, utilizing the lenticular lens 222. Each of the lenticular elements produces two light sectors, one sector which includes light rays arriving from the left side, and another sector which includes light rays arriving from the right side.

In step 402, the apparatus detects each light sector separately, using a plurality of light detectors, each detecting a portion of its respective sector. With reference to FIG. 3B, sensors 302, 304 and 306 detect light which arrives from the lenticular element 318, at the left side sector and sensors 308, 310 and 312 detect light which arrives from the lenticular element 318, at the right side sector. Each of the sensors detects light at a sub-sector.

In step 404, the apparatus 200 determines the light characteristics as detected by each of the light sensors, at each of the sub-sectors. In step 408, the apparatus 200 utilizes the data, which was accumulated from selected sub-sectors to determine and produce an image representing a view from one side. In step 406, the apparatus 200 utilizes the data, which was accumulated from other selected sub-sectors to determine and produce an image representing a view from another side. In step 410, the apparatus 200 displays both images using a continuous stereoscopic display device.

According to a further aspect of the disclosed technique, information from selected pixels can be used to enhance information for other pixels. For example, color information of pixels, which are associated with a first color, is used for extrapolating that color at the location of another pixel, associated with a second color.

Figure 7B:
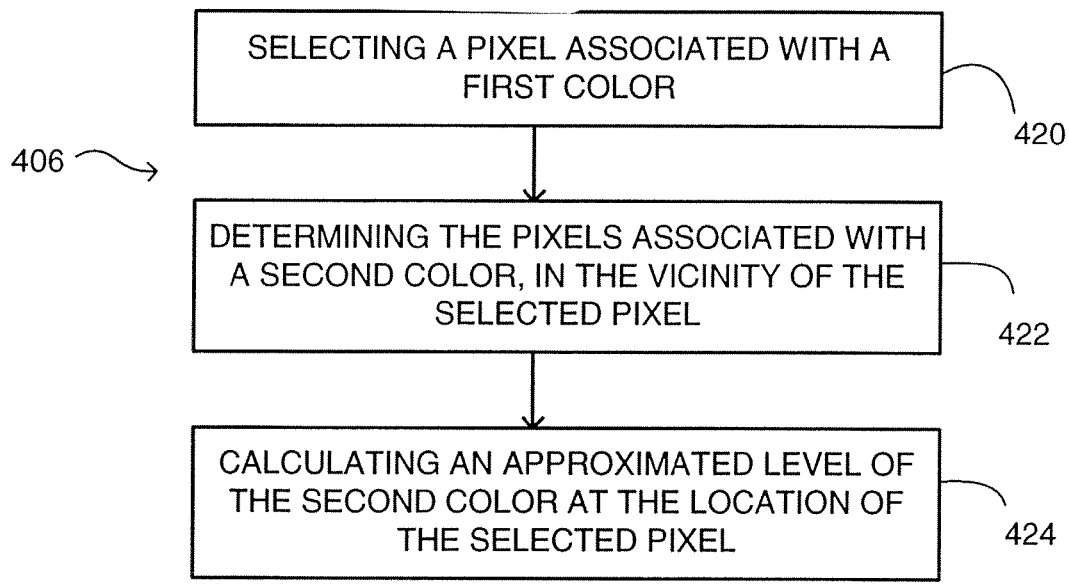
FIG. 7B is an illustration in detail of a step of the method of FIG. 7A.
Figure 7C:
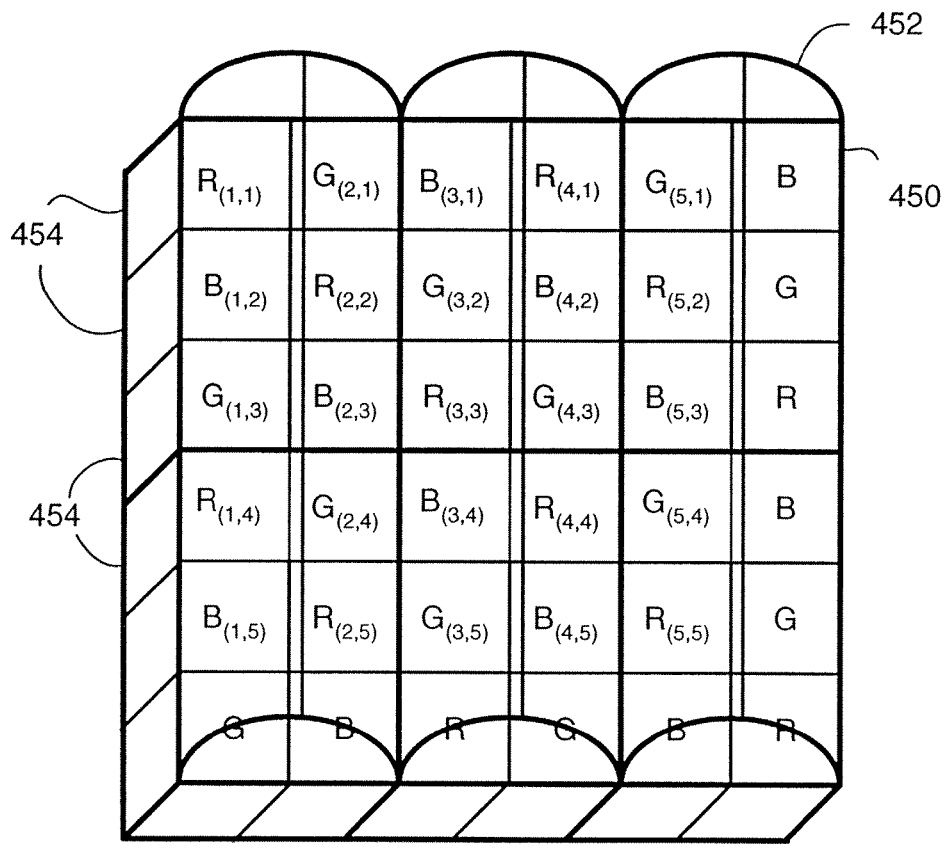
FIG. 7C is a schematic illustration of a sensor array and a lenticular lens layer, constructed and operative in accordance with another embodiment of the disclosed technique.

Reference is further made to FIGS. 7B and 7C. FIG. 7B is an illustration in detail of step 406 of FIG. 7A. FIG. 7C is a schematic illustration of a sensor array, generally referenced 450, and a lenticular lens layer, generally referenced 452, constructed and operative in accordance with another embodiment of the disclosed technique. Sensor array 450 includes a plurality of pixel sensors, referenced 454, each associated with a selected color. For example, pixel sensors $R_{(1,1)}$, $R_{(2,2)}$, $R_{(3,3)}$, $R_{(4,4)}$, $R_{(1,4)}$ and $R_{(4,1)}$ are associated with the red color. Pixel sensors $G_{(2,1)}$, $G_{(3,2)}$, $G_{(4,3)}$, $G_{(1,3)}$ and $G_{(2,4)}$ are associated with the green color. Pixel sensors $B_{(1,2)}$, $B_{(2,3)}$, $B_{(3,4)}$, $B_{(3,1)}$ and $B_{(4,2)}$ are associated with the blue color.

In step 420, the system, according to the disclosed technique, selects a pixel sensor, associated with a first color. With reference to FIG. 7C, the selected pixel sensor according to the present example is pixel sensor $R_{(3,3)}$.

In step 422, the system determines pixels, associated with a second color, in the vicinity of the selected pixel. It is noted that these pixels can also be restricted to ones, which relate to the same image side of the selected pixel. With reference to FIG. 7C, the second color is green and the green pixel sensors, in the vicinity of pixel sensor $R_{(3,3)}$, respective of the same image side are pixel sensors $G_{(5,1)}$, $G_{(3,2)}$, $G_{(3,5)}$, $G_{(5,4)}$, and $G_{(1,3)}$.

In step 424, the system calculates an approximation of the level of the green color at the location of the selected pixel $R_{(3,3)}$. It is noted that the calculation can include a plurality of approximation procedures, such as calculating the weighted average level, depending on the location of pixel sensors $G_{(5,1)}$, $G_{(3,2)}$, $G_{(3,5)}$, $G_{(5,4)}$, and $G_{(1,3)}$, with respect to the location of the selected pixel sensor $R_{(3,3)}$. Similarly, blue color level at the location of the selected pixel sensor $R_{(3,3)}$, can be calculated using the information received from pixel sensors $B_{(1,2)}$, $B_{(1,5)}$, $B_{(3,1)}$, $B_{(3,4)}$ and $B_{(5,3)}$. Hence the disclosed technique provides a method for enhancing picture resolution by means of color information interpolation, using image processing.

It is noted that none of the lenticular elements is necessarily round shaped, but can be formed according to other optical structures which are based on various prism designs, and the like, which provide the directing of beams of light coming from different directions to different directions.

Figure 8:
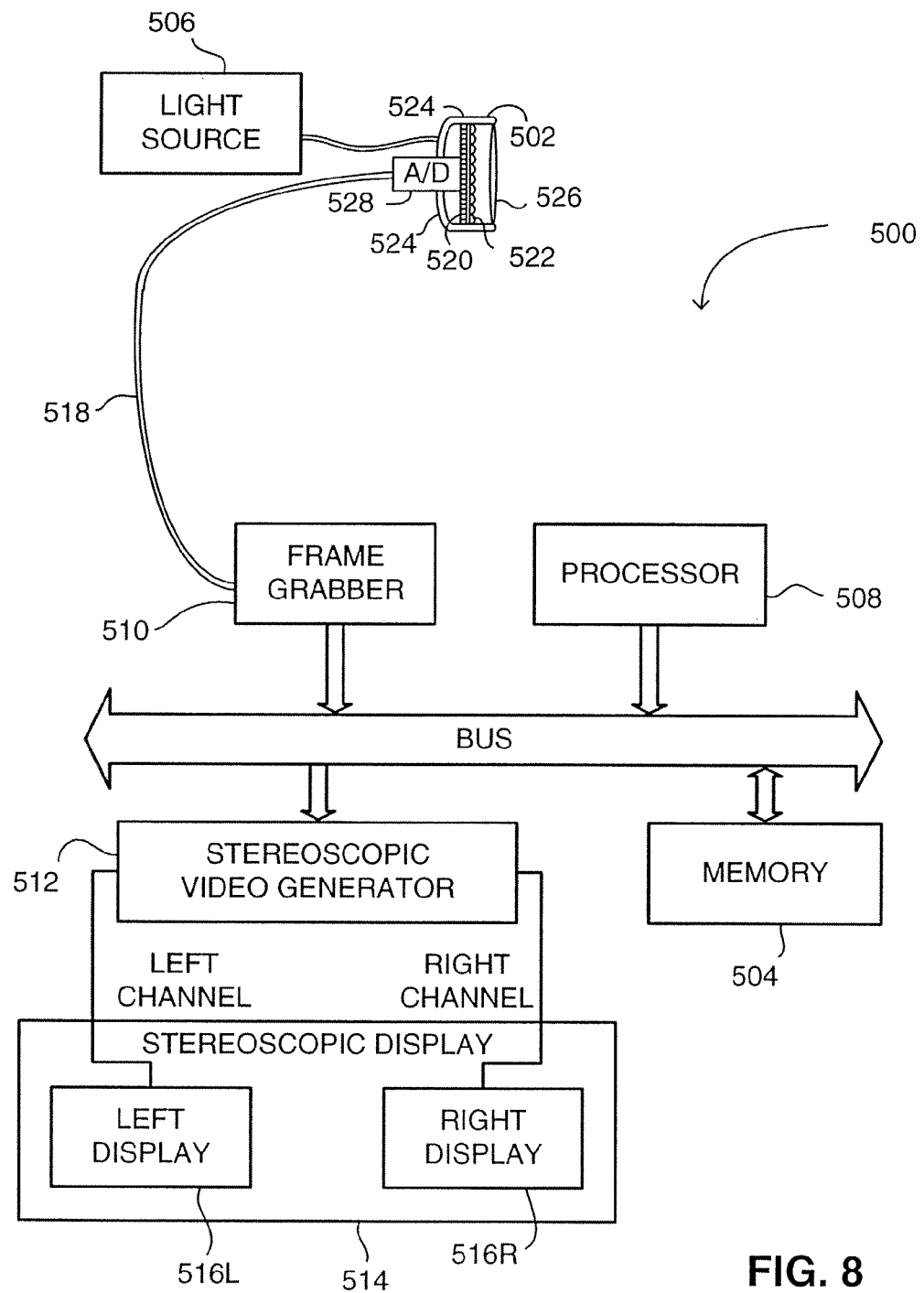
FIG. 8 is a schematic illustration of a stereoscopic imaging apparatus, constructed and operative in accordance with a further embodiment of the disclosed technique.

Reference is now made to FIG. 8, which is a schematic illustration of a stereoscopic imaging apparatus, generally referenced 500, constructed and operative in accordance with a further embodiment of the disclosed technique. Apparatus 500 includes a sensor assembly 502, a frame grabber 510, a processor 508, a light source 506, a memory unit 504, a stereoscopic video generator 512 and a stereoscopic display 514. The sensor assembly 502 is coupled with the frame grabber 510 by a flexible cord 518. The frame grabber 510, the processor 508, the memory unit 504 and the stereoscopic video generator 512 are all interconnected via a common bus.

The sensor assembly 502 is generally similar to the sensor assembly 202, as described herein above in conjunction with FIG. 2. The sensor assembly 502 includes a lens 526, a lenticular lens layer 522, a light sensor array 520, an analog to diconverter (A/D) 528 and a light projecting means 524. The lenticular lens layer 522 is attached to the light sensor array 520. Light sensor array 520 is coupled with the A/D 528, which could also act as a supporting base. The light projecting means 524 is coupled with light source 506, which provides light thereto.

The stereoscopic display 514 includes two display units, a left display unit 516L (for placing in front of the left eye of the user), and a right display unit 516R (for placing in front of the right eye of the user). Hence, the stereoscopic display 514 is capable of displaying stereoscopic images continuously. A/D converter 528 converts analog information received from light sensor array 522 into digital format and provides the digital information to frame grabber 510.

The digital information is received by the frame grabber 510 and hence made available to the processor 508 via the bus. As the processor 508 processes the information, it uses the memory unit 504 as temporary storage. After processing the information, the processor 508 produces two matrices each being a reconstructed representation relating to one of the originally detected images. The processor 508 provides these matrices to the stereoscopic video generator 512, which in turn produces two respective video signals, one for the left view image and another for the right view image. The stereoscopic video generator 512 provides the video signals to the stereoscopic display 514, which in turn produces two images, one using right display unit 516R and another using left display unit 516L.

Figure 9A:
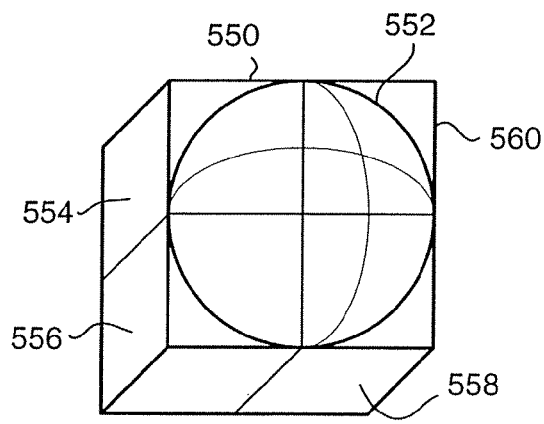
FIG. 9A is a view in perspective of a section of light sensors, and a lenticular element, constructed and operative in accordance with another embodiment of the disclosed technique.
Figure 9B:
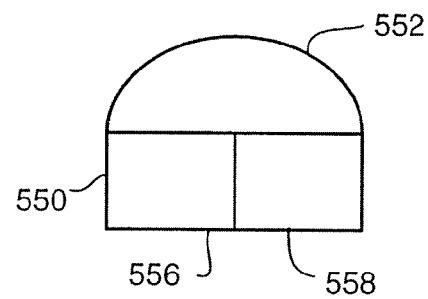
FIG. 9B is a view from the bottom of the lenticular element and the section of light sensors of FIG. 9A.
Figure 9C:
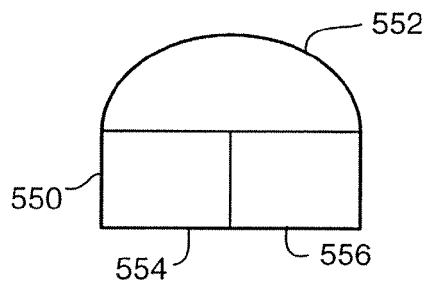
FIG. 9C is a view from the side of the lenticular element and the section of light sensors of FIG. 9A.

Reference is now made to FIGS. 9A, 9B and 9C. FIG. 9A is a view in perspective of a super-pixel, generally referenced 550, and a lenticular element, generally referenced 552, constructed and operative in accordance with another embodiment of the disclosed technique. FIG. 9B is a view from the bottom of the lenticular element 552 and the super-pixel 550 of FIG. 9A. FIG. 9C is a view from the side of the lenticular element 552 and the super-pixel 550 of FIG. 9A.

The super-pixel 550 includes four sensor sections, 554, 556, 558 and 560, arranged in a rectangular formation. The lenticular element 552 is shaped like a dome and is basically divided into four sections, each facing a different one of the sensor sections 554, 556, 558 and 560.

The super-pixel 550 and the lenticular element 552 form together, an optical detection unit, which is capable of detecting and distinguishing light which arrives from four different directions. The lenticular element 552 directs a portion of the upper-left side view of the detected object to sensor section 554 and directs a portion of the lower-left side view of the detected object to sensor section 556. In addition, the lenticular element 552 directs a portion of the upper-right side view of the detected object to sensor section 560 and a portion of the lower-right side view of the detected object to sensor section 558.

It is noted that according to a further aspect of the disclosed technique, the four-direction arrangement, which is described in FIGS. 9A, 9B and 9C can be used to logically rotate the image which is provided to the user, without physically rotating the device itself. At first, sensor sections 560 and 558 are used to form the right-side image and sensor sections 554 and 556 are used to form the left-side image. A rotation at an angle of 90° clockwise, is provided by assigning sensor sections 554 and 560, to form the right side image, and assigning sensor sections 556 and 558, to form the left-side image. It is further noted that a rotation in any desired angle can also be performed by means of a linear or other combination of sensor sections, when reconstructing the final images.

Figure 10:
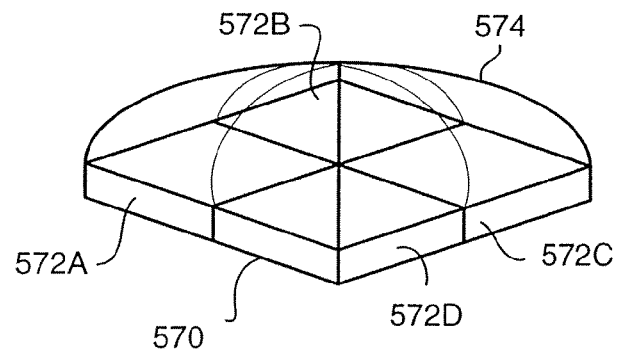
FIG. 10 is a view in perspective of a section of light sensors, and a lenticular element, constructed and operative in accordance with a further embodiment of the disclosed technique.

Reference is now made to FIG. 10, which is a view in perspective of a section of light sensors, generally referenced 570, and a lenticular element, generally referenced 572, constructed and operative in accordance with a further embodiment of the disclosed technique. Lenticular element 572 is extended to cover the entire area of the section of pixels, so as to enhance light transmission thereto.

Figure 11:
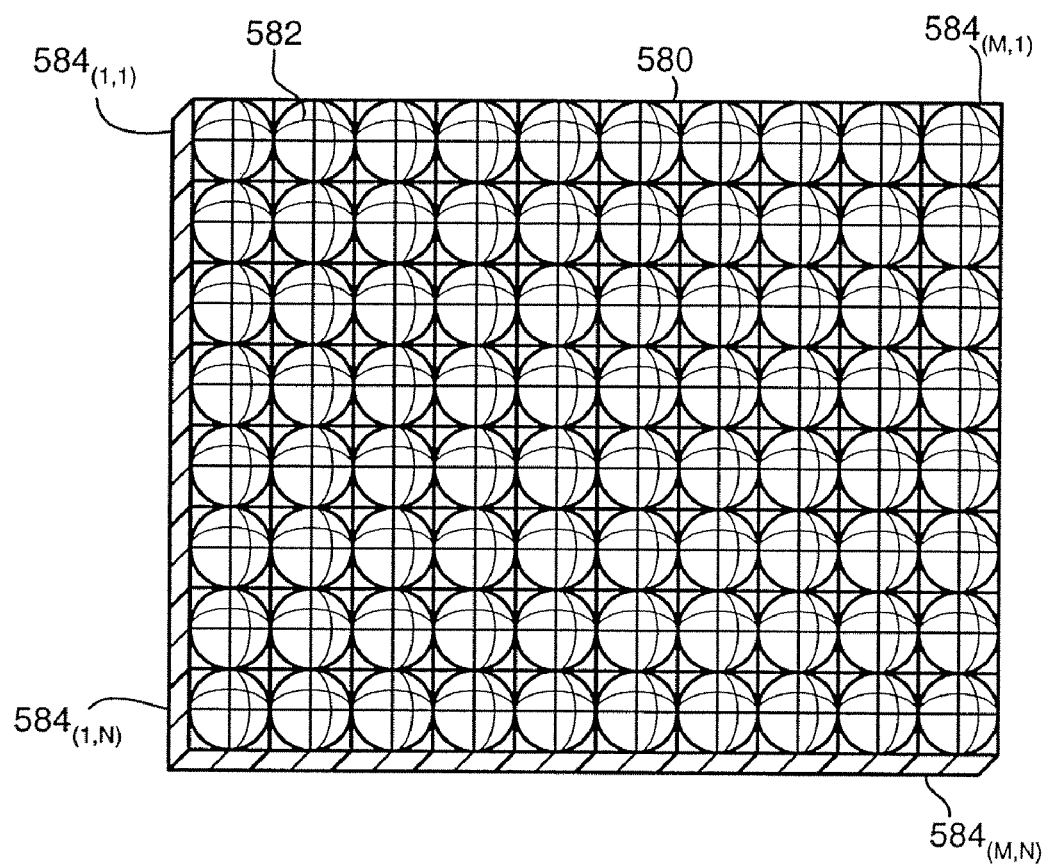
FIG. 11 is a view in perspective of a sensor array and a lenticular lens layer, constructed and operative in accordance with another embodiment of the disclosed technique.

Reference is now made to FIG. 11, which is a view in perspective of a sensor array, generally referenced 580, and a lenticular lens layer, generally referenced 582, constructed and operative in accordance with another embodiment of the disclosed technique. The lenticular lens layer 582 includes a plurality of four direction lenticular elements such as described in FIGS. 9A and 10. The sensor array 580 is logically divided into a plurality of sensor sections, generally referenced $584_{(x,y)}$. For example, the upper left sensor section is referenced $584_{(1,1)}$ and the lower-right sensor section is referenced $584_{(M,N)}$. Each of the sensor sections is located beneath a lenticular element and detects light directed thereby.

Figure 12A:
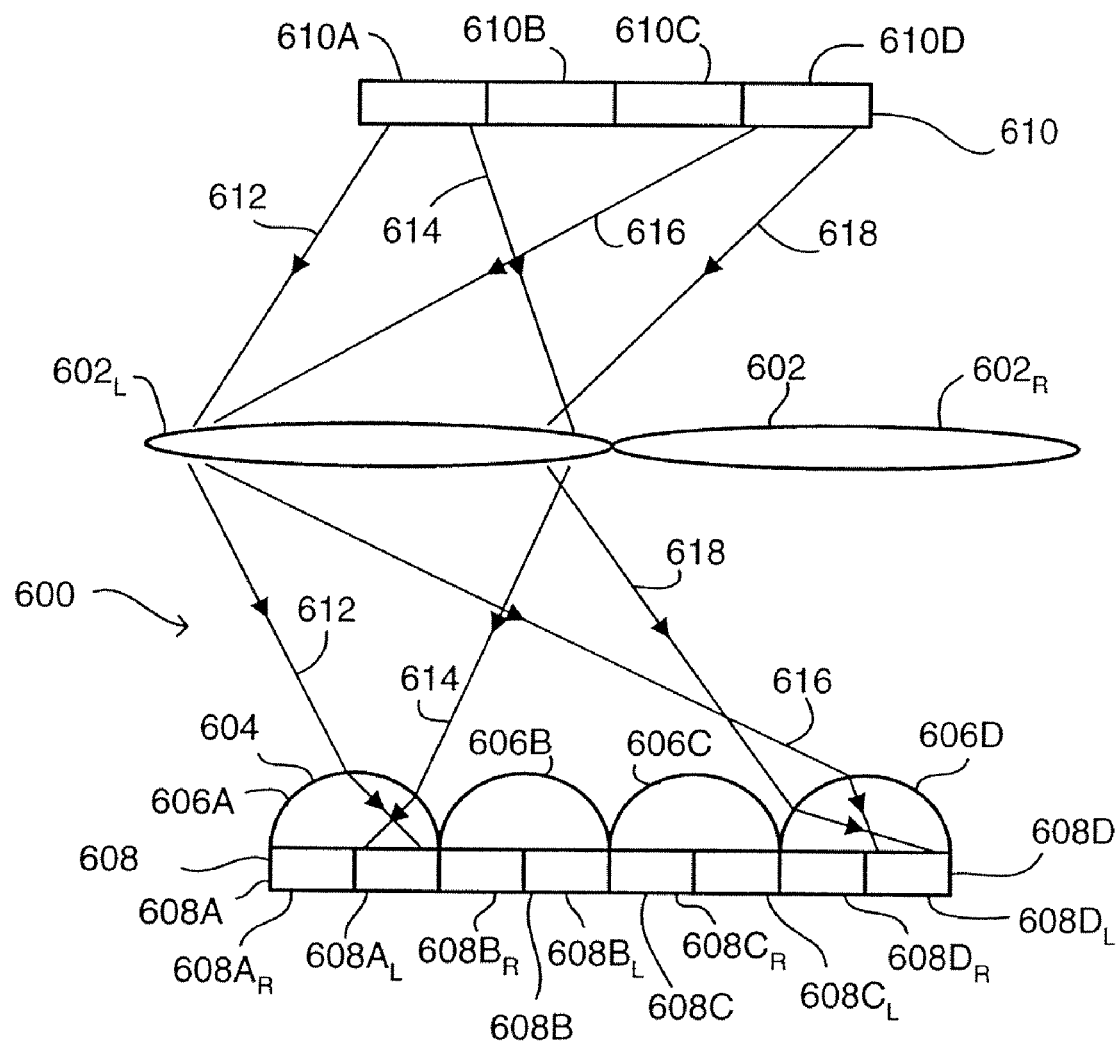
FIG. 12A is a schematic illustration of a detection apparatus, constructed and operative in accordance with a further embodiment of the disclosed technique.
Figure 12B:
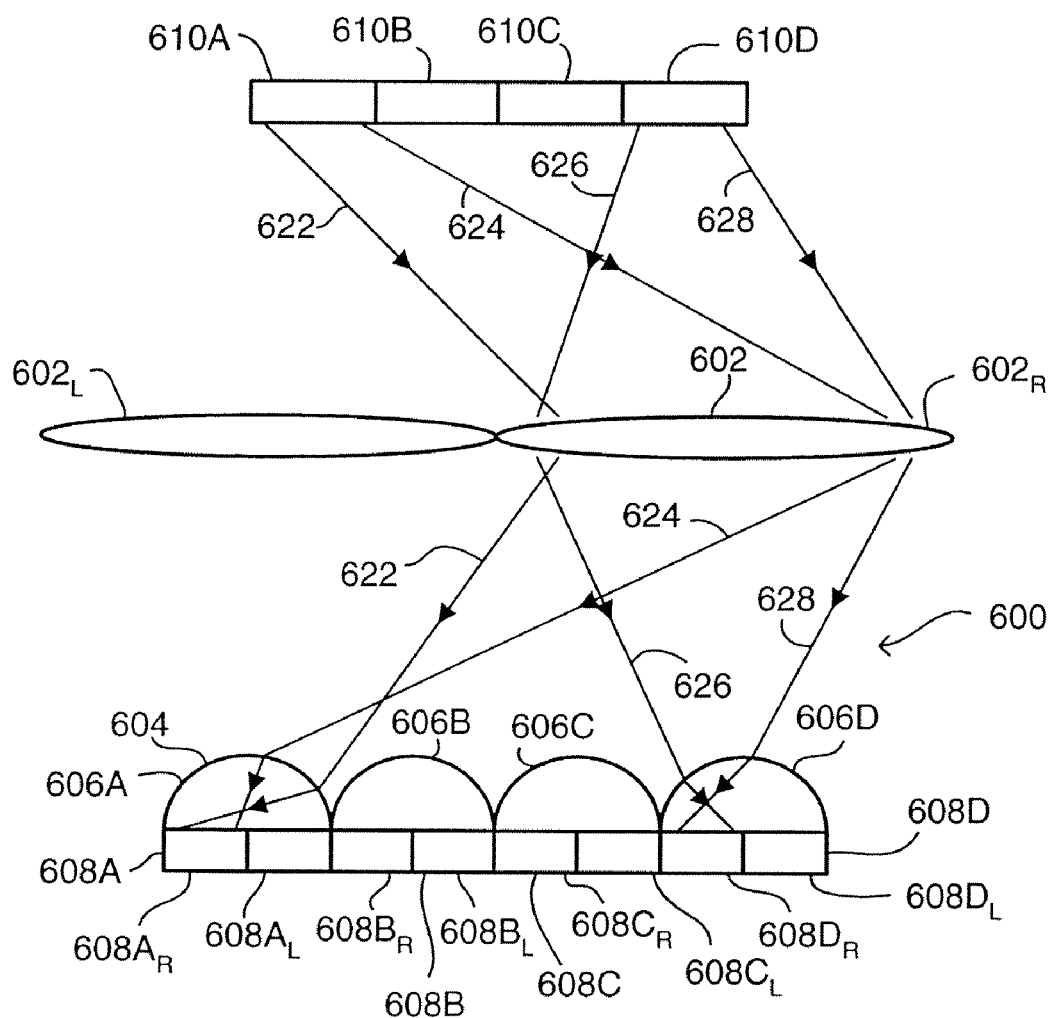
FIG. 12B is another schematic illustration of the detection apparatus of FIG. 12A.

Reference is now made to FIGS. 12A and 12B. FIG. 12A is a schematic illustration of a detection apparatus, generally referenced 600, constructed and operative in accordance with a further embodiment of the disclosed technique. FIG. 12B is another schematic illustration of detection apparatus 600, of FIG. 12A.

Detection apparatus 600 includes an optical assembly 602, a lenticular lens layer 604 and an array of sensors 608. The detection apparatus 600 detects images of an object 610, which includes a plurality of object sections 610A, 610B, 610C and 610D.

Sensor array 608 includes a plurality of super-pixels 608A, 608B, 608C and 608D. Each of these super-pixels is divided into a left-side section and a right-side section. For example, super-pixel 608A includes a left-side section, designated $608A_L$ and a right-side section, designated $608A_R$.

The optical assembly 602 is divided into two optical sections $602_L$ and $602_R$, each directed at transferring an image, which represents a different side view. Optical section $602_R$ transfers an image, which is a view from the right side of object 610. Optical section $602_L$ transfers an image, which is a view from the left side of object 610.

A plurality of light rays 612, 614, 616 and 618 are directed from all sections of the object 610 to the left side of optical assembly 602 (i.e., optical section $602_L$), and from there, are directed to the lenticular lens layer 604. Here, these rays are further directed to the left-side view associated sensor sections, which are sensor sections $608_L$ (i.e., sensor sections $608A_L$, $608B_L$, $608C_L$ and $608D_L$).

With reference to FIG. 12B, a plurality of light rays 622, 624, 626 and 628 are directed from all sections of the object 610 to the right side of optical assembly 602 (i.e., optical section $602_R$), and from there, are directed to the lenticular lens layer 604. Here, these rays are further directed to the right-side view associated sensor sections, which are sensor sections $608A_R$, $608B_R$, $608C_R$ and $608D_R$.

Figure 13:
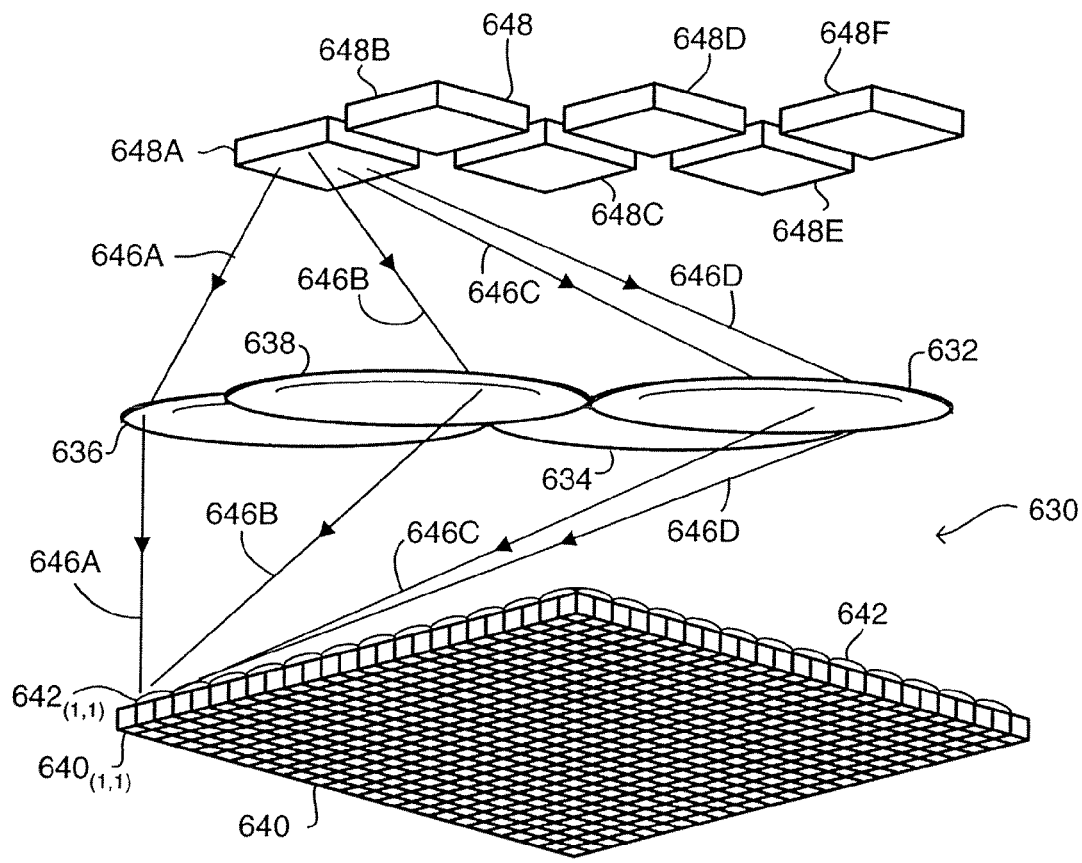
FIG. 13 is a schematic illustration of a detection apparatus, constructed and operative in accordance with another embodiment of the disclosed technique.

Reference is now made to FIG. 13, which is a schematic illustration of a detection apparatus, generally referenced 630, constructed and operative in accordance with another embodiment of the disclosed technique. Detection apparatus 630 includes an optical assembly, which is divided into four sections 632, 634, 636 and 638, a lenticular lens layer 642 and an array of sensors 640. The detection apparatus 630 detects images of an object 648, which includes a plurality of object sections 648A, 648B, 648C, 648D, 648E and 648F. Light rays, which arrive from object 648 to any of the optical sections, are directed to a lenticular element of the lenticular lens layer 642, according to their origin.

In the present example, all of the light rays 646A, 646B, 646C and 646D arrive from object element 648A. Each of these rays is received at a different optical section. Ray 646A is received and directed by optical section 636, ray 646B is received and directed by optical section 638, ray 646C is received and directed by optical section 634 and ray 646D is received and directed by optical section 632. Each of the optical sections directs its respective ray to a specific lenticular element $642_{(1,1)}$, at the right side of the lenticular lens layer 642. The location of lenticular element $642_{(1,1)}$ is respective of the location of the object element 648A. The lenticular element $642_{(1,1)}$ directs each of the rays to predetermined light sensors within its respective super-pixel $640_{(1,1)}$.

In accordance with a further aspect of the disclosed technique, there is provided a reduced size color stereovision detection system, which uses time-multiplexed colored light projections, and respective time-multiplexed frame grabbing.

Figure 14A:
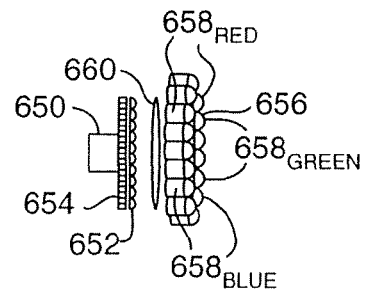
FIG. 14A is a partially schematic partially perspective illustration of a combined illumination and detection device, constructed and operative in accordance with a further embodiment of the disclosed technique.
Figure 14B:
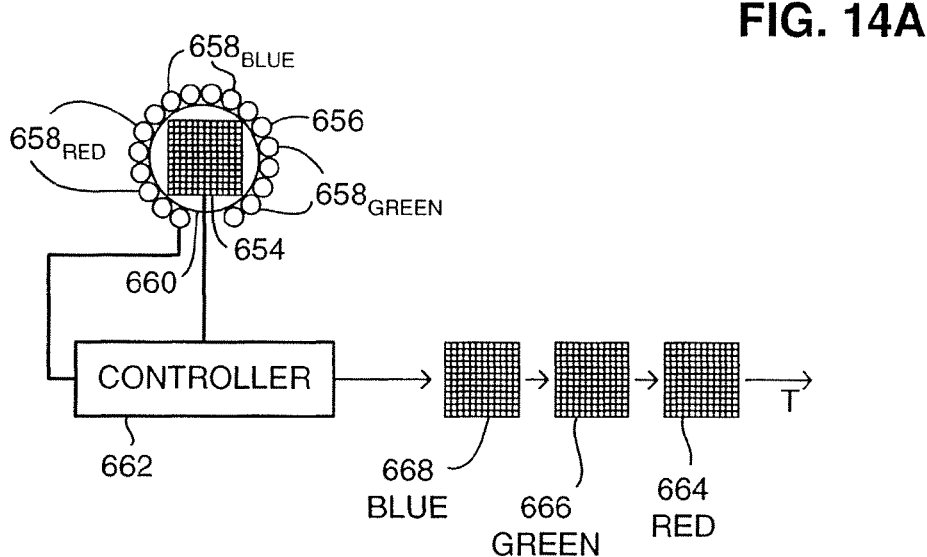
FIG. 14B is a partially schematic partially perspective illustration of the combined illumination and detection device of FIG. 14A, a controller and output frames, constructed and operative in accordance with another embodiment of the disclosed technique.

Reference is now made to FIGS. 14A and 14B. FIG. 14A is a partially schematic, partially perspective illustration of a combined illumination and detection device, generally referenced 650, constructed and operative in accordance with a further embodiment of the disclosed technique. FIG. 14B is a partially schematic, partially perspective illustration of the combined illumination and detection device 650 of FIG. 14A, a controller, generally designated 662, and output frames, constructed and operative in accordance with another embodiment of the disclosed technique.

Device 650 includes a lenticular lens layer 652, a full spectrum sensor array 654, an optical assembly 660 and an illuminating unit 656, surrounding the optical assembly 660. Illuminating unit 656 includes a plurality of illuminating elements, generally referenced 658, each being of a specific predetermined color. Illuminating elements $658_{RED}$ produce generally red light, illuminating elements $658_{GREEN}$ produce generally green light and illuminating elements $658_{BLUE}$ produce generally blue light. It is noted that each of the illuminating elements can be of a specific color (i.e., a specific wavelength), a range of colors (i.e., a range of wavelengths) or alternating colors, for example, a multi-color light emitting diode (LED).

Each group of illuminating elements, which are of the same color, is activated at a different point in time. For example, illuminating elements $658_{RED}$ are activated and shut down first, illuminating elements $658_{GREEN}$ are activated and shut down second and illuminating elements $658_{BLUE}$ are activated and shut down last. Then the illuminating sequence is repeated.

With reference to FIG. 14B, the controller 662 is coupled with the sensor array 654 and to the illuminating unit 656. The sensor array 654 includes full spectrum sensors, which are capable of detecting red, green and blue light, but cannot indicate the wavelength of the detected light. The controller 662 associates the images, which are detected at any particular moment, using the sensor array 654, with the color of the illuminating elements, which were active at that particular moment.

Hence, the first detected frame 664 in an illumination sequence is considered red, since the illuminating elements which were active at that time, were illuminating elements $658_{RED}$. Similarly, the second detected frame 666 in an illumination sequence is considered green, since the illuminating elements, which were active at that time, were illuminating elements $658_{GREEN}$. Finally, the last detected frame 668 in an illumination sequence is considered blue, since the illuminating elements, which were active at that time, were illuminating elements $658_{BLUE}$. It is noted that any other combination of colors is applicable for this and any other aspect of the disclosed technique, such as CYMG, and the like.

Figure 15:
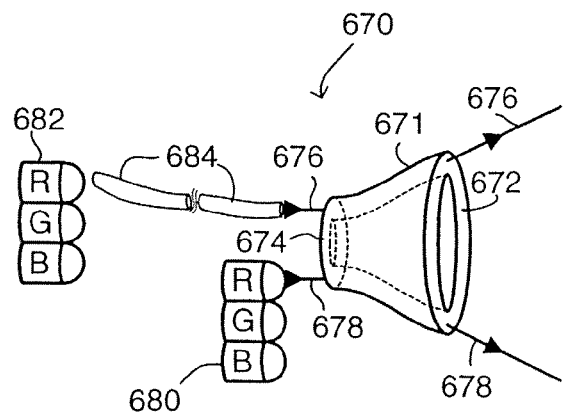
FIG. 15 is an illustration in perspective of a color illumination unit, constructed and operative in accordance with a further embodiment of the disclosed technique.

Reference is now made to FIG. 15, which is an illustration in perspective of a color illumination unit, generally referenced 670, constructed and operative in accordance with a further embodiment of the disclosed technique. Unit 670 includes a light-guiding element 671, which is generally shaped as an open-cut hollow cone, having a narrow section 674 and a wide section 672. A detection head according to the disclosed technique, such as described in FIG. 2 (referenced 202), can be placed within the hollow space of the light-guiding element 671. A multi-color light source 680 can be coupled with the narrow section 674. Light, such as light ray 678, which is emitted from the light source 680, is directed via the light guiding element 671, and is projected through the wide section 672.

According to a further aspect of the disclosed technique, a remote multi-color light source 682 can be coupled with the narrow section 674 via additional light guiding members such as optic-fibers 684. Light, such as light ray 676, which is emitted from the light source 682, is directed via the light guiding members 684 to the narrow section 674. The light-guiding element 671 guides light ray 676, and projects it through the wide section 672. This arrangement is useful when using an external light source, which is to be placed outside the inspected area (for example, outside the body of the patient).

According to a further aspect of the disclosed technique, a full spectrum illumination unit, which produces white light, is combined with a device such as sensor assembly 202 (FIG. 2).

Figure 16:
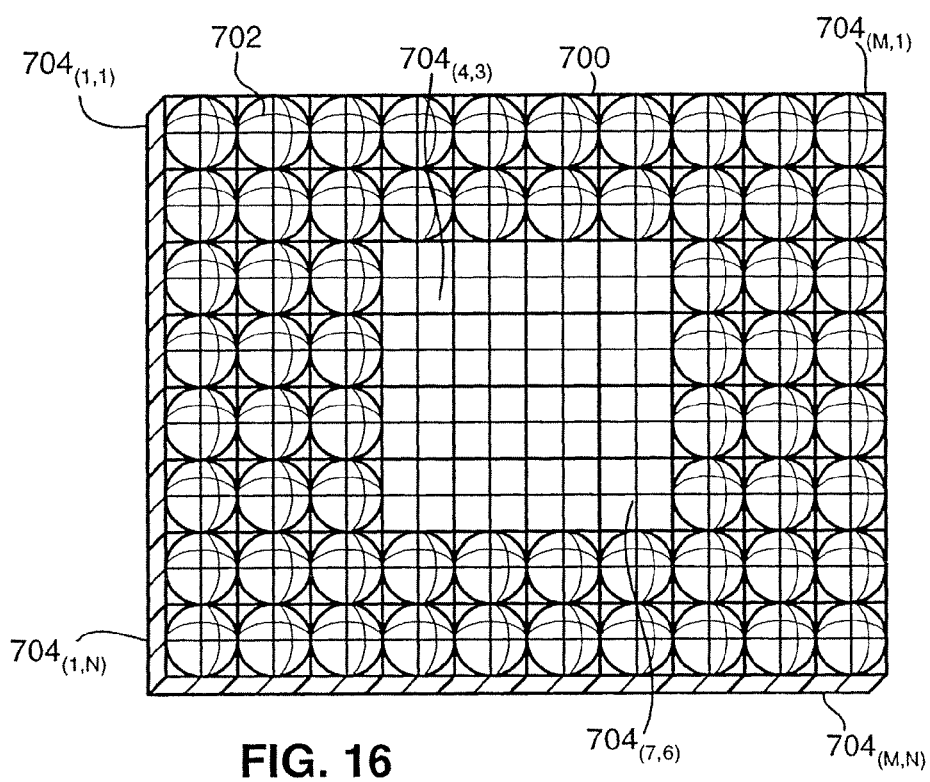
FIG. 16 is a view in perspective of a sensor array and a partial lenticular lens layer, constructed and operative in accordance with another embodiment of the disclosed technique.

Reference is now made to FIG. 16, which is a view in perspective of a sensor array, generally referenced 700, and a partial lenticular lens layer, generally referenced 702, constructed and operative in accordance with another embodiment of the disclosed technique. The partial lenticular lens layer 700 includes a plurality of four direction lenticular elements 702 such as described in FIGS. 9A and 10. The sensor array 700 is logically divided into a plurality of sensor sections, generally referenced $704_{(x,y)}$. For example, the upper left sensor section is referenced $704_{(1,1)}$ and the lower-right sensor section is referenced $704_{(M,N)}$. Some of the sensor sections, in the perimeter, are located beneath lenticular elements and others, such as the sensor sections in the center rectangle, which is defined by sensor sections $704_{(4,3)}$-$704_{(7,6)}$ are not. Accordingly, the sensors which are located at the center rectangle can not be used to provide multi-direction (stereoscopic or quadroscopic) information. Instead, these sensors provide enhanced resolution monoscopic information.

Figure 17:
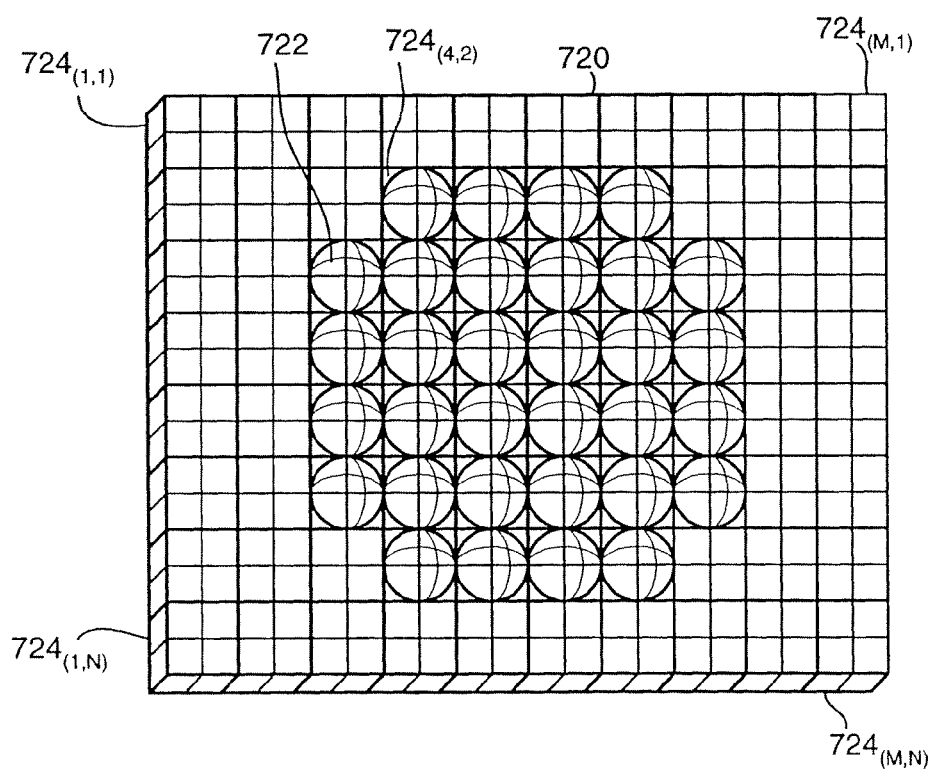
FIG. 17 is a view in perspective of a sensor array and a partial lenticular lens layer, constructed and operative in accordance with a further embodiment of the disclosed technique.

Reference is now made to FIG. 17, which is a view in perspective of a sensor array, generally referenced 720, and a partial lenticular lens layer, generally referenced 722, constructed and operative in accordance with a further embodiment of the disclosed technique. The partial lenticular lens layer 720 includes a plurality of four direction lenticular elements such as described in FIGS. 9A and 10. The sensor array 720 is logically divided into a plurality of sensor sections, generally referenced $724_{(x,y)}$. For example, the upper left sensor section is referenced $724_{(1,1)}$ and the lower-right sensor section is referenced 724(M,N). Here, some of the sensor sections, in the center, (such as sensor section $724_{(4,2)}$) are located beneath lenticular elements and others, such as the sensor sections in the perimeter (such as sensor section $724_{(1,1)}$) are not. Accordingly, the sensors which are located at the center provide multi-direction (stereoscopic or quadroscopic) information and the ones in the perimeter provide enhanced resolution monoscopic information.

Figure 18:
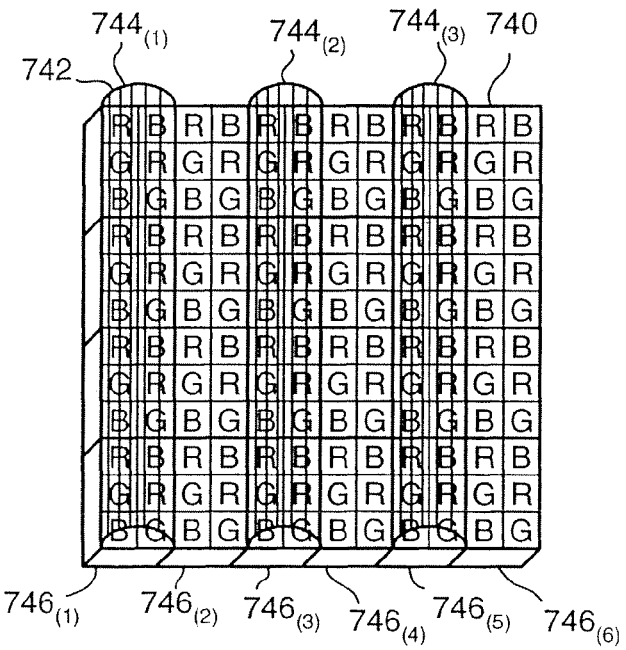
FIG. 18 is a schematic illustration of a sensor array and a partial lenticular lens layer, constructed and operative in accordance with another embodiment of the disclosed technique.

In accordance with a further aspect of the disclosed technique there is provided a partial lenticular lens layer, which includes spaced apart lenticular elements. Reference is now made to FIG. 18, which is a schematic illustration of a sensor array, generally referenced 740, and a partial lenticular lens layer, generally referenced 742, constructed and operative in accordance with another embodiment of the disclosed technique.

The partial lenticular lens layer 742 includes a plurality of lenticular elements designated $744_{(1)}$, $744_{(2)}$ and $744_{(3)}$. Lenticular element $744_{(1)}$ is located over the first two left columns of color sensors, generally referenced $746_{(1)}$, of sensor array 740. Hence, the information received from these first two left columns of color sensors of sensor array 740 contains stereoscopic information. The third and fourth columns of color sensors, generally designated $746_{(2)}$, of sensor array 740 do not have a lenticular element located thereon, and hence, cannot be used to provide stereoscopic information.

Similarly, lenticular element $744_{(2)}$ and $744_{(3)}$ are located over color sensor column pairs, $746_{(3)}$ and $746_{(5)}$, respectively, while color sensor column pairs, $746_{(4)}$ and $746_{(6)}$ are not covered with lenticular elements.

Figure 19:
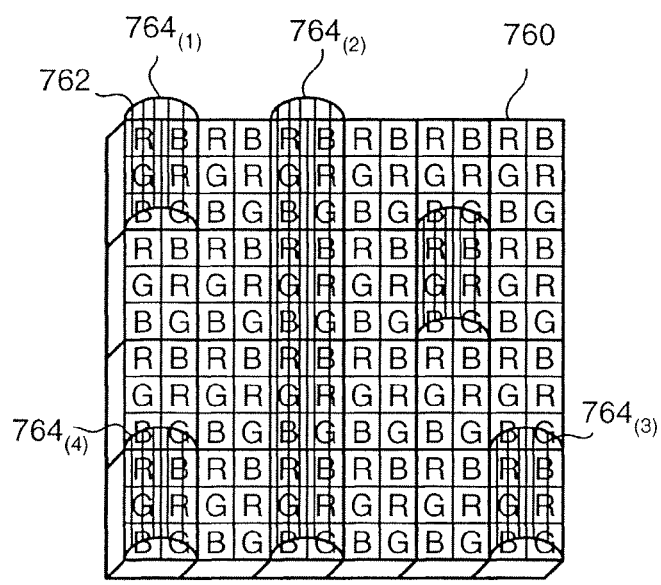
FIG. 19 is a schematic illustration of a sensor array and a partial lenticular lens layer, constructed and operative in accordance with a further embodiment of the disclosed technique.

Reference is now made to FIG. 19, which is a schematic illustration of a sensor array, generally referenced 760, and a partial lenticular lens layer, generally referenced 762, constructed and operative in accordance with another embodiment of the disclosed technique. Lenticular lens layer 762 includes a plurality of lenticular elements, referenced $764_{(1)}$, $764_{(2)}$, $764_{(3)}$ and $764_{(4)}$, being of different sizes and located at random locations over the sensor array 760. It is noted that any structure of partial lenticular lens layer is applicable for the disclosed technique, whereas the associated image processing application has to be configured according to the coverage of that specific lenticular lens layer, and to address covered sensors and uncovered sensors appropriately.

In accordance with a further aspect of the disclosed technique, there is provided a system, which produces a color stereoscopic image. The structure of the stereoscopic device defines at least two viewing angles, through which the detector can detect an image of an object. According to one aspect of the disclosed technique, the stereoscopic device includes an aperture for each viewing angle. Each of the apertures can be opened or shut. The stereoscopic device captures a stereoscopic image, by alternately detecting an image of an object, from each of the viewing angles, (e.g., by opening a different aperture at a time and shutting the rest) through a plurality of apertures, (at least two), each time from a different aperture. The final stereoscopic image can be reconstructed from the images captured with respect to the different viewing angles.

The detection of stereoscopic color image is provided by illuminating the object with a sequence of light beams, each at a different wavelength, and detecting a separate image for each wavelength and aperture combination.

Figure 20A:
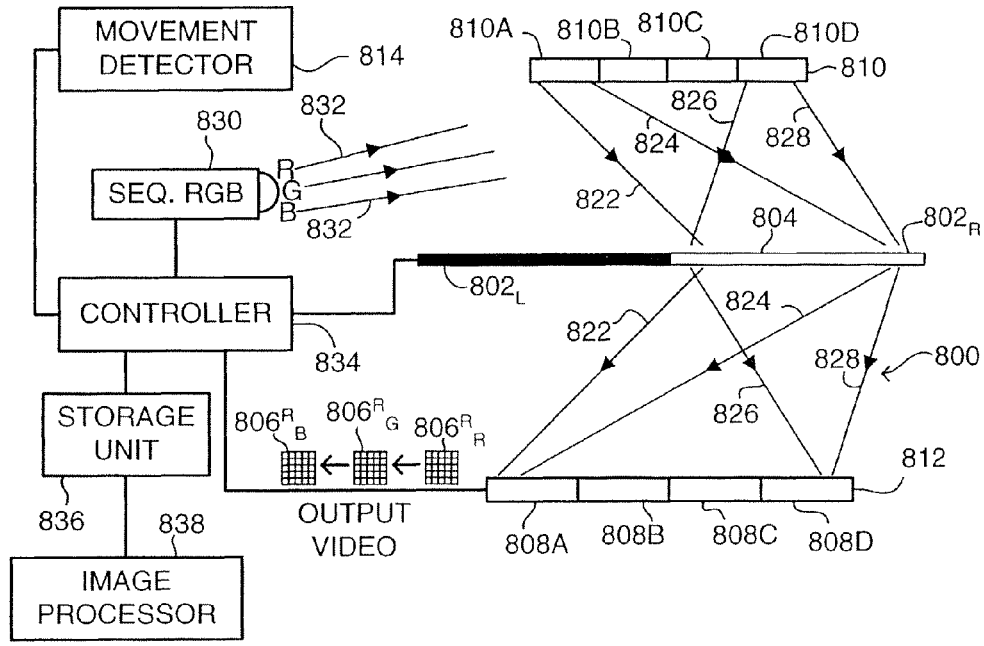
FIG. 20A is a schematic illustration of a system, for producing a color stereoscopic image, in a right side detection mode, constructed and operative in accordance with another embodiment of the disclosed technique.
Figure 20B:
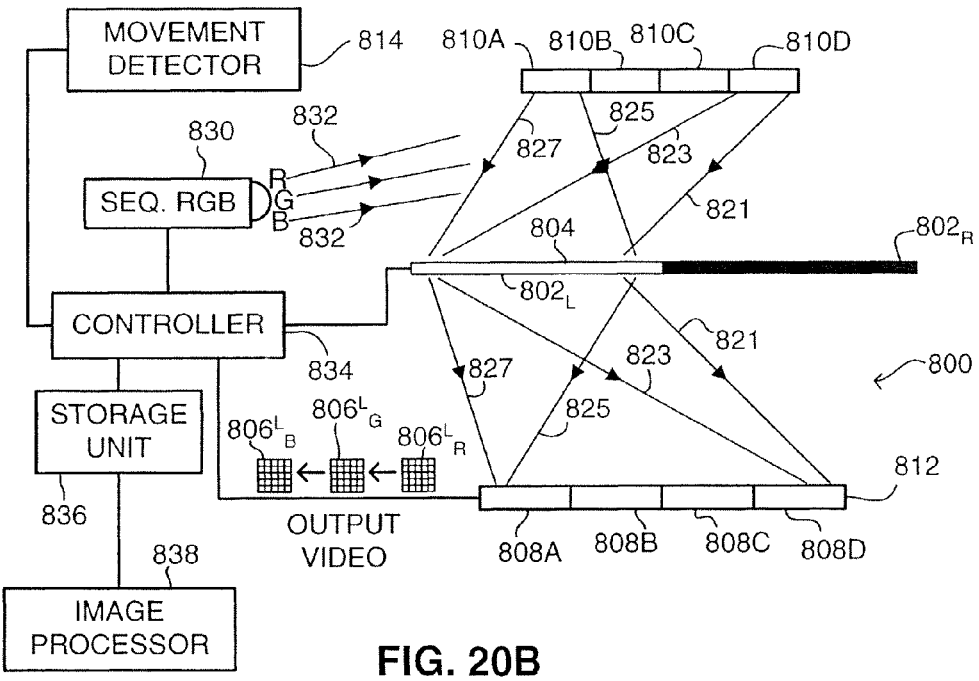
FIG. 20B is an illustration of the system of FIG. 20A, in a left-side detection mode.

Reference is now made to FIGS. 20A and 20B. FIG. 20A is a schematic illustration of a system, generally referenced 800, for producing a color stereoscopic image, in a right side detection mode, constructed and operative in accordance with a further embodiment of the disclosed technique. FIG. 20B is an illustration of the system of FIG. 20A, in a left-side detection mode.

System 800 includes a multiple aperture 804, a controller 834, an image detector 812, a storage unit 836, an image processor 838, a movement detector 814 and an illumination unit 830. The controller 834 is coupled with the multiple aperture 804, the image detector 812, the storage unit 836, movement detector 814 and to the illumination unit 830. The storage unit 836 is further coupled with the image processor 838. The multiple aperture 804 includes a plurality of apertures, generally referenced $802_i$, where each aperture can be activated to be open or closed. It is noted that when an aperture is open it is at least transparent to a predetermined degree to light, and when an aperture is closed, it substantially prevents the travel of light there through. Any type of controllable light valve can be used to construct each of the apertures. Movement detector 814 detects the movement of image detector 812. The detected movement can be a linear displacement, an angular displacement, and the derivatives thereof such as velocity, acceleration, and the like. The operation of system 800, according to data received from movement detector 814, is described herein below in connection with FIGS. 25A, 25B, 25C, 26A, 26B and 26C.

Light valve elements are components, which have an ability to influence light in at least one way. Some of these ways are, for example: scattering, converging, diverging, absorbing, imposing a polarization pattern, influencing a polarization pattern which, for example, may be by rotation of a polarization plane. Other ways to influence light can be by influencing wave length, diverting the direction of a beam, for example by using digital micro-mirror display (also known as DMD) or by using field effect, influencing phase, interference techniques, which either block or transfer a portion of a beam of light, and the like. Activation of light valve elements, which are utilized by the disclosed technique, can be performed either electrically, magnetically or optically. Commonly used light valve elements are liquid crystal based elements, which either rotate or create and enforce a predetermined polarization axis.

In the present example, multiple aperture 804 includes two apertures $802_R$ and $802_L$. The controller 834 further activates the multiple aperture 804, so as to alternately open apertures $802_R$ and $802_L$. In FIG. 20A, aperture $802_R$ is open while aperture $802_L$ is closed and in FIG. 20B, aperture $802_R$ is closed while aperture $802_L$ is open.

Light rays, which reflect from various sections of the object 810, pass through the currently open aperture ($802_R$ in FIG. 20A and $802_L$ in FIG. 20B). Thereby, light rays 822 and 824 arrive from section 810A of object 810, pass through aperture $802_R$, and are detected by detection element 808A, while light rays 826 and 828 arrive from section 810D, pass through aperture $802_R$ and are detected by detection element 808D. Hence, when aperture $802_R$ is open, the system 800 provides a right side view of the object 810.

With reference to FIG. 20B, when aperture $802_L$ is open, light rays 827 and 825 arrive from section 810A, pass through aperture $802_L$, and are detected by detection element 808A, while light rays 821 and 823 arrive from section 810D, pass through aperture $802_L$, and are detected by detection element 808D. Thereby, the system 800 provides a left side view of the object 810.

The illumination unit 830 is a multi-color illumination unit, which can produce light at a plurality of wavelengths. The controller 834 provides a sequence of illumination commands to the illumination unit 830, so as to produce a beam at a different predetermined wavelength, at each given moment. In the present example, the illumination unit is a red-green-blue (RGB) unit, which can produce a red light beam, a green light beam and a blue light beam. It is noted that illumination unit 830 can be replaced with any other multi-color illumination unit, which can produce either visible light, non-visible light or both, at any desired wavelength combination (CYMG and the like).

Furthermore, illumination unit 830 can be a passive unit, where it receives external commands to move from one wavelength to another, or it can be an active unit, which changes wavelength independently and provides an indication of the currently active wavelength to an external controller. Illumination unit 830 of the present example is a passive unit, which enhances the versatility of the system 800, by providing any wavelength sequence on demand.

The image detector 812 includes a plurality of detection elements 808A, 808B, 808C and 808D. In accordance with one aspect of the disclosed technique, image detector 812 is a full range color detector, where each of the detection elements is operative to detect light in a plurality of wavelengths. In accordance with another aspect of the disclosed technique, the image detector 812 is a color segmented detector, where the detection elements are divided into groups, each operative to detect light in a different range of wavelengths. One conventional type of such detectors includes a full range detection array, which is covered by a color filter layer, where each detection element is covered by a different color filter. Accordingly, some of the detection elements are covered with red filters, others are covered with green filters and the rest are covered with blue filters.

The disclosed technique enhances the color resolution of systems, using such color detectors. It will be appreciated by those skilled in the art that a color segment detector of poor quality may exhibit a wavelength (color) overlap between the different detection elements. For example, when the filters are of poor quality, their filtering functions tend to overlap such as the red filter also passes a small amount of either green or blue light. Hence, the detection element behind the red filter, also detects that small amount of green or blue light, but provides an output measurement as a measurement of red light. Hence, the color detector produces an image, which includes incorrect measurements of red light (e.g. more than the actual red light, which arrived at the detector) as result of that overlap. Accordingly, received information of the inspected object is not valid.

In the disclosed technique, the illumination unit 830 produces a sequence of non-overlapping illumination beams at predetermined wavelengths (i.e., red, blue and green). As explained above, the color detector detects an image, which includes incorrect measurements, as a result of the wavelength (color) filtering overlap. Since the illumination unit 830 and the image acquisition process are synchronized, the imaging system can process each of the acquired images, according to the actual light beam color, which was produced therewith. For example, the illumination unit 830 produces blue light illumination beam. At the same time the image detector 812 detects an image, which also includes actual light measurements in detection elements, which are covered with green and red filters, due to the wavelength overlap. The imaging system can discard light measurements, which are received from detection elements, covered with color filters, which are not blue (e.g., red and green).

Such sequenced color illumination of the object, provides enhanced color resolution, for color image detectors of poor quality, and obtains the valid color images of the inspected object. System 800 can further include a stereoscopic display unit (not shown), coupled with controller 834 for displaying a stereoscopic image of object 810.

Figure 21A:
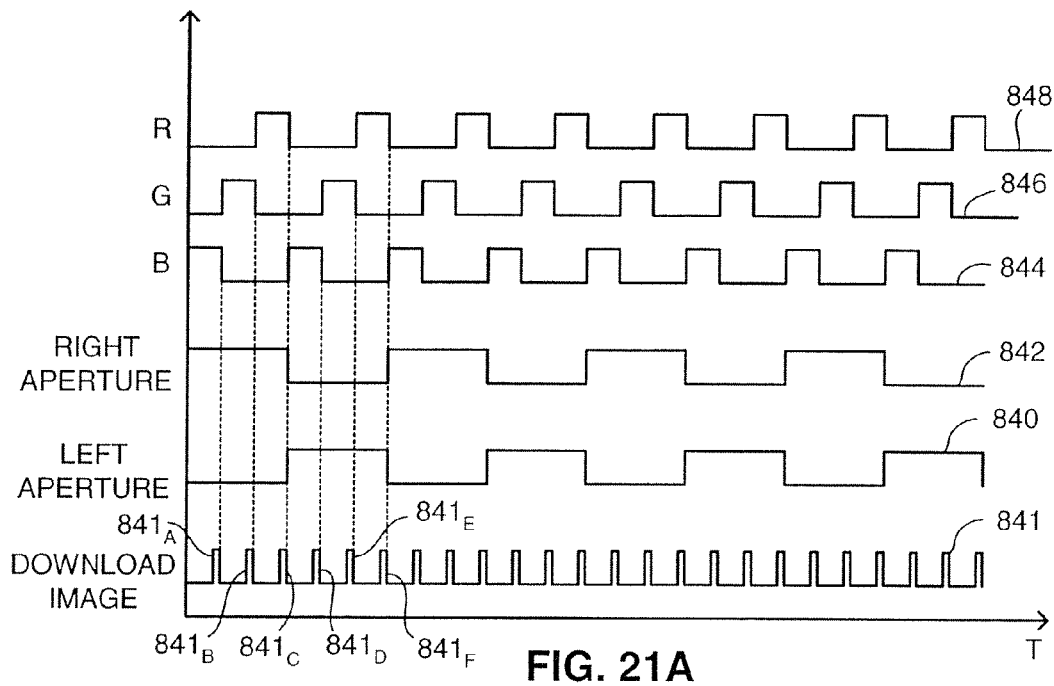
FIG. 21A is a schematic illustration of a timing sequence, in which the controller of the system of FIG. 20A synchronizes the operation of illumination unit, apertures and image detector of that same system.

Reference is further made to FIG. 21A, which is a schematic illustration of a timing sequence, in which controller 834 (FIG. 20A) synchronizes the operation of illumination unit 830, apertures $802_L$ and $802_R$, and image detector 812. Signal 840 represents the timing sequence of the left aperture $802_L$. Signal 842 represents the timing sequence of the right aperture $802_R$. Signal 844 represents the timing sequence of the blue light beam, produced by the illumination unit 830. Signal 846 represents the timing sequence of the green light beam, produced by the illumination unit 830. Signal 848 represents the timing sequence of the red light beam, produced by the illumination unit 830. Signal 841 represents the timing sequence of the image detector 812, where each image is downloaded therefrom.

Timing sequence 841 rises every time any of the rises of sequences 844, 846 and 848 intersect with a rise of either sequence 842 or sequence 840. For example, rise $841_A$ indicates a frame download of a blue light-right aperture combination, rise $841_B$ indicates a frame download of a green light-right aperture combination, and rise $841_C$ indicates a frame download of a red light-right aperture combination. Similarly, rise $841_D$ indicates a frame download of a blue light-left aperture combination, rise $841_E$ indicates a frame download of a green light-left aperture combination and rise $841_F$ indicates a frame download of a red light-left aperture combination.

It is noted that for some light sources, the produced light beams do not cover the full range of visible light. For such light sources, the missing color components can be reconstructed (interpolated) taking into consideration the physiological assumption, that color reflection response as a function of reflected angle, does not change much with angle.

Figure 22:
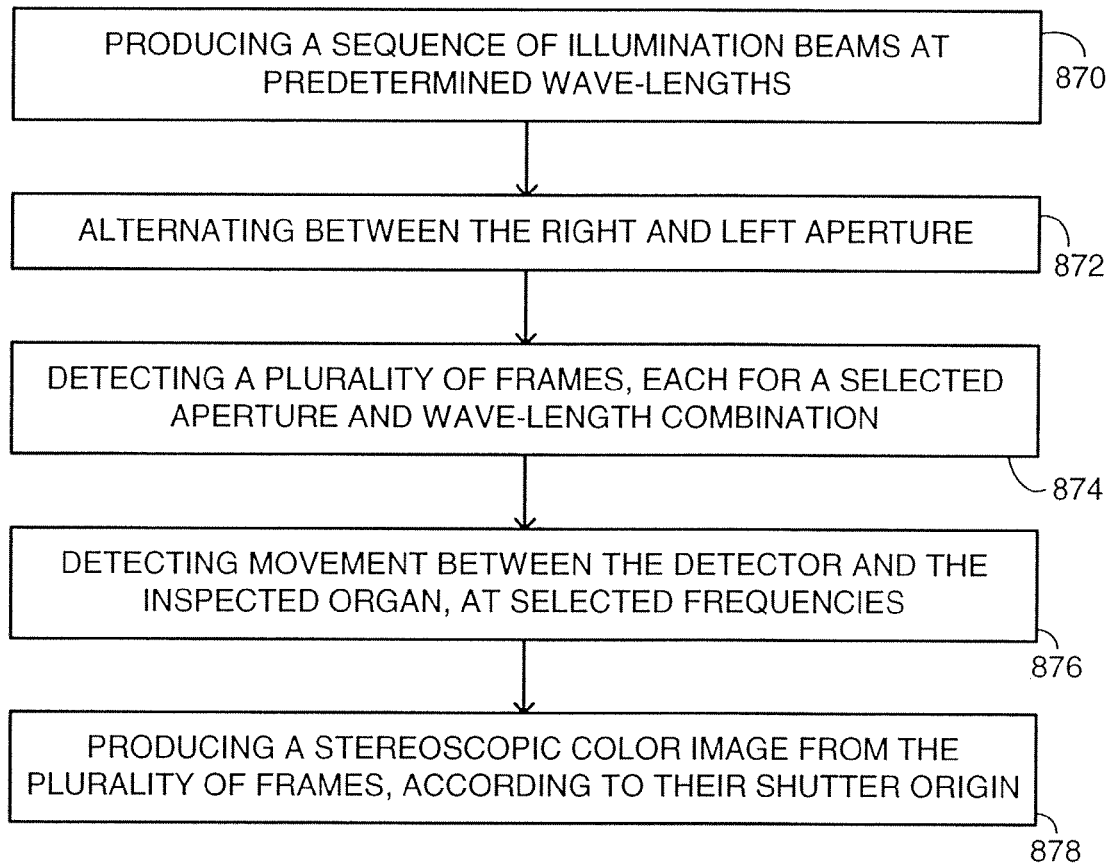
FIG. 22 is a schematic illustration of a method for operating the system of FIGS. 20A and 20B, operative in accordance with a further embodiment of the disclosed technique.

Reference is further made to FIG. 22, which is a schematic illustration of a method for operating system 800 of FIGS. 20A and 20B, operative in accordance with another embodiment of the disclosed technique. In step 870, a sequence of illumination beams at predetermined wavelengths is produced. With reference to FIGS. 20A and 20B, controller 834 provides a sequence of illumination commands to the illumination unit 830, which in turn produces different wavelength light beams, generally referenced 832, at predetermined points in time, towards an object, generally referenced 810.

In step 872 right and left apertures are alternated. Light rays, which reflect from various sections of the object 810, pass through the currently open aperture ($802_R$ in FIG. 20A and $802_L$ in FIG. 20B). With reference to FIGS. 20A and 20B, controller 834 provides a sequence of operating commands to the apertures $802_L$ and $802_R$.

In step 874, a plurality of frames, each for a selected aperture and wavelength combination is detected. Controller 834 operates the image detector 812 so as to detect a plurality of frames, each respective of a selected aperture and wavelength combination.

Light rays 822 and 824 (FIG. 20A) arrive from section 810A of object 810, pass through aperture $802_R$, and are detected by detection element 808A, while light rays 826 and 828 arrive from section 810D, pass through aperture $802_R$ and are detected by detection element 808D. It is noted that in the present example, an imaging element (not shown) is introduced in the vicinity of multiple aperture 804. Hence, when aperture $802_R$ is open, the system 800 provides a right side view of the object 810.

Light rays 827 and 825 (FIG. 20B) arrive from section 810A, pass through aperture $802_L$ and are detected by detection element 808A, while light rays 821 and 823 arrive from section 810D, pass through aperture $802_L$ and are detected by detection element 808D. Hence, when aperture $802_L$ is open, the system 800 provides a left side view of the object 810.

With reference to FIG. 21A, rise $841_A$ provides a right side blue image (reference $806^R_B$ of FIG. 20A), rise $841_B$ provides a right side green image (reference $806^R_G$ of FIG. 20A), and rise $841_C$ provides a right side red image (reference $806^R_R$ of FIG. 20A). Similarly, rise $841_D$ provides a left side blue image (reference $806^L_B$ of FIG. 20B), rise $841_E$ provides a left side green image (reference $806^L_G$ of FIG. 20B), and rise $841_F$ provides a left side red image (reference $806^L_R$ of FIG. 20B). With reference to FIGS. 20A and 20B, image detector 812 detects the plurality of frames, and provides right and left output video for image processing.

In step 876, movement between the detector and the inspected organ, at selected frequencies is detected. This movement can be detected from movement of the endoscope, by means of a movement detector, or by analyzing the detected images, where different color images exhibit different lines, with dramatic color shade changes. This information is utilized in the following step, for spatially correlating between images of different colors.

In step 878 a stereoscopic color image from the plurality of frames, according to their aperture origin is produced. With reference to FIGS. 20A and 20B, the controller 834 stores the detected images in storage unit 836. Image processor 838 retrieves the detected images from the storage unit 836, and constructs color stereoscopic images. Hence, the disclosed technique provides an additional way for detecting a color stereoscopic image, using a single image detector for both sides and all colors.

Figure 21B:
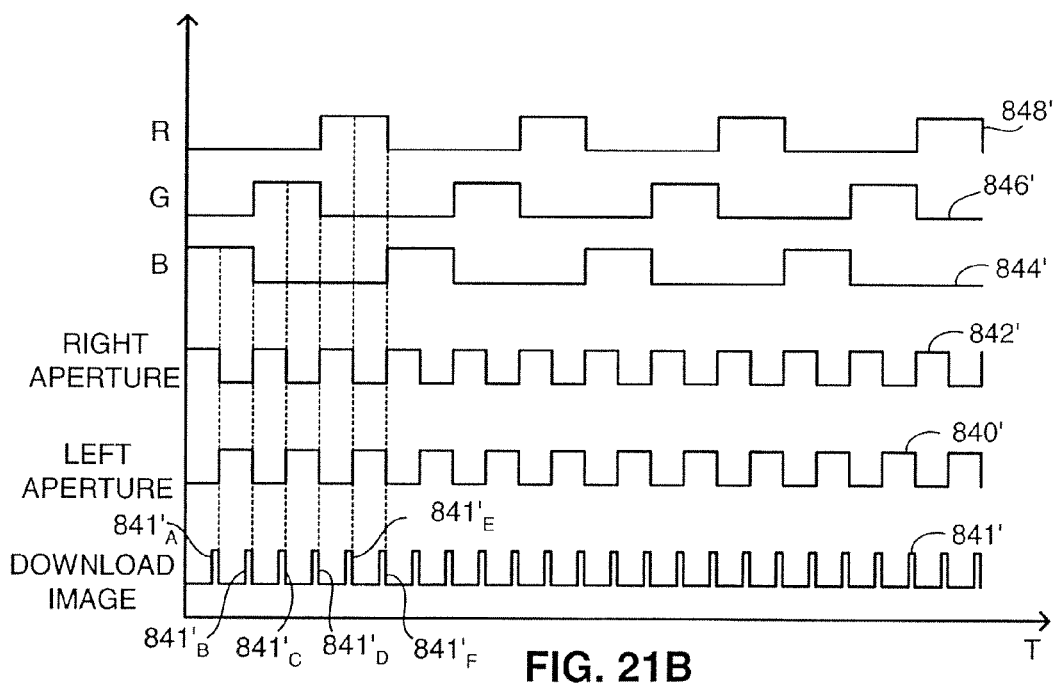
FIG. 21B is a schematic illustration of another timing sequence, in which the controller of FIG. 20A synchronizes the operation of the illumination unit, right and left apertures and the image detector.

Reference is further made to FIG. 21B, which is a schematic illustration of another timing sequence, in which controller 834 (FIG. 20A) synchronizes the operation of illumination unit 830, apertures $802_L$ and $802_R$, and image detector 812. Signal 840' represents the timing sequence of the left aperture $802_L$. Signal 842' represents the timing sequence of the right aperture $802_R$. Signal 844' represents the timing sequence of the blue light beam, produced by the illumination unit 830. Signal 846' represents the timing sequence of the green light beam, produced by the illumination unit 830. Signal 848' represents the timing sequence of the red light beam, produced by the illumination unit 830. Signal 841' represents the timing sequence of the image detector 812, where each image is downloaded therefrom.

Timing sequence 841' rises every time any of the rises of sequence 844', 846' and 848' intersects with a rise of either sequence 842' or sequence 840'. For example, rise $841'_A$ indicates a frame download of a blue light-right aperture combination, rise $841'_B$ indicates a frame download of a blue light-left aperture combination and rise $841'_C$ indicates a frame download of a green light-right aperture combination. Similarly, rise $841'_D$ indicates a frame download of a green light-left aperture combination, rise $841'_E$ indicates a frame download of a red light-right aperture combination and rise $841'_F$ indicates a frame download of a blue light-left aperture combination.

Figure 23:
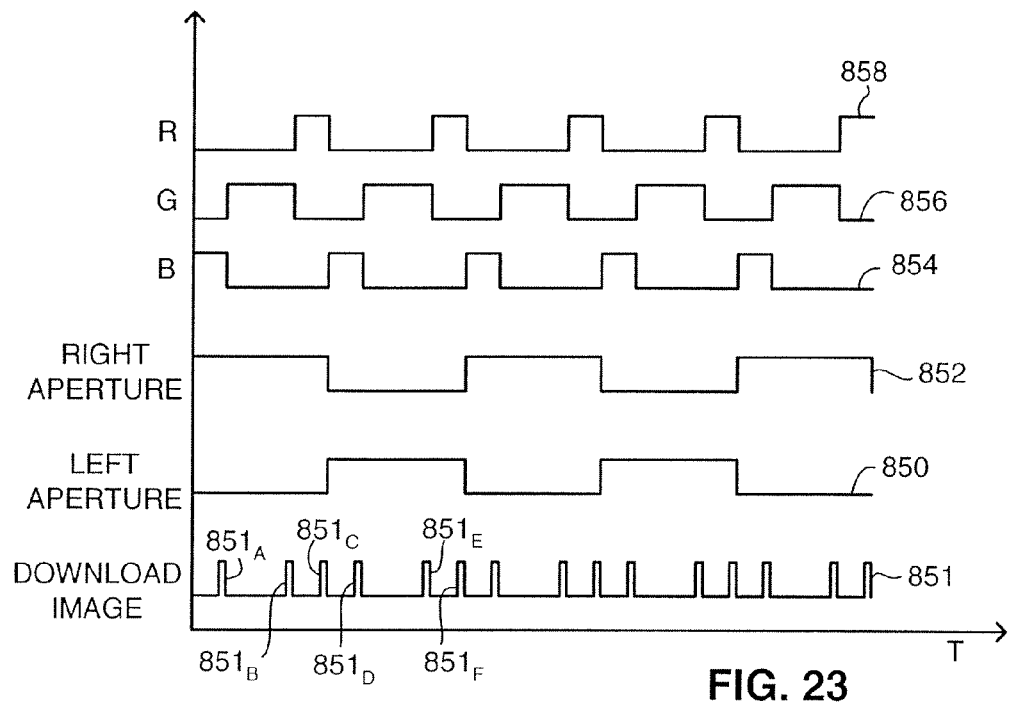
FIG. 23 is a schematic illustration of a timing scheme, for operating the system of FIGS. 20A and 20B, in accordance with another embodiment of the disclosed technique.

Reference is further made to FIG. 23, which is a schematic illustration of a timing scheme, for operating system 800 of FIGS. 20A and 20B, in accordance with a further embodiment of the disclosed technique. Signal 850 represents the timing sequence of the left aperture $802_L$. Signal 852 represents the timing sequence of the right aperture $802_R$. Signal 854 represents the timing sequence of the blue light beam. Signal 856 represents the timing sequence of the green light beam. Signal 858 represents the timing sequence of the red light beam. Signal 851 represents the timing sequence of the image detector 812, where each image is downloaded therefrom. As can be seen in FIG. 23, the timing scheme is asymmetric, where the green light beam is activated for a time period which is twice the time period of either the red light beam or the blue light beam. Signal 851 corresponds to this arrangement and provides a green image download rise (references $851_B$ and $851_E$), after a time period which is twice as long with comparison to red image download rises (references $851_C$ and $851_F$) or blue image download rises (references $851_A$ and $851_D$).

Figure 24:
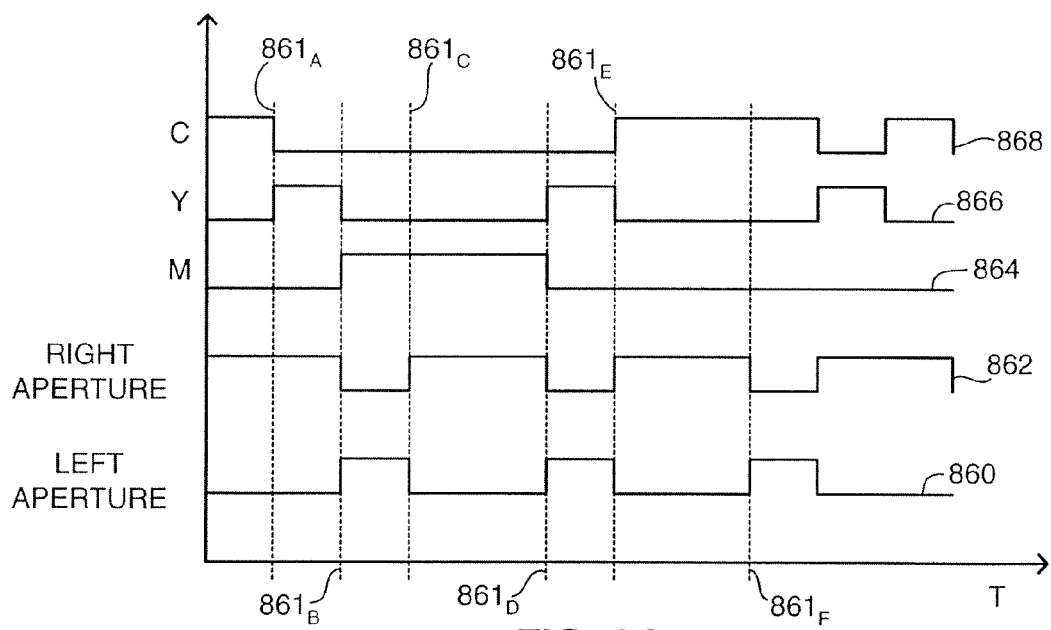
FIG. 24 is a schematic illustration of a timing scheme, for operating the system of FIGS. 20A and 20B, in accordance with a further embodiment of the disclosed technique.

Reference is further made to FIG. 24, which is a schematic illustration of a timing scheme, for operating system 800 of FIGS. 20A and 20B, in accordance with another embodiment of the disclosed technique. Signal 860 represents the timing sequence of the left aperture $802_L$. Signal 862 represents the timing sequence of the right aperture $802_R$. Signal 864 represents the timing sequence of the magenta light beam. Signal 866 represents the timing sequence of the yellow light beam. Signal 868 represents the timing sequence of the cyan light beam. As can be seen in FIG. 24, the timing scheme addresses an alternate wavelength scheme and is also asymmetric.

It is noted that a mechanical multi-wavelength illumination unit such as described in the prior art, can be used for implementing the disclosed technique. However, such a system significantly reduces the capability of the user to control illumination duration, wavelength ratio and detection timing, such as described herein above.

The disclosed technique incorporates even more advanced aspects, which provide automatic image translation correction, based on correlation between the two detected images. When the endoscope is handheld, it is subjected to the vibration of the human hand, which is in the order of 10 Hz, at an angular amplitude of 1 degree. This phenomenon causes a blur of areas, where different colors intersect, and is also known as the "between color field blur" effect. It is noted that any movement between the image detector and the inspected organ can cause this phenomenon, provided it occurs at particular frequencies, defined by the structure and the manner of operation of the system.

With reference to FIGS. 20A and 20B, since the information retrieved from image detector 812 relates to specific colors, then controller 834 can correlate between such single color images to determine the $\Delta X$ and $\Delta Y$ to the subsequent color, and hence compose and produce an un-blurred color image. Due to the vibrations of the human hand, while image detector 812 is substantially stationary relative to object 810, the displayed stereoscopic image of object 810 is blurred. In order to mitigate this problem, and provide a blur-free stereoscopic image of object 810 to the viewer, movement detector 230 (FIG. 2), is incorporated with system 200, and movement detector 814 is incorporated with system 800.

Figure 25C:
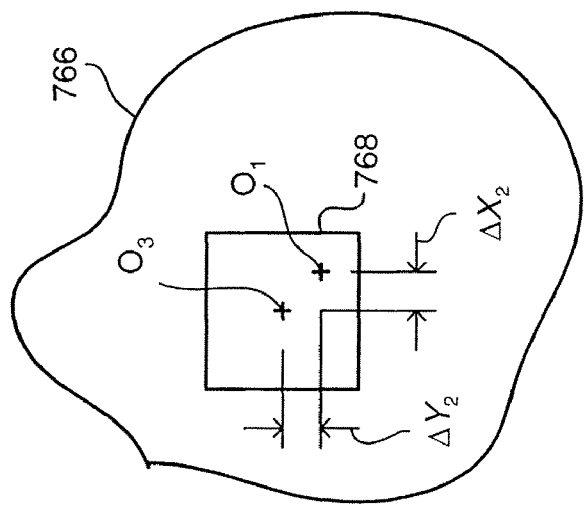
FIG. 25C is a schematic illustration of the object and the sensor assembly of FIG. 25A, when the sensor assembly has moved to another position.
Figure 25B:
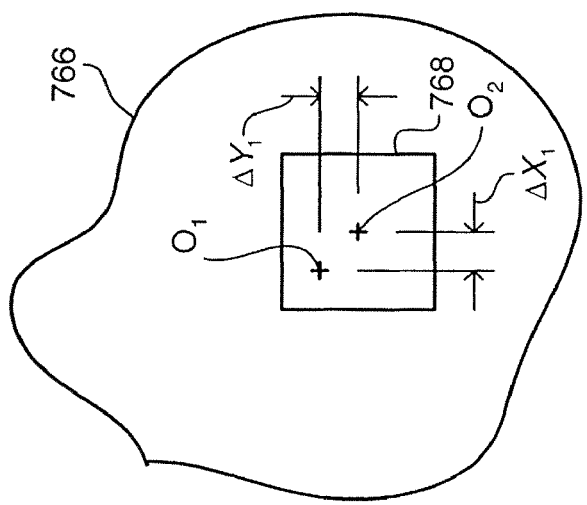
FIG. 25B is a schematic illustration of the object and the sensor assembly of FIG. 25A, when the sensor assembly has moved to a new position.
Figure 25A:
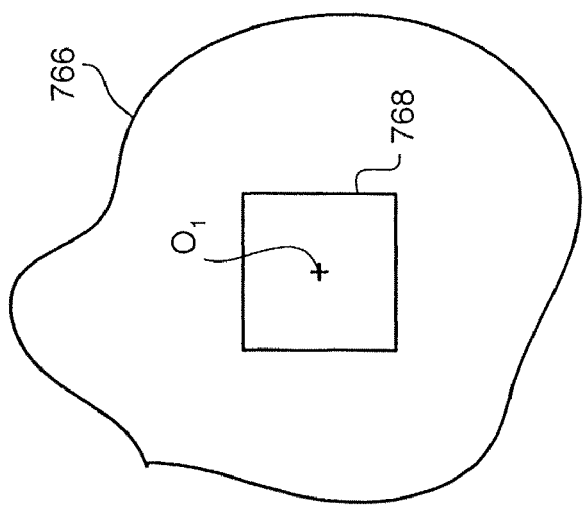
FIG. 25A is a schematic illustration of an object and a sensor assembly, when the sensor assembly is located at an initial position with respect to the object.
Figure 26A:
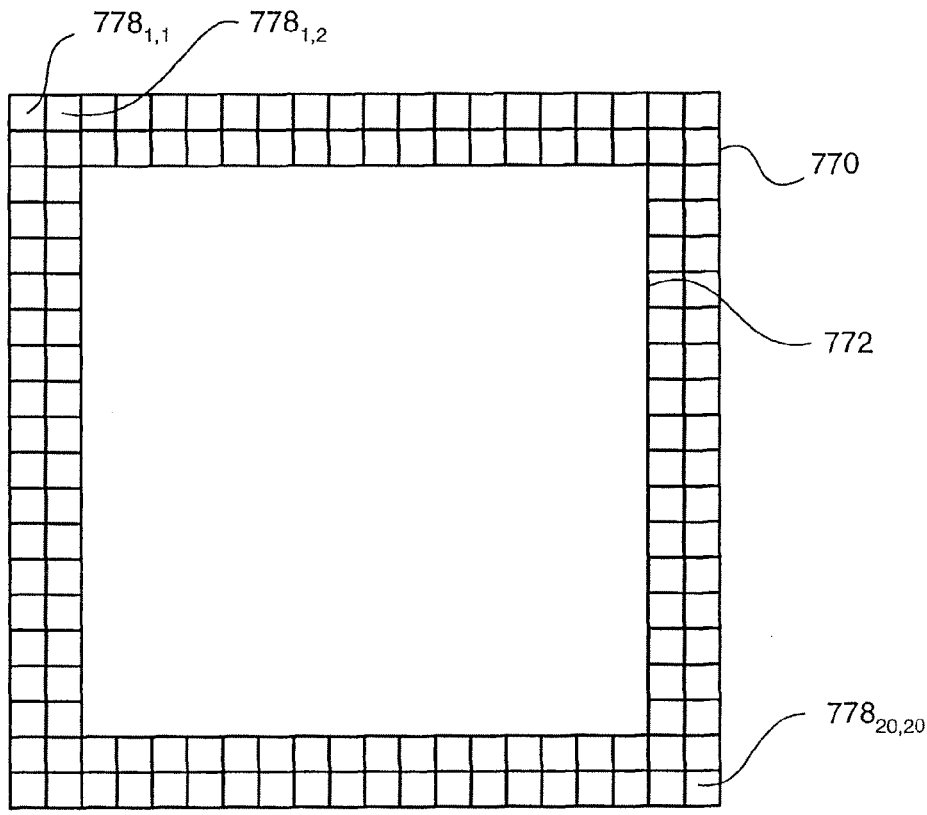
FIG. 26A is a schematic illustration of a detected image, as detected by sensor assembly of FIG. 25A, and a respective displayed image, in accordance with a further embodiment of the disclosed technique.
Figure 26B:
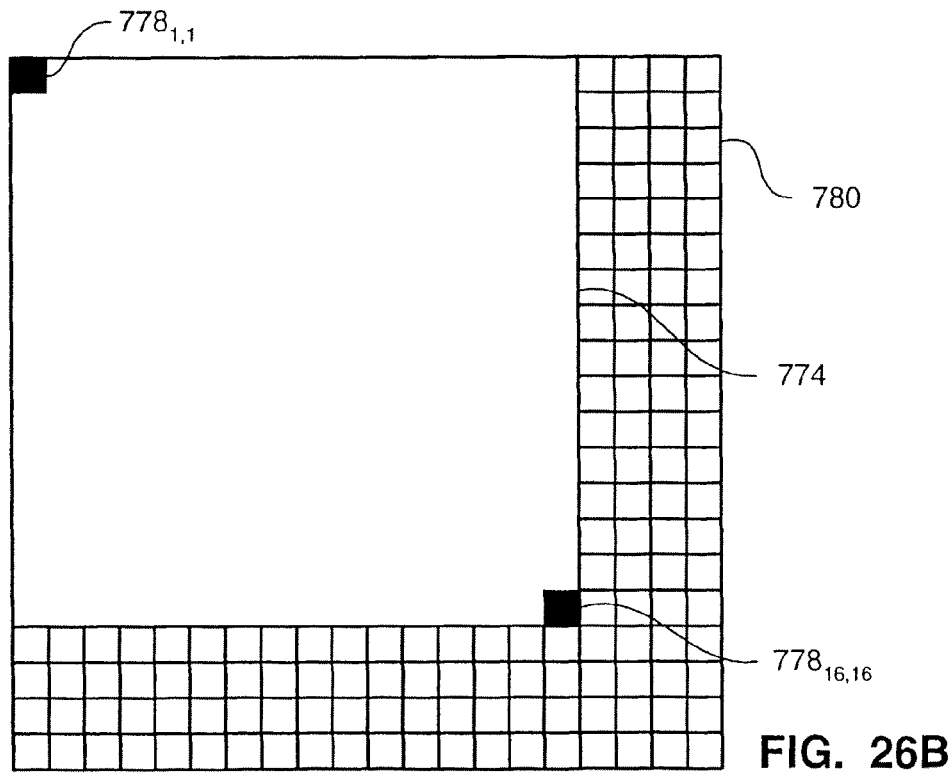
FIG. 26B is a schematic illustration of a detected image, as detected by sensor assembly of FIG. 25B, and a respective displayed image.
Figure 26C:
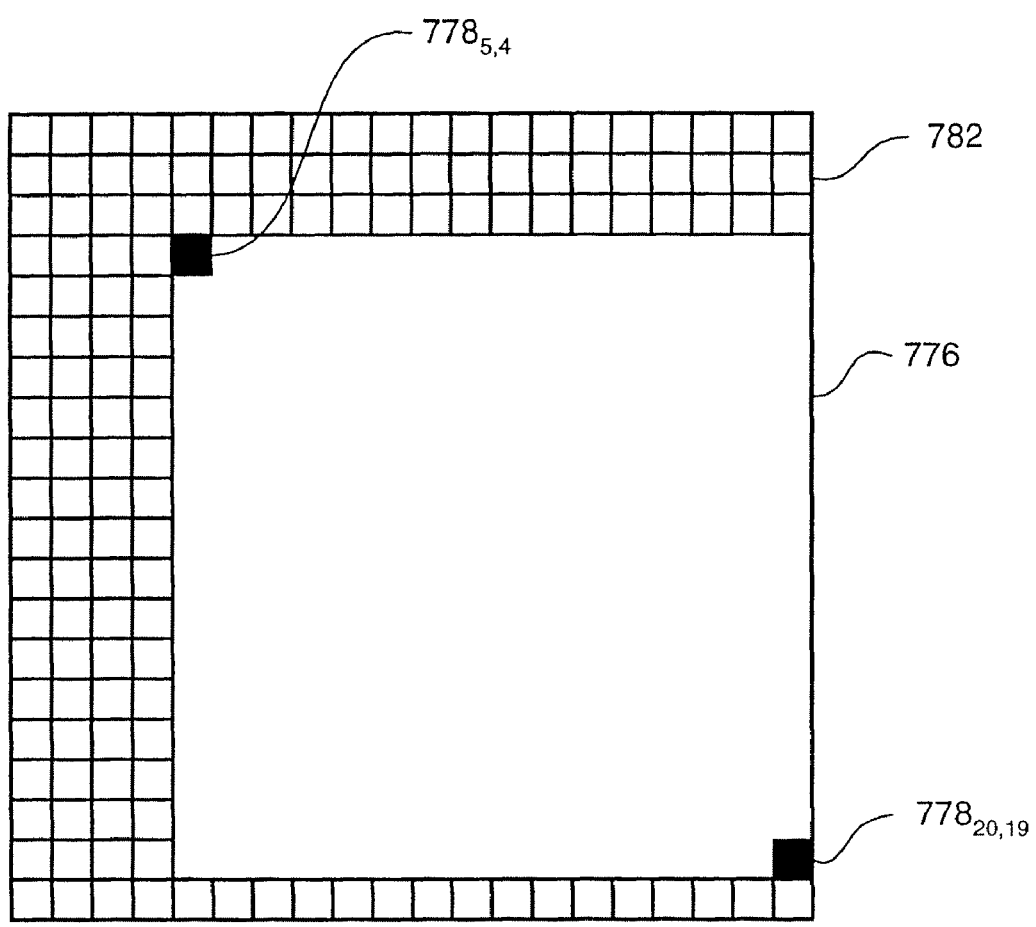
FIG. 26C is a schematic illustration of a detected image, as detected by the sensor assembly of FIG. 25C, and a respective displayed image.

Reference is now made to FIGS. 25A, 25B, 25C, 26A, 26B and 26C and again to FIG. 2. FIG. 25A is a schematic illustration of an object, generally referenced 766, and a sensor assembly generally referenced 768, when the sensor assembly is located at an initial position with respect to the object. FIG. 25B is a schematic illustration of the object and the sensor assembly of FIG. 25A, when the sensor assembly has moved to a new position. FIG. 25C is a schematic illustration of the object and the sensor assembly of FIG. 25A, when the sensor assembly has moved to another position. FIG. 26A is a schematic illustration of a detected image, generally referenced 770, as detected by sensor assembly of FIG. 25A, and a respective displayed image, generally referenced 772, in accordance with a further embodiment of the disclosed technique. FIG. 26B is a schematic illustration of a detected image, generally referenced 780, as detected by sensor assembly of FIG. 25B, and a respective displayed image, generally referenced 774. FIG. 26C is a schematic illustration of a detected image, generally referenced 782, as detected by the sensor assembly of FIG. 25C, and a respective displayed image, generally referenced 776.

The foregoing description relates to one aspect of the disclosed technique, in which a stereoscopic image of an object is captured by a sensor array through a lenticular lens layer (i.e., each captured image includes all the primary colors of the color palette, such as RGB, CYMG, and the like). It is noted that the movement is determined such that it has a constant average (e.g., vibrating about a certain point).

With reference to FIGS. 25A and 26A, the center of sensor assembly 768 is located at a point $O_1$ relative to object 766. Sensor assembly 768 detects detected image 770 (FIG. 26A) of object 766, where the detected image 770 is composed for example, of four hundred pixels (i.e., a 20×20 matrix). Each pixel is designated by $P_{m,n}$ where m is the row and n is the column of detected image 770. For example, pixel $778_{1,1}$ is located in the first row and the first column of detected image 770, pixel $778_{1,2}$ is located in the first row and the second column, and pixel $778_{20,20}$ is located in row twenty and column twenty. Processor 208 selects pixels $778_{3,3}$ through $778_{18,18}$ (i.e., a total of 16×16=256 pixels) to display the sub-matrix 772 on stereoscopic display 214 (FIG. 2), while the center of sensor assembly 768 is located at point $O_1$.

With reference to FIGS. 25B and 26B, due to the vibrations of the human hand, the center of sensor assembly 768 has moved to a point $O_2$ relative to object 766. Point $O_2$ is located a distance $\Delta X_1$ to the right of point $O_1$ and a distance $\Delta Y_1$ below point $O_1$. In this case the length of $\Delta X_1$ is equal to the horizontal width of two pixels of detected image 780, and the length $\Delta Y_1$ is equal to the vertical height of minus two pixels of detected image 780. Movement detector 230 detects the movement of sensor assembly 768 from point $O_1$ to point $O_2$, and sends a signal respective of this movement, to processor 208.

With reference to FIG. 26B, the image of the object section that was captured by sub-matrix 772, is now captured by a sub-matrix 774, which is shifted two pixels up and two pixels to the left. Hence, displaying sub-matrix 774, compensates for the movement of sensor assembly 768. For this purpose, processor 208 selects pixels $778_{1,1}$ through $778_{16,16}$ of detected image 780, for sub-matrix 774. Despite the movement of sensor assembly 768, the images of sub-matrices 772 and 774 are substantially of the same area, and therefore the user does not realize that sensor assembly 768 has moved from point $O_1$ to point $O_2$.

With reference to FIGS. 25C and 26C, the center of sensor assembly 768 has moved from point $O_1$ to a point $O_3$ relative to object 766. Point $O_3$ is located a distance $\Delta X_2$ to the left of point $O_1$ and a distance $\Delta Y_2$ above point $O_1$. In this case the length of $\Delta X_2$ is equal to the horizontal of minus two pixels of detected image 782, and the length $\Delta Y_2$ is equal to the vertical height of one pixel of detected image 782. Movement detector 230 detects the movement of sensor assembly 768 from point $O_1$ to point $O_3$, and sends a signal respective of this movement, to processor 208.

With reference to FIG. 26C, the image of the object section that was captured by sub-matrix 772, is now captured by a sub-matrix 776, which is shifted one pixel up and two pixels to the left. Hence, displaying sub-matrix 774, compensates for the movement of sensor assembly 768 two pixels to the left and one pixel up. For this purpose, processor 208 selects pixels $778_{5,4}$ through $778_{20,19}$ of detected image 782, for sub-matrix 776. Despite the movement of sensor assembly 768, the images of displayed images 772 and 776 are identical, and therefore the user does not realize that sensor assembly 768 has moved from point $O_1$ to point $O_3$. Therefore, by incorporating movement detector 230 with sensor assembly 768, the viewer views a blur-free stereoscopic color image of object 766, despite the vibrations of sensor assembly 768 caused by the human hand.

It is noted that processor 208 processes the detected images 780 and 782, if the dimensions $\Delta X_1$, $\Delta X_2$, $\Delta Y_1$ and $\Delta Y_2$ are of the order of A, the amplitude of vibrations of the human hand and in the appropriate frequency. In general, processor 208 performs the compensation process, between a plurality of captured images, as long as the detected movement, is maintained about a certain average point ($X_{AVERAGE}$, $Y_{AVERAGE}$). When one of the average values $X_{AVERAGE}$ and $Y_{AVERAGE}$ changes, then processor 208 initiates a new compensation process around the updated average point, accordingly.

Figure 25F:
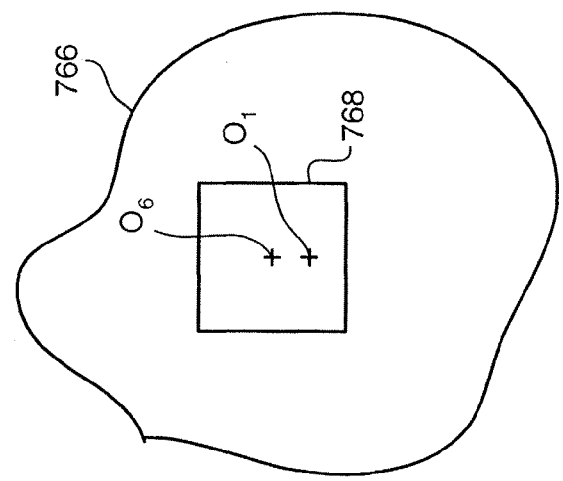
FIG. 25F is a schematic illustration of the object and the sensor assembly of FIG. 25A, when the sensor assembly has moved to a further new position.
Figure 25E:
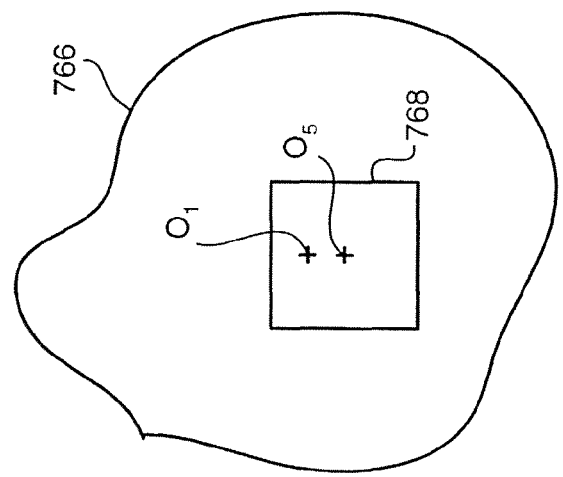
FIG. 25E is a schematic illustration of the object and the sensor assembly of FIG. 25A, when the sensor assembly has moved to another new position.
Figure 25D:
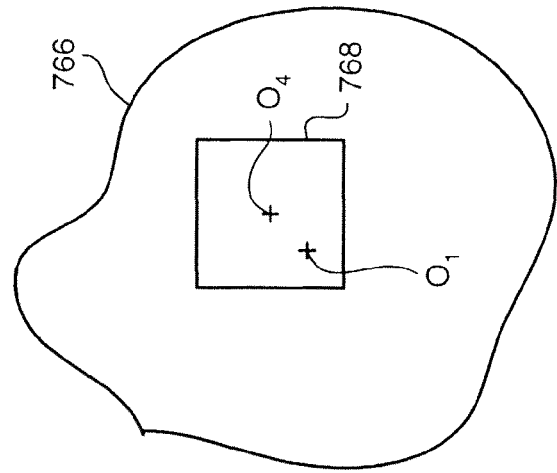
FIG. 25D is a schematic illustration of the object and the sensor assembly of FIG. 25A, when the sensor assembly has moved to a further new position.
Figure 27C:
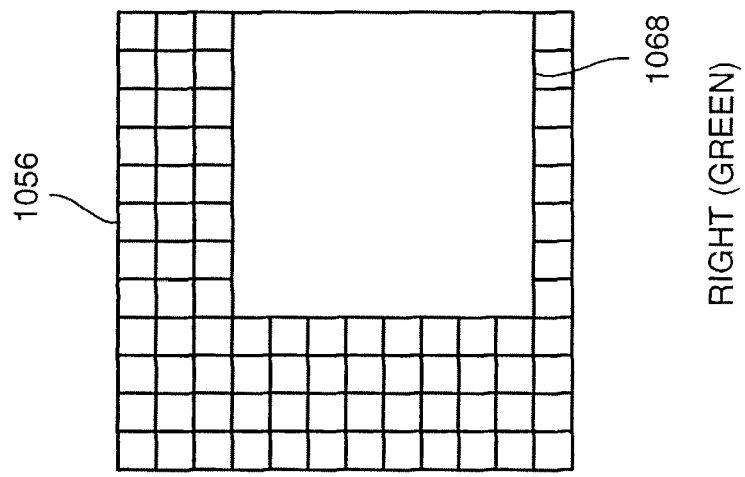
FIG. 27C is a schematic illustration of a sub-matrix, when the sensor assembly is at a location illustrated in FIG. 25C.
Figure 27B:
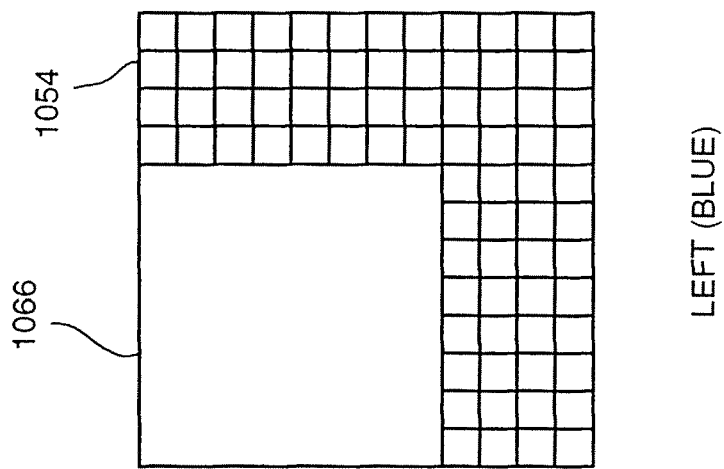
FIG. 27B is a schematic illustration of a sub-matrix, when the sensor assembly is at a location illustrated in FIG. 25B.
Figure 27A:
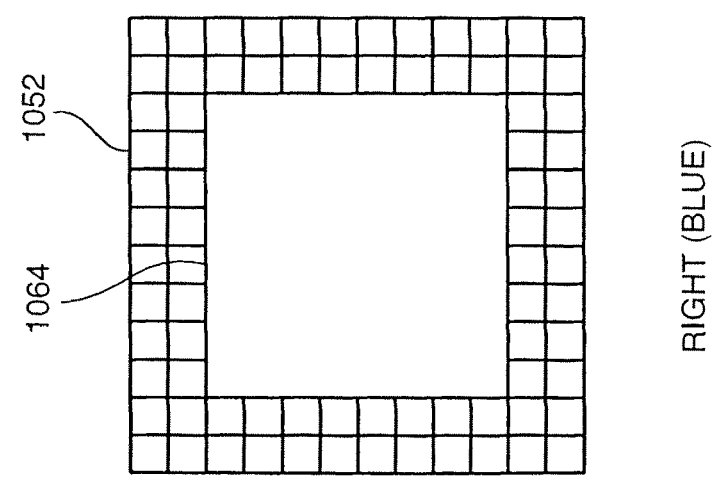
FIG. 27A is a schematic illustration of a sub-matrix, in accordance with another embodiment of the disclosed technique, when the sensor assembly is at a location illustrated in FIG. 25A.
Figure 27F:
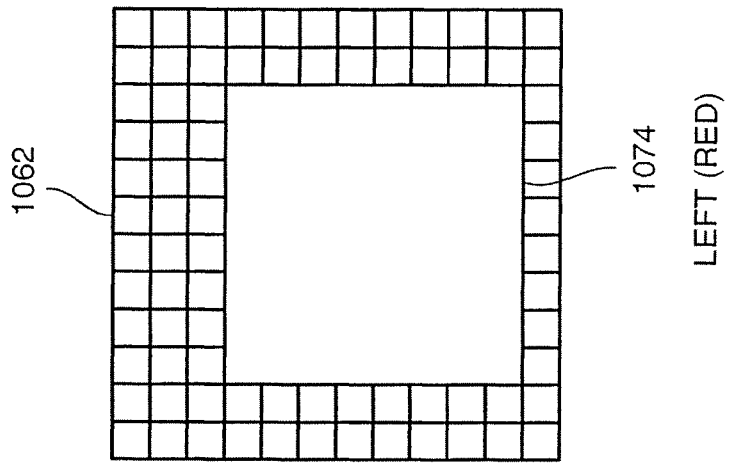
FIG. 27F is a schematic illustration of a sub-matrix, when the sensor assembly is at a location illustrated in FIG. 25F.
Figure 27E:
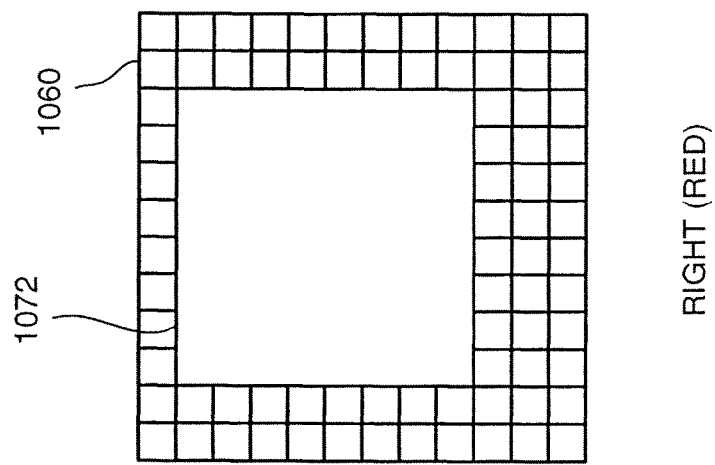
FIG. 27E is a schematic illustration of a sub-matrix, when the sensor assembly is at a location illustrated in FIG. 25E.
Figure 27D:
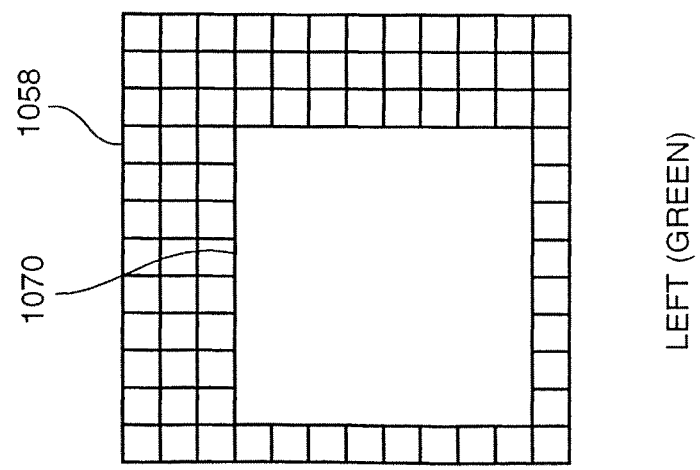
FIG. 27D is a schematic illustration of a sub-matrix, when the sensor assembly is at a location illustrated in FIG. 25D.

Reference is now made to FIGS. 25D, 25E, 25F, 27A, 27B, 27C, 27D, 27E, 27F and again to FIGS. 20A, 20B, 25A, 25B and 25C. FIG. 25D is a schematic illustration of the object and the sensor assembly of FIG. 25A, when the sensor assembly has moved to a further new position. FIG. 25E is a schematic illustration of the object and the sensor assembly of FIG. 25A, when the sensor assembly has moved to another new position. FIG. 25F is a schematic illustration of the object and the sensor assembly of FIG. 25A, when the sensor assembly has moved to a further new position. FIG. 27A is a schematic illustration of a sub-matrix, generally referenced 1064, in accordance with another embodiment of the disclosed technique, when the sensor assembly is at a location illustrated in FIG. 25A. FIG. 27B is a schematic illustration of a sub-matrix, generally referenced 1066, when the sensor assembly is at a location illustrated in FIG. 25B. FIG. 27C is a schematic illustration of a sub-matrix, generally referenced 1068, when the sensor assembly is at a location illustrated in FIG. 25C. FIG. 27D is a schematic illustration of a sub-matrix, generally referenced 1070, when the sensor assembly is at a location illustrated in FIG. 25D. FIG. 27E is a schematic illustration of a sub-matrix, generally referenced 1072, when the sensor assembly is at a location illustrated in FIG. 25E. FIG. 27F is a schematic illustration of a sub-matrix, generally referenced 1074, when the sensor assembly is at a location illustrated in FIG. 25F.

Image processor 838 (FIG. 20A), selects each of sub-matrices 1064, 1066 and 1068 from detected images 1052, 1054 and 1056, respectively, as described herein above in connection with FIGS. 26A, 26B and 26C. Analogously, image processor 838 selects each of sub-matrices 1070, 1072 and 1074 from detected images 1058, 1060 and 1062, respectively, when the center of sensor assembly 768 is directed to each of the points $O_4$, $O_5$, and $O_6$, respectively. For example, when the center of sensor assembly 768 is directed to point $O_4$, which is located to the right and above point $O_1$, image processor 838 selects sub-matrix 1070 (FIG. 27D). When the center of sensor assembly 838 is directed to point $O_5$ directly below point $O_1$, image processor 838 selects sub-matrix 1072 (FIG. 27E). When the center of sensor assembly 838 is directed to point $O_6$ directly above point $O_1$, image processor 838 selects sub-matrix 1074 (FIG. 27F).

In the following description, object 810 (FIGS. 20A and 20B) and object 766 (FIG. 25A) are used interchangeably, although they both represent the same object. Object 810 is described in connection with multiple aperture 804 and illumination unit 830, while object 766 is described in connection with the location of sensor assembly 768 relative thereto. It is noted that during the time interval in which the opening of multiple aperture 804 switches from aperture $802_R$ (FIG. 20A), to aperture $802_L$ (FIG. 20B), sensor assembly 768 moves relative to object 766, due to the vibrations of the human hand. Thus, for example, sub-matrix 1064 (FIG. 27A) represents a right view image of object 810 corresponding to the image which image processor 838 captures, when aperture $802_R$ is open. On the other hand, sub-matrix 1066 (FIG. 27B) represents a left view image of object 766, when aperture $802_L$ is open.

Furthermore, the color of detected images 1052, 1054, 1056, 1058, 1060, and 1062 changes as described herein above for example in connection with FIG. 21B. Image processor 838 receives download image $841'_A$, and selects sub-matrix 1064 (FIG. 27A), which is a right view image of object 766 (FIG. 25A) in blue, when the center of sensor assembly 768 is directed to point $O_1$.

While multiple aperture 804 switches to aperture $802_L$, the center of sensor assembly 768 (FIG. 25B) directs to point $O_2$ (FIG. 25B), and image processor 838 receives download image $841'_B$. Since the center of sensor assembly 768 is directed to point $O_2$ (FIG. 25B), then image processor 838 selects sub-matrix 1066 (FIG. 27B) which represents a left view image of object 810 in blue. Analogously, sub-matrix 1068 (FIG. 27C) represents a green right view image of object 766 (download image $841'_C$), when the center of sensor assembly 768 is directed to point $O_3$ (FIG. 25C). Sub-matrix 1070 (FIG. 27D) represents a green left view image of object 766 (download image $841'_D$), when the center of sensor assembly 768 directs to point $O_4$ (FIG. 25D). Sub-matrix 1072 (FIG. 27E) represents a red right view image of object 766 (download image $841'_E$), when the center of sensor assembly 768 directs to point $O_5$ (FIG. 25E). Sub-matrix 1074 (FIG. 27F) represents a red left view image of object 766 (download image $841'_F$), when the center of sensor assembly 768 directs to point $O_6$ (FIG. 25F).

According to FIG. 21A, a stereoscopic display unit (not shown) displays sub-matrices 1064, 1066, 1068, 1070, 1072 and 1074 in sequence. Sub-matrices 1064, 1068 and 1072 are the right side views of substantially the same area of object 766, which together compose a right side color image of the object 766. Sub-matrices 1066, 1070 and 1074 are the left side views of substantially the same area of object 766, which together compose a left side color image of the object 766. The stereoscopic display unit alternately displays the right view image and the left view image of substantially the same area of object 766. Thus, system 800 maintains a stable image of object 766, which does not exhibit any change in the location of object 766 as displayed on the stereoscopic display unit, despite the movement of sensor assembly 768 due to the vibrations of the human hand.

For example, image processor 838 selects sub-matrices 1064, 1068 and 1072 (FIGS. 27A, 27C and 27E, respectively), and the stereoscopic display (not shown), sequentially displays the same image in blue, green and red, respectively. Thus, the stereoscopic display presents a stable right side image of the object in full color, to the right eye. Similarly, the stereoscopic display sequentially displays sub-matrices 1066, 1070 and 1074 (FIGS. 27B, 27D and 27F, respectively), wherein the color of each sub-matrix sequentially changes from blue to green to red, respectively. In this manner, the stereoscopic display presents a stable left side image of the object in full color, to the left eye. Thus, the user views a stable full color stereoscopic image of the object, despite the movement of the endoscope due to the vibrations of the human hand.

It is noted that an RGB timing scheme can be employed. In this case, the stereoscopic display displays the sub-matrices in a sequence of right-red, left-green, right-blue, left-red, right-green and left-blue.

It is noted that the sequence of FIGS. 27A, 27B, 27C, 27D, 27E and 27F is cyclically repeated during the imaging process of the object. Other timing schemes can be employed where the download image trigger signal is used for acquiring a reading from movement detector 814, for the detected image. Examples for such timing schemes are illustrated in FIGS. 23, 24, and 21A.

According to another aspect of the disclosed technique, the locations from which the three-dimensional object is viewed from the right side and from the left side thereof, are further separated. Thus, the difference between the right side view image and the left side view image is substantially increased and the stereoscopic notion produced by the two images is substantially enhanced.

Figure 28A:
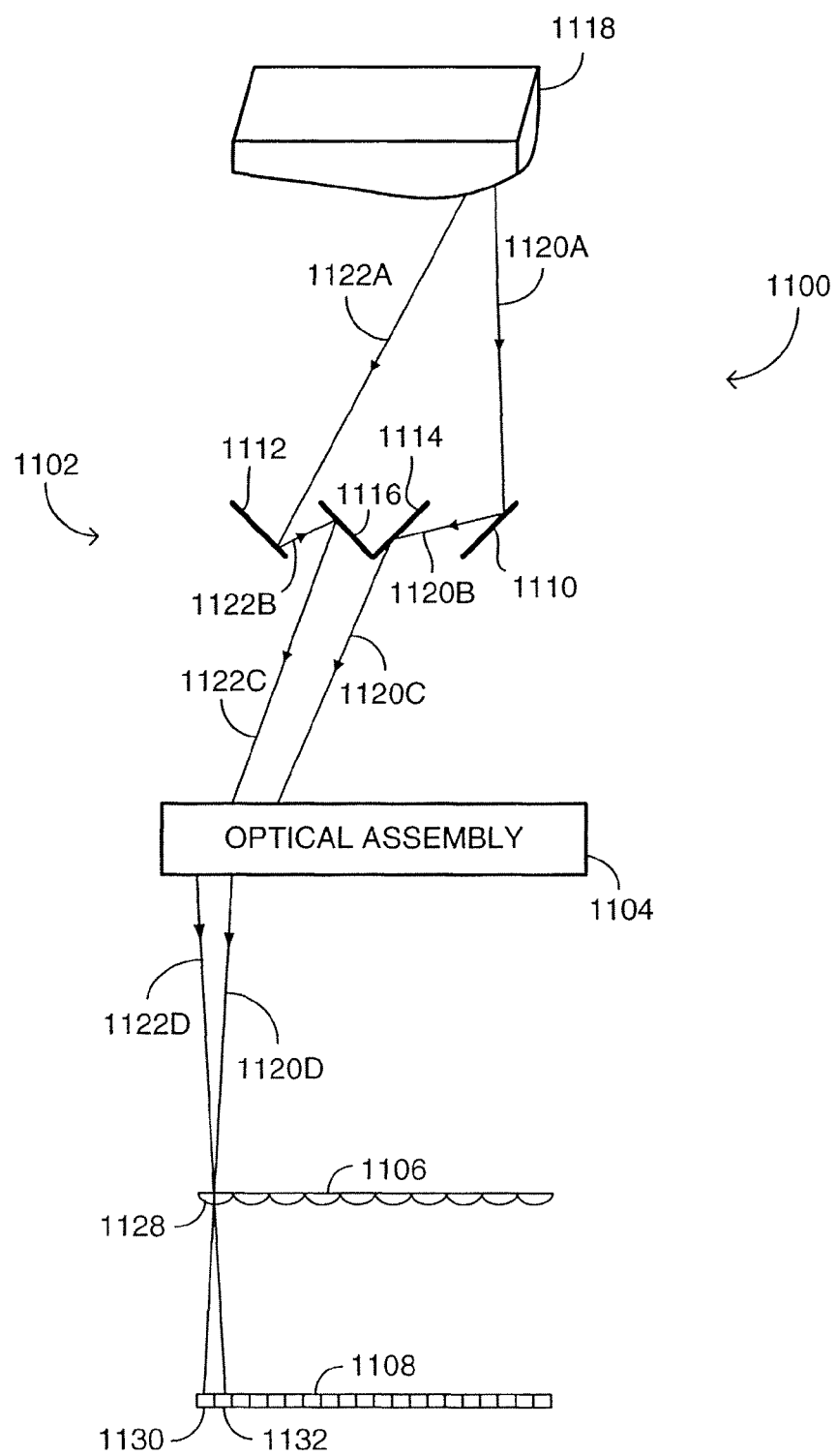
FIG. 28A is a schematic illustration of a stereoscopic imaging apparatus, constructed and operative in accordance with a further embodiment of the disclosed technique.
Figure 28B:
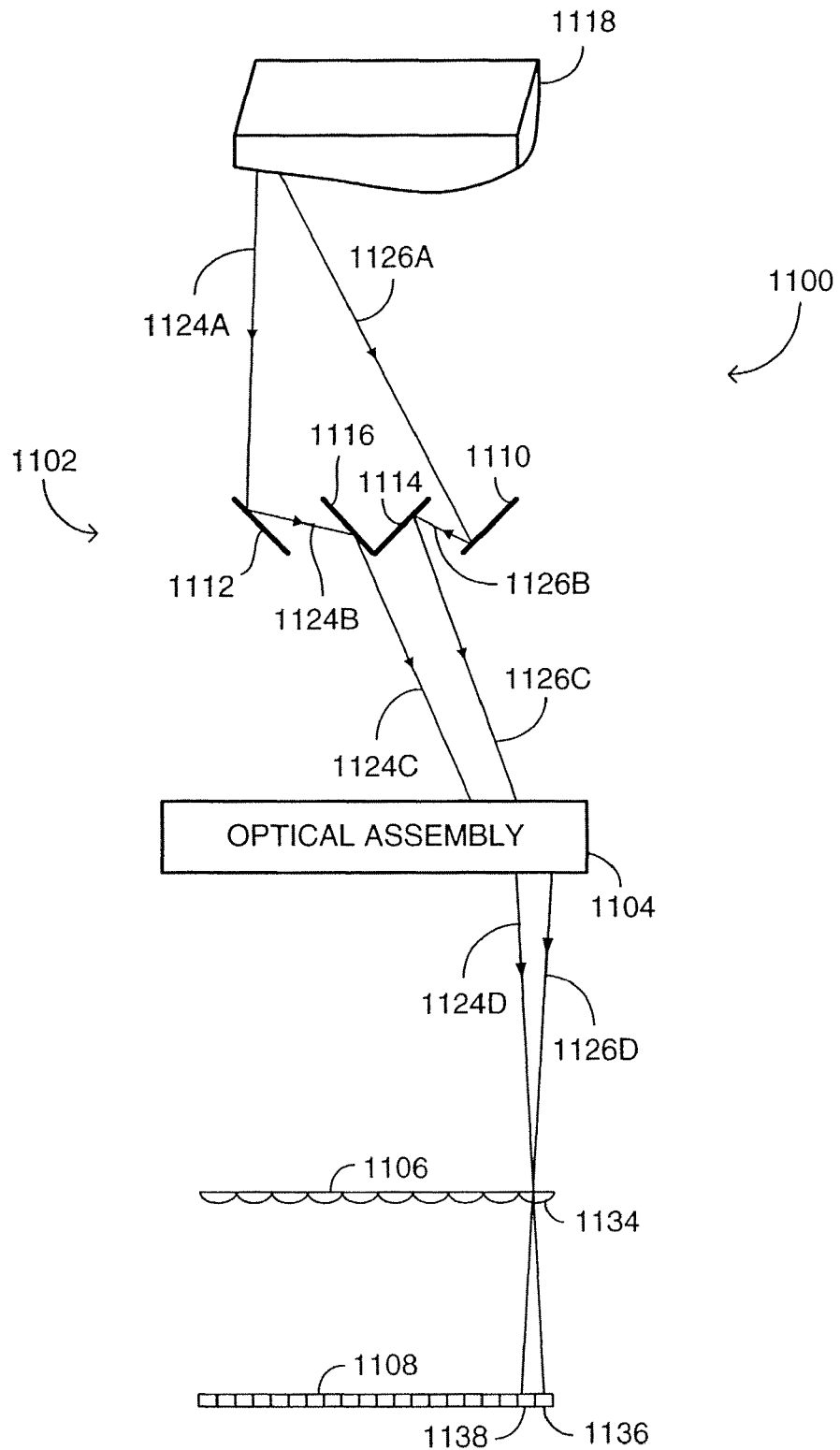
FIG. 28B is a schematic illustration of the apparatus of FIG. 28A, in another mode of imaging.

Reference is now made to FIGS. 28A and 28B. FIG. 28A is a schematic illustration of a stereoscopic imaging apparatus, generally referenced 1100, constructed and operative in accordance with a further embodiment of the disclosed technique. FIG. 28B is a schematic illustration of the apparatus of FIG. 28A, in another mode of imaging.

Apparatus 1100 includes a periscopic assembly 1102, an optical assembly 1104, a lenticular lens layer 1106 and a light sensor array 1108. Periscopic assembly 1102 includes a right mirror 1110, a left mirror 1112, a right center mirror 1114 and a left center mirror 1116. Lenticular lens layer 1106 and light sensor array 1108 are similar to lenticular lens layer 104 and light sensor array 102, respectively, as described herein above in connection with FIG. 1. However, lenticular lens layer 1106 is positioned in an orientation opposite to that illustrated in FIG. 1. Periscopic assembly 1102 is located between a three-dimensional object 1118 and optical assembly 1104. Optical assembly 1104 is located between periscopic assembly 1102 and lenticular lens layer 1106.

With reference to FIG. 28A, right mirror 1110 receives a light beam 1120A, which is a right side view of the right side of three-dimensional object 1118. Right mirror 1110 reflects light beam 1120A, as a light beam 1120B. Right center mirror 1114 reflects light beam 1120B toward optical assembly 1104, as a light beam 1120C. Optical assembly 1104 directs a light beam 1120D to a lenticular element 1128 of lenticular lens layer 1106. Lenticular element 1128 focuses light beam 1120D on a sensor 1130 of light sensor array 1108. Light sensor array 1108 detects the right side view image of three-dimensional object 1118 and provides a respective signal to a processor, such as processor 208 (FIG. 2), via an interface, such as interface 210.

Left mirror 1112 receives a light beam 1122A, which is a left side view of the right side of three-dimensional object 1118. Left mirror 1112 reflects light beam 1122A, as a light beam 1122B. Left center mirror 1116 reflects light beam 1122B toward optical assembly 1104, as a light beam 1122C. Optical assembly 1104 directs a light beam 1122D to lenticular element 1128 of lenticular lens layer 1106. Lenticular element 1128 focuses light beam 1122D on a sensor 1132 of light sensor array 1108.

With reference to FIG. 28B, left mirror 1112 receives a light beam 1124A, which is a left side view of the left side of three-dimensional object 1118. Left mirror 1112 reflects light beam 1124A, as a light beam 1124B. Left center mirror 1116 reflects light beam 1124B toward optical assembly 1104, as a light beam 1124C. Optical assembly 1104 directs a light beam 1124D to a lenticular element 1134 of lenticular lens layer 1106. Lenticular element 1134 focuses light beam 1124D on a sensor 1136 of light sensor array 1108.

Right mirror 1110 receives a light beam 1126A, which is a right side view of the left side of three-dimensional object 1118. Right mirror 1110 reflects light beam 1126A, as a light beam 1126B. Right center mirror 1114 reflects light beam 1126B toward optical assembly 1104, as a light beam 1126C. Optical assembly 1104 directs a light beam 1126D to lenticular element 1134 of lenticular lens layer 1106. Lenticular element 1134 focuses light beam 1126D on a sensor 1138 of light sensor array 1108.

It is noted that right mirror 1110 and right center mirror 1114 together operate similar to a periscope. Likewise, left mirror 1112 and left center mirror 1116 together operate similar to a periscope. Right mirror 1110 and left mirror 1112 are located substantially apart relative to an axis which is perpendicular to lenticular lens layer 1106 and which passes through the junction of right center mirror 1114 and left center mirror 1116. Hence, right mirror 1110 detects a right side view of three-dimensional object 1118, which is substantially different than the left side view thereof, detected by left mirror 1112. Thus, the respective light detecting elements of light sensor array 1108 receive light beams respective of the right side view and the left side view of three-dimensional object 1118, which are more distinct than in the case of FIG. 1. Hence, apparatus 1100 can provide a sharper stereoscopic image of three-dimensional object 1118, than an apparatus similar to apparatus 200 (FIG. 2).

According to another aspect of the disclosed technique, a light valve alternately differentiates between images of a three-dimensional object received from different directions, and alternately provides these images to an image detector. Thus, the image detector alternately detects images of the three-dimensional object, from different sides thereof.

Figure 29A:
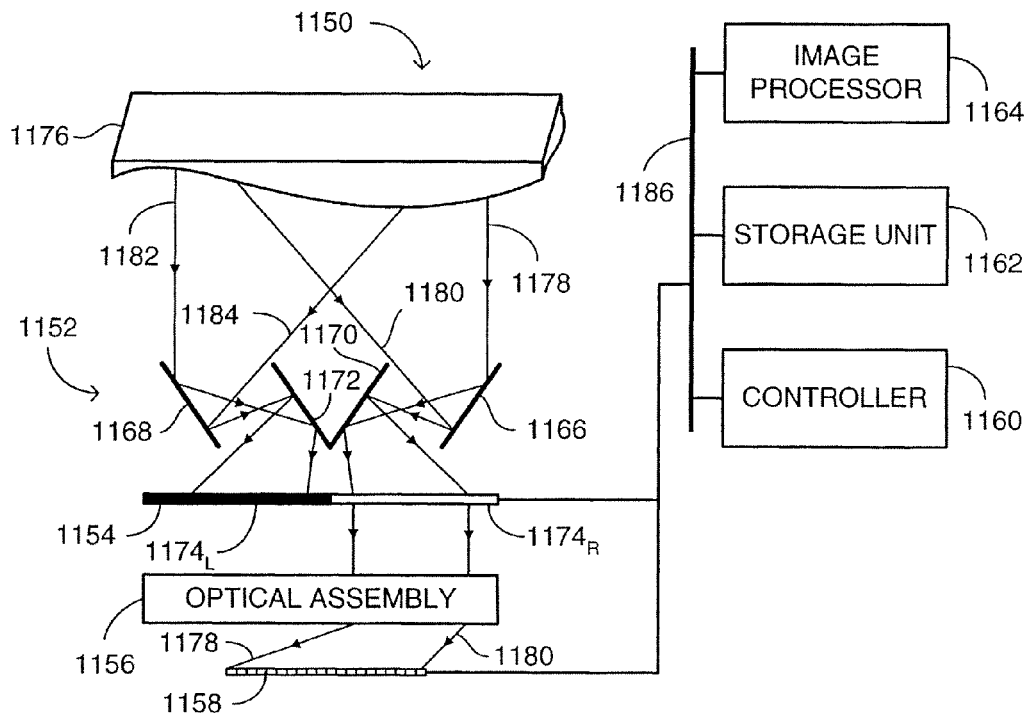
FIG. 29A is a schematic illustration of a stereoscopic imaging apparatus in a right side detection mode, constructed and operative in accordance with another embodiment of the disclosed technique.
Figure 29B:
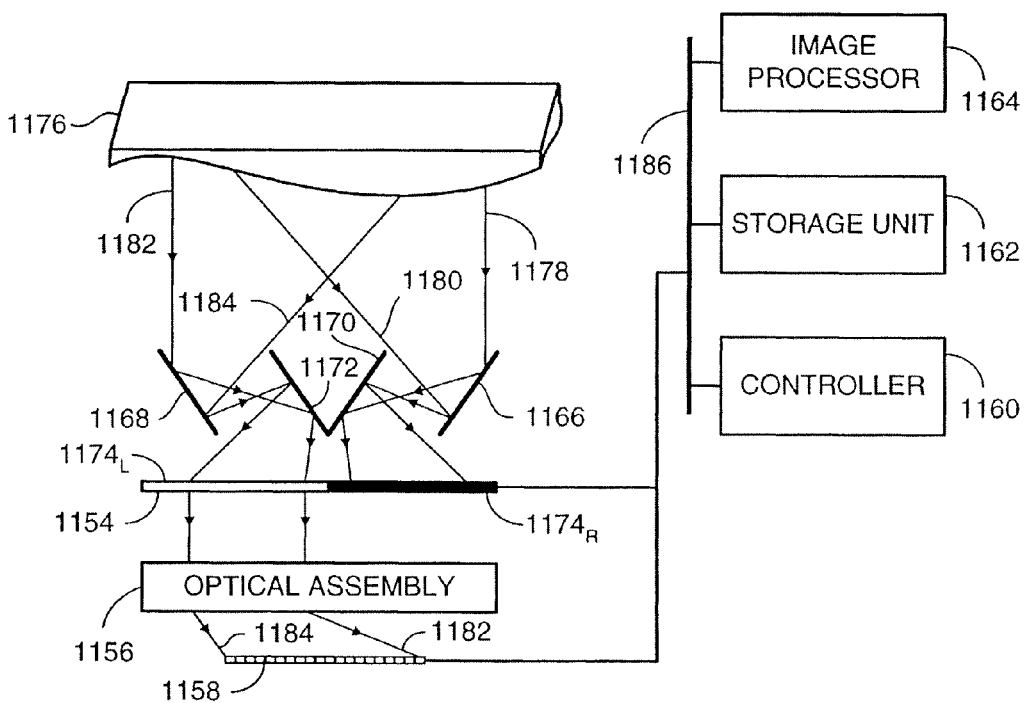
FIG. 29B is a schematic illustration of the apparatus of FIG. 29A, in a left side detection mode.

Reference is now made to FIGS. 29A and 29B. FIG. 29A is a schematic illustration of a stereoscopic imaging apparatus in a right side detection mode, generally referenced 1150, constructed and operative in accordance with another embodiment of the disclosed technique. FIG. 29B is a schematic illustration of the apparatus of FIG. 29A, in a left side detection mode.

Apparatus 1150 includes a periscope assembly 1152, a multiple aperture 1154, an optical assembly 1156, a light sensor array 1158, a controller 1160, a storage unit 1162 and an image processor 1164. Periscope assembly 1152 includes a right mirror 1166, a left mirror 1168, a right center mirror 1170 and a left center mirror 1172. Multiple aperture 1154 includes a right aperture $1174_R$ and a left aperture $1174_L$. Multiple aperture 1154 is similar to multiple aperture 804, as described herein above in connection with FIG. 20A.

Periscope assembly 1152 is located between a three-dimensional object 1176 and multiple aperture 1154. Multiple aperture 1154 is located between periscope assembly 1152 and optical assembly 1156. Multiple aperture 1154 is located substantially close to periscope assembly 1152. Optical assembly 1156 is located between multiple aperture 1154 and light sensor array 1158. Multiple aperture 1154, light sensor array 1158, controller 1160, storage unit 1162 and image processor 1164, are interconnected via a bus 1186. Controller 1160 controls multiple aperture 1154, such that right aperture $1174_R$ and left aperture $1174_L$ alternately open and close.

With reference to FIG. 29A, controller 1160 controls multiple aperture 1154, such that right aperture $1174_R$ is open and left aperture $1174_L$ is closed. Right mirror 1166 receives light beams 1178 and 1180 as reflected from three-dimensional object 1176. Left mirror 1168 receives light beams 1182 and 1184 as reflected from three-dimensional object 1176. Right center mirror 1170 reflects the reflection of light beams 1178 and 1180 toward right aperture $1174_R$. Since right aperture $1174_R$ is open, light beams 1178 and 1180 pass through right aperture $1174_R$, reach light sensor array 1158 through optical assembly 1156. Controller 1160 enables light sensor array 1158 to detect a right side view image of three-dimensional object 1176, according to the state of multiple aperture 1154 (i.e., when right aperture $1174_R$ is open). Controller 1160 stores this right side view image in storage unit 1162. Since left aperture $1174_L$ is closed, light beams 1182 and 1184 which are reflected by left mirror 1168 and left center mirror 1172, are blocked and do not reach light sensor array 1158.

With reference to FIG. 29B, controller 1160 controls multiple aperture 1154, such that right aperture $1174_R$ is closed and left aperture $1174_L$ is open. Light beams 1182 and 1184 reach light sensor array 1158, after reflections from left mirror 1168 and left center mirror 1172 and after passing through left aperture $1174_L$ and optical assembly 1156. Controller 1160 enables light sensor array 1158 to detect a left side view image of three-dimensional object 1176, according to the state of multiple aperture 1154 (i.e., when left aperture $1174_L$ is open). Controller 1160 stores this left side view image in storage unit 1162. Since right aperture $1174_R$ is closed, light beams 1178 and 1180 which are reflected by right mirror 1166 and right center mirror 1170, are blocked and do not reach light sensor array 1158. Controller 1160 alternately stores right and left side view images of three-dimensional object 1176 in storage unit 1162, according to the state of multiple aperture 1154. Image processor 1164 produces a video signal for a stereoscopic display, such as stereoscopic display 214 (FIG. 2), by retrieving these images from storage unit 1162 and processing them.

Alternatively, multiple aperture 1154 is located between three-dimensional object 1176 and periscope assembly 1152. In this case, right mirror 1166 receives a right side view image of three-dimensional object 1176 only when right aperture $1174_R$ is open. Similarly, left mirror 1168 receives the left side view image of three-dimensional object 1176, only when left aperture $1174_L$ is open. Multiple aperture 1154 is located substantially close to periscope assembly 1152.

Alternatively, an illuminator similar to illuminator 830 (FIG. 20A) is employed, in order to sequentially illuminate the three-dimensional object by red, green and blue light. The operation of the illuminator is controlled by a controller. In this case, when the right aperture is open, the light sensor array sequentially detects the right side view image of the three-dimensional object, in red, green and blue colors. The controller sequentially stores the red, green and blue frames of the right side view image of the object in the storage unit. When the left aperture is open, the light sensor array sequentially detects the left side view image of the three-dimensional object, in red, green and blue colors. The controller sequentially stores the red, green and blue frames of the left side view image of the object in the storage unit. The image processor, then produces a video signal respective of the full-color right side view image and the full-color left side view image of the object and a stereoscopic display displays a stereoscopic image of the object in full color.

It is noted that the illuminator can emit light in the visible range of wavelengths, as well as in the invisible range of wavelengths. In addition, the wavelength of light emitted by the illuminator can be generally discrete (e.g., green light is emitted either at 500 nm, 525 nm, 542 nm, and so on).

According to another aspect of the disclosed technique, image differentiation is performed sequentially by filtering light at different sets of wavelengths for each of the right side image and the left side image. According to one embodiment two different light filters, a right side filter and a left side filter, are placed between a three-dimensional object and an image detector. The right side filter admits light at one set of ranges of wavelengths and the left side filter admits light at another set of ranges of wavelengths. The two sets of ranges of wavelengths are mutually exclusive. The right side filter receives a right side view image of the three-dimensional object and the left side filter receives a left side view image of the three-dimensional object.

The three-dimensional object is sequentially illuminated with two groups of wavelengths. The first group of wavelengths is included only in the set of ranges of wavelengths of right side filter. The second group of wavelengths is included only in the set of ranges of wavelengths of the left side filter.

When the object is illuminated with first group of wavelengths, the right side filter passes a right side image to the image detector, while the left side filter blocks these wavelengths. Similarly, when the object is illuminated with second group of wavelengths, the left side filter passes a left side image to the image detector, while the right side filter blocks these wavelengths.

Figure 30A:
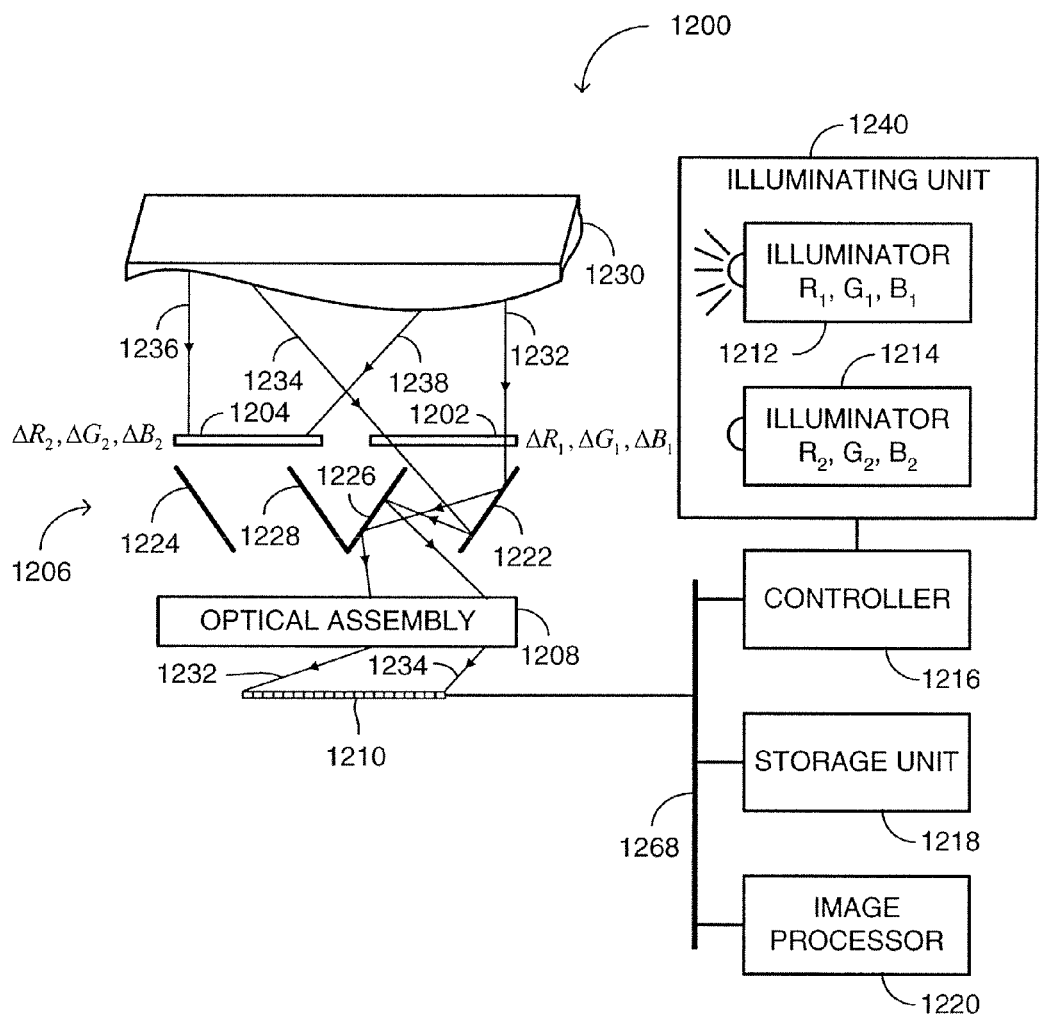
FIG. 30A is a schematic illustration of a stereoscopic imaging apparatus in a right side filter mode, constructed and operative in accordance with a further embodiment of the disclosed technique.
Figure 30B:
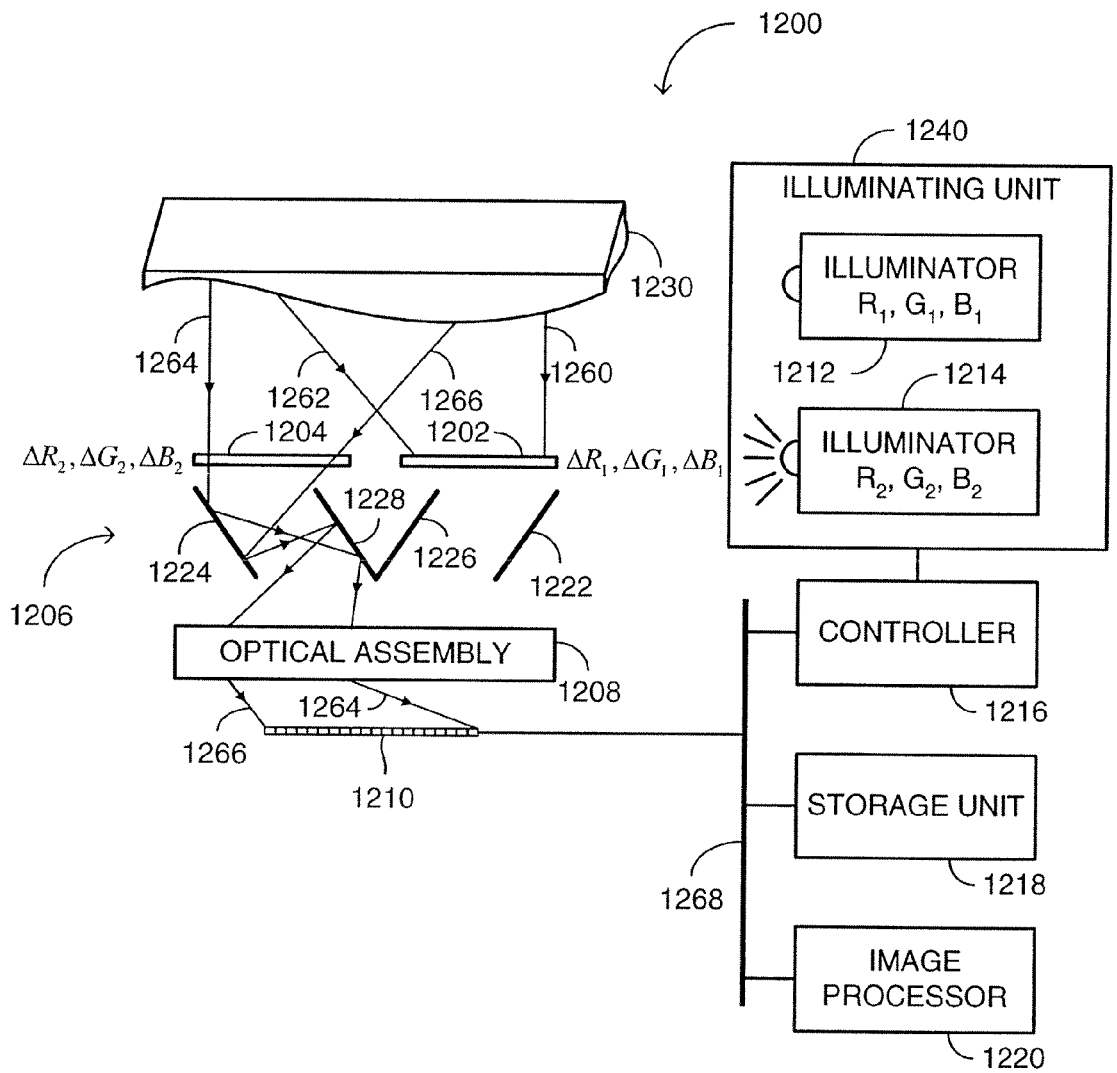
FIG. 30B is a schematic illustration of the apparatus of FIG. 30A, in a left side filter mode.

Reference is now made to FIGS. 30A and 30B. FIG. 30A is a schematic illustration of a stereoscopic imaging apparatus in a right side filter mode, generally referenced 1200, constructed and operative in accordance with a further embodiment of the disclosed technique. FIG. 30B is a schematic illustration of the apparatus of FIG. 30A, in a left side filter mode.

Apparatus 1200 includes a right side filter 1202, a left side filter 1204, a periscope assembly 1206, an optical assembly 1208, a light sensor array 1210, an illuminating unit 1240, a controller 1216, a storage unit 1218 and an image processor 1220. Periscope assembly 1206 includes a right mirror 1222, a left mirror 1224, a right center mirror 1226 and a left center mirror 1228. Illuminating unit 1240 includes illuminators 1212 and 1214. Right side filter 1202 is a light filter, which admits light only in red, green and blue ranges of wavelengths $\Delta R_1$, $\Delta G_1$ and $\Delta B_1$, respectively. Left side filter 1204 is a light filter which admits light only in red, green and blue ranges of wavelengths $\Delta R_2$, $\Delta G_2$ and $\Delta B_2$, respectively, where the ranges of wavelengths $\Delta R_1$, $\Delta G_1$ and $\Delta B_1$ and the ranges of wavelengths $\Delta R_2$, $\Delta G_2$ and $\Delta B_2$ do not overlap. Illuminator 1212 emits light at the group of wavelengths $R_1$, $G_1$ and $B_1$ (i.e., $RGB_1$), which are is included in the ranges of wavelengths $\Delta R_1$, $\Delta G_1$ and $\Delta B_1$ and excluded from the ranges of wavelengths $\Delta R_2$, $\Delta G_2$ and $\Delta B_2$. Illuminator 1214 emits light at the group of wavelengths $R_2$, $G_2$ and $B_2$ (i.e., $RGB_2$), which is included in the ranges of wavelengths $\Delta R_2$, $\Delta G_2$ and $\Delta B_2$ and excluded from the ranges of wavelengths $\Delta R_1$, $\Delta G_1$ and $\Delta B_1$. Thus, illuminating unit 1240 sequentially emits light at the group of wavelengths $RGB_1$ and $RGB_2$. It is noted that $R_1$ refers to one wavelength or more, which are included in the red wavelength range R, arranged continuously, discretely or in a mixed fashion. The same applies to $R_2$ with respect to R, $G_1$ and $G_2$ with respect to the green wavelength range G and $B_1$ and $B_2$ with respect to the blue wavelength range B. This applies to all types of wavelength differentiators which shall be disclosed further below.

In the example set forth in FIGS. 30A and 30B, each of illuminators 1212 and 1214 emits light in the visible range (i.e., different wavelengths of red, green and blue). Accordingly, each of right side filter 1202 and left side filter 1204 admits light in different ranges of red, green and blue, which include the red, green and blue wavelengths of right side filter 1202 and left side filter 1204, respectively. Alternatively, each of the illuminators emits light in the invisible range, such as infrared, and the like, and each of the right side filter and the left side filter admits light in different ranges of wavelengths corresponding to the wavelengths of light emitted by the illuminators.

Right side filter 1202 and left side filter 1204 are located between a three-dimensional object 1230 and periscope assembly 1206. Optical assembly 1208 is located between periscope assembly 1206 and light sensor array 1210. Light sensor array 1210, controller 1216, storage unit 1218 and image processor 1220 are interconnected via a bus 1268. Illuminating unit 1240 is coupled with controller 1216.

With reference to FIG. 30A, controller 1216 controls illuminating unit 1240, to illuminate three-dimensional object 1230 at the group of wavelengths $RGB_1$. Three-dimensional object 1230 reflects the light at the group of wavelengths $RGB_1$ toward right side filter 1202, as light beams 1232 and 1234 and toward left side filter 1204, as light beams 1236 and 1238. Light beams 1232 and 1234 include information respective of a right side view image of three-dimensional object 1230. Light beams 1236 and 1238 include information respective of a left side view image of three-dimensional object 1230. Since right side filter 1202 admits light in the ranges of wavelengths $\Delta R_1$, $\Delta G_1$ and $\Delta B_1$, and the group of wavelengths $RGB_1$ is included in the ranges of wavelengths $\Delta R_1$, $\Delta G_1$ and $\Delta B_1$, light beams 1232 and 1234 pass through right side filter 1202 and reach right mirror 1222.

Right center mirror 1226 reflects the reflection of light beams 1232 and 1234 from right mirror 1222, to optical assembly 1208. Optical assembly 1208 focuses light beams 1232 and 1234 on light sensor array 1210. Thus, when illuminating unit 1240 emits light at the group of wavelengths $RGB_1$ the right side view image of three-dimensional object 1230 at the group of wavelengths $RGB_1$ reaches light sensor array 1210. It is noted that since the group of wavelengths $RGB_1$ is not included in any of the ranges of wavelengths at which left side filter 1204 admits light, left side filter 1204 blocks light beams 1236 and 1238, and that the left side view image of three-dimensional object 1230 does not reach light sensor array 1210 at this stage. Controller 1216 stores this right side view image of three-dimensional object 1230, in storage unit 1218.

With reference to FIG. 30B, controller 1216 controls illuminating unit 1240, to illuminate three-dimensional object 1230 at the group of wavelengths $RGB_2$. Three-dimensional object 1230 reflects the light at the group of wavelengths $RGB_2$ toward left side filter 1204, as light beams 1264 and 1266 and toward right side filter 1202, as light beams 1260 and 1262. Light beams 1264 and 1266 include information respective of a left side view image of three-dimensional object 1230. Light beams 1260 and 1262 include information respective of a right side view image of three-dimensional object 1230. Since left side filter 1204 admits light in the ranges of wavelengths $\Delta R_2$, $\Delta G_2$ and $\Delta B_2$, and the group of wavelengths $RGB_2$ is included in the ranges of wavelengths $\Delta R_2$, $\Delta G_2$ and $\Delta B_2$, light beams 1264 and 1266 pass through left side filter 1204 and reach left mirror 1224.

Left center mirror 1228 reflects the reflection of light beams 1264 and 1266 from left mirror 1224, to optical assembly 1208. Optical assembly 1208 focuses light beams 1264 and 1266 on light sensor array 1210. Thus, when illuminating unit 1240 emits light at the group of wavelengths $RGB_2$ the left side view image of three-dimensional object 1230 at the group of wavelengths $RGB_2$ reaches light sensor array 1210. Since the group of wavelengths $RGB_2$ is not included in any of the ranges of wavelengths at which right side filter 1202 admits light, right side filter 1202 blocks light beams 1260 and 1262, and the right side view image of three-dimensional object 1230 does not reach light sensor array 1210 at this stage. Controller 1216 stores this left side view image of three-dimensional object 1230, in storage unit 1218.

Image processor 1220 retrieves the right side and the left side view images of three-dimensional object 1230, from storage unit 1218 and produces stereoscopic images of three-dimensional object 1230, by processing the right side and the left side view images. It is noted that in the example set forth in FIGS. 30A and 30B, light sensor array 1210 is a color light detector.

Alternatively, in a system which includes a full range light sensor array, the controller controls the operation of the illuminating unit, to sequentially emit light at individual groups of wavelengths $R_1$, $R_2$, $G_1$, $G_2$, $B_1$ and $B_2$. In this case, the right side filter admits a sequence of right side view images of the three-dimensional object, in each of the ranges of wavelengths $R_1$, $G_1$ and $B_1$, and then the left side filter admits a sequence of left side view images of the three-dimensional object, in each of the wavelengths $R_2$, $G_2$ and $B_2$. For each cycle in the illumination sequence, the controller enables the light sensor array to detect six images of the three-dimensional object. Three of these images are right side view images, each at a different one of the groups of wavelengths $R_1$, $G_1$ and $B_1$. The other three images are left side view images, each at a different one of the groups of wavelengths $R_2$, $G_2$ and $B_2$. It is noted that other sequences of $R_1$, $R_2$, $G_1$, $G_2$, $B_1$ and $B_2$, as well as other divisions of light (e.g., $CYMG_1$ and $CYMG_2$) are applicable.

In the example set forth in FIGS. 30A and 30B, system 1200 is constructed to operate in the visible range. Alternatively, a system according to another embodiment can be constructed to operate in the invisible range, such as infrared (far and near), ultra-violet, and the like.

Alternatively, each of the illuminators 1212 and 1214 can include several light sources, each at a different group of wavelengths (e.g., an illuminator for each of $\Delta R_1$, $\Delta G_1$, $\Delta B_1$, $\Delta R_2$, $\Delta G_2$ and $\Delta B_2$). It is noted that this aspect of the disclosed technique, can be limited to a single range for each channel (i.e., blue for the right channel and red for the left channel).

Alternatively, the right side filter and the left side filter are located between the periscope assembly and the optical assembly. In this case, the right side filter receives a right side view image of the three-dimensional object from the right center mirror, and the left side filter receives a left side view image of the three-dimensional object from the left center mirror.

Alternatively, a rotating disk is placed in front of the periscope assembly and an illuminator constantly emits light. Half of the rotating disk is transparent and the other half is opaque. Thus, as the rotating disk rotates, the periscope assembly alternately receives the right side and the left side view images of the three-dimensional object and directs these images to the light sensor array.

With reference to FIG. 30A, a partially-transparent rotating disk replaces right side filter 1202 and left side filter 1204. Furthermore, an illuminator which provides light in a predetermined range of wavelengths, replaces illuminating unit 1240. The partially-transparent rotating disk is divided into a transparent portion and an opaque portion, as described herein below in connection with FIGS. 39A and 39B.

When the transparent portion of the partially-transparent rotating disk is located above the right mirror, the right mirror receives a right side view image of the three-dimensional object and the opaque portion of the partially-transparent rotating disk blocks the light to the left mirror. When the transparent portion of the partially-transparent rotating disk is located above the left mirror, the left mirror receives a left side view image of the three-dimensional object and the opaque portion of the partially-transparent rotating disk blocks the light to the right mirror. The controller enables the light sensor array to alternately detect a right side view image and a left side view image of the three-dimensional object, according to the position of the transparent portion relative to the right mirror and the left mirror. The controller alternately stores the right side view images and the left side view images in the storage unit. The image processor concurrently retrieves the right side view images and left side view images of the three-dimensional object, processes these images and provides a respective video signal to a stereoscopic display, such as stereoscopic display 214 (FIG. 2).

Alternatively, a rotating disk is placed in front of the periscope assembly and a multi-wavelength illuminator sequentially emits light in different ranges of wavelengths. Half of the rotating disk is transparent and the other half is opaque. As the rotating disk rotates, the periscope assembly receives a sequence of right side and left side view images of the three-dimensional object, in different ranges of wavelengths and directs these images to the light sensor array. This embodiment is similar to the embodiments described herein above in connection with FIGS. 14B, 20A and 20B.

With reference to FIG. 30A, a partially-transparent rotating disk replaces right side filter 1202 and left side filter 1204. Furthermore, a multi-wavelength illuminator which sequentially emits light in different ranges of wavelengths, replaces illuminating unit 1240. Half of the partially-transparent rotating disk is transparent and the other half is opaque. The partially-transparent rotating disk is coupled with the controller. The controller controls the operation of the multi-wavelength illuminator, to sequentially emit light in different ranges of wavelengths. As the partially-transparent rotating disk rotates, the transparent portion alternately covers the right mirror and the left mirror. The controller enables the light sensor array to detect each of the right side and the left side view images of the three-dimensional object, in these different ranges of wavelengths, according to the angular position of the partially-transparent rotating disk and the state of the multi-wavelength illuminator. The controller stores these images in the storage unit.

For example, when the multi-wavelength illuminator sequentially illuminates the three-dimensional object in red, green and blue (i.e., RGB), and the transparent portion is located above the right mirror, the light sensor array detects a sequence of images in red, green and blue. According to the position of the partially-transparent rotating disk and the state of the multi-wavelength illuminator, the controller determines that these images are right side view images of the three-dimensional object, in red, green and blue, respectively. The controller stores these images in the storage unit.

The light sensor array detects right side view images when the transparent portion is located above the right mirror. The light sensor array detects left side view images when the transparent portion is located above the left mirror. The controller tags each of these images according to the state of multi-wavelength illuminator (e.g., red, green and blue) at the time when each of these images was captured. According to a simple setting, at a given time period, the stereoscopic imaging apparatus produces six images, three for each side, two for each color (e.g., a left side blue image, a left side green image, a left side red image, a right side blue image, a right side green image and a right side red image).

Alternatively, a rotating disk having an opaque portion and a multi-wavelength transparent portion, is placed in front of the periscope assembly and an illuminator illuminates the three-dimensional object. As the rotating disk rotates, the periscope assembly receives a sequence of right side and left side view images of the three-dimensional object, in different ranges of wavelengths and directs these images to the light sensor array. This embodiment is similar to the embodiments described herein above in connection with FIGS. 14B, 20A and 20B.

With reference to FIG. 30A, a multi-wavelength rotating disk replaces right side filter 1202 and left side filter 1204, and an illuminator replaces illuminating unit 1240. The multi-wavelength rotating disk is divided to an opaque portion and to a transparent portion. The transparent portion is divided to substantially equal filtering sectors, each filtering sector being in a different color, as described herein below in connection with FIG. 40A. Alternatively, the multi-wavelength rotating disk is alternately divided into opaque sectors and filtering sectors, wherein each filtering sector is in a different predetermined range of wavelengths, as described herein below in connection with FIG. 40B. The multi-wavelength rotating disk is coupled with the controller.

The illuminator provides light at least in the predetermined ranges of wavelengths as defined by the filtering sectors. As the multi-wavelength rotating disk rotates, the light sensor array detects a sequence of images. The controller determines the type of each of these images (i.e., either right side view image or left side view image) and the range of wavelengths of each of these images, according to the position of the multi-wavelength rotating disk.

According to another aspect of the disclosed technique, a pair of polarizers direct an image from one side of a three-dimensional object to an image detector, when both polarizers are oriented at the same angle, while another pair of polarizers block an image from another side of the object, when the polarizers are oriented 90 degrees apart. The relative polarization angles between the two polarizers in each pair is alternately changed to be either zero or 90 degrees. Thus, the image detector alternately receives images from different sides of the three-dimensional object.

Figure 31A:
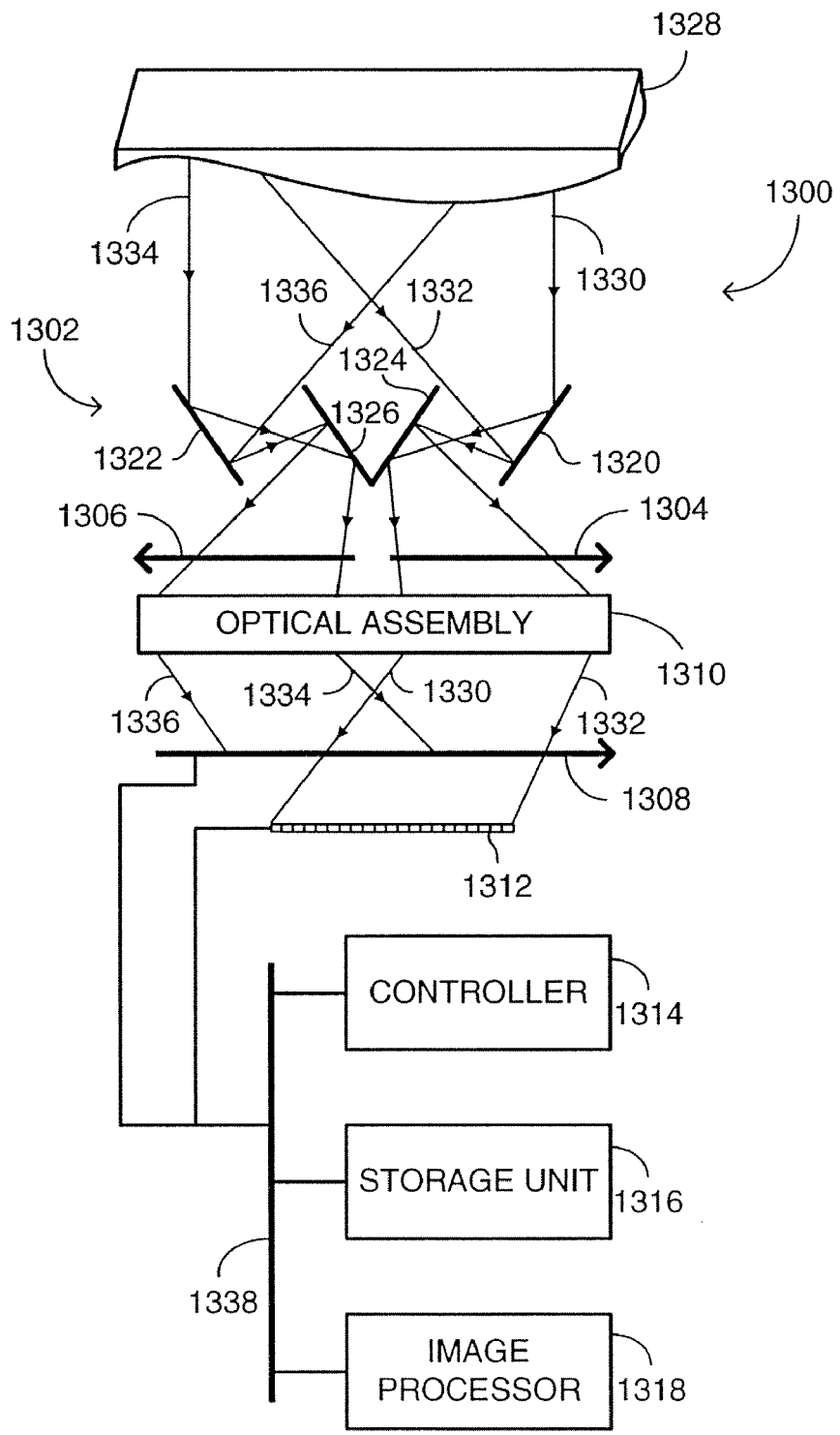
FIG. 31A is a schematic illustration of a stereoscopic imaging apparatus in a right side view image mode, constructed and operative in accordance with another embodiment of the disclosed technique.
Figure 31B:
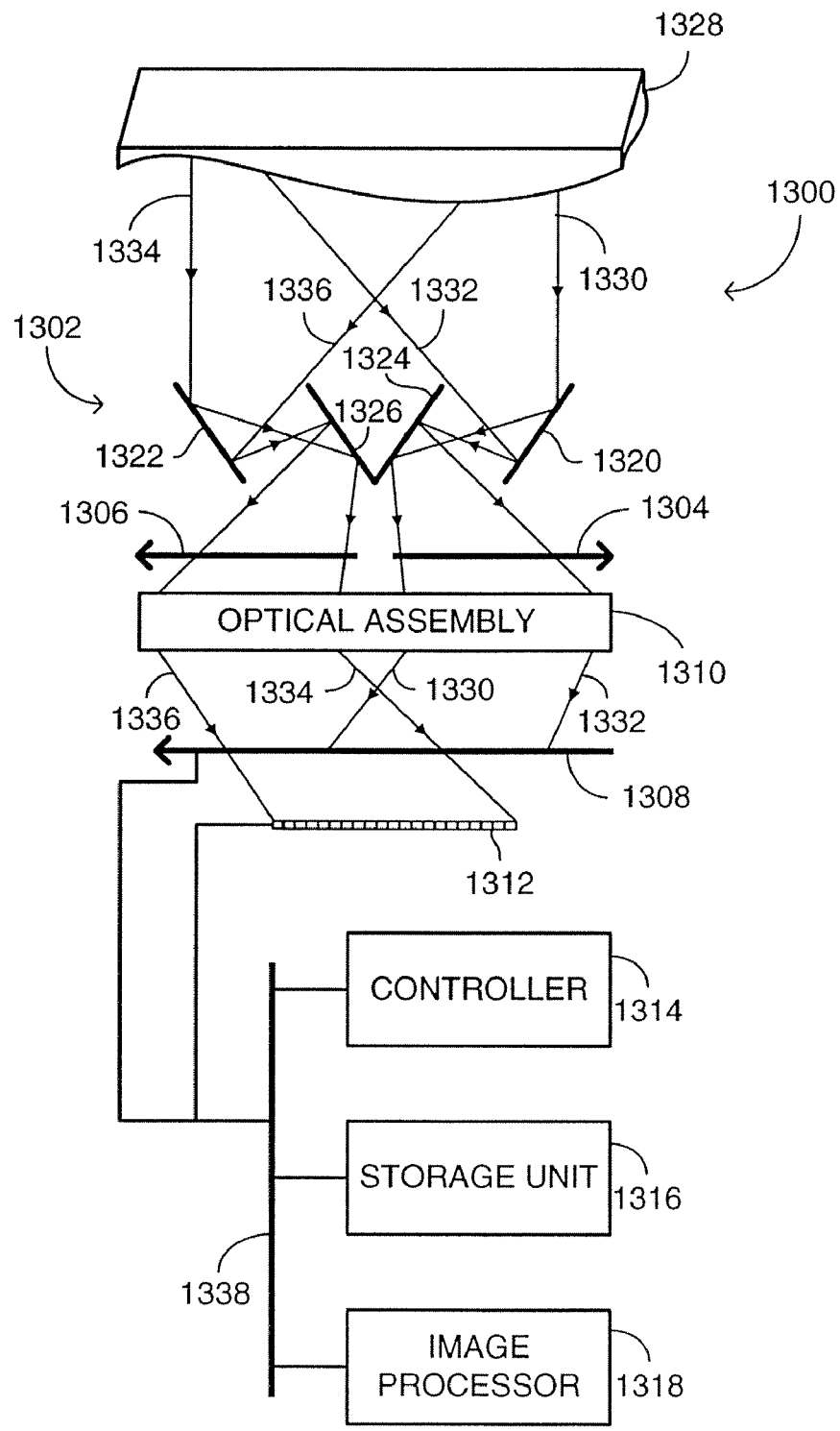
FIG. 31B is a schematic illustration of the apparatus of FIG. 30A, in a left side view image mode.

Reference is now made to FIGS. 31A and 31B. FIG. 31A is a schematic illustration of a stereoscopic imaging apparatus in a right side view image mode, generally referenced 1300, constructed and operative in accordance with another embodiment of the disclosed technique. FIG. 31B is a schematic illustration of the apparatus of FIG. 30A, in a left side view image mode.

Apparatus 1300 includes a periscope assembly 1302, a right polarizer 1304, a left polarizer 1306, a main polarizer 1308, an optical assembly 1310, a light sensor array 1312, a controller 1314, a storage unit 1316 and an image processor 1318. Periscope assembly 1302 includes a right mirror 1320, a left mirror 1322, a right center mirror 1324 and a left center mirror 1326.

Each of right polarizer 1304, left polarizer 1306 and main polarizer 1308 is an optical element which admits light only at a predetermined direction of polarization. In the following example, the polarization angle of the incident light beam is zero degrees, and the polarizer is rotated by 45 degrees relative to this polarization angle. The light vector, having a length of L and being set at zero angle, can be described as a vectorial combination of two vectors, each at a length $\sqrt{2}L$, one directed at 45 degrees and the other directed at −45 degrees. The polarizer admits the vector which is directed at 45 degrees and blocks the vector which is directed at −45 degrees. The polarization angle of a polarizer can be changed electronically. The polarization angle of right polarizer 1304 and left polarizer 1306 is fixed, whereas the polarization angle of main polarizer 1308 can be changed. In the example set forth in FIG. 31A, the polarization angle of left polarizer 1306 is approximately 90 degrees relative to the polarization angle of right polarizer 1304 and the polarization angle of main polarizer 1308 is approximately the same as that of right polarizer 1304. Thus, main polarizer 1308 admits light, which exits right polarizer 1304 and blocks light which exits left polarizer 1306. In the example set forth in FIG. 31B, the polarization angle of main polarizer 1308 is approximately 90 degrees relative to right polarizer 1304. In this case, main polarizer 1308 admits light which exits left polarizer 1306 and blocks light which exits right polarizer 1304.

With reference to FIGS. 31A and 31B, periscope assembly 1302 is located between a three-dimensional object 1328 on one side and right polarizer 1304 and left polarizer 1306 on the other side. Right polarizer 1304 and left polarizer 1306 are located side by side between periscope assembly 1302 and optical assembly 1310. Main polarizer 1308 is located between optical assembly 1310 and light sensor array 1312. Main polarizer 1308, light sensor array 1312, controller 1314, storage unit 1316 and image processor 1318 are interconnected via a bus 1338. Controller 1314 controls the polarization angle of main polarizer 1308.

In the example set forth in FIG. 31A, the polarization angle of main polarizer 1308 is substantially the same as that of right polarizer 1304 and 90 degrees relative to left polarizer 1306. Right mirror 1320 receives a right side view image of three-dimensional object 1328, via light beams 1330 and 1332. Left mirror 1322 receives a left side view image of three-dimensional object 1328, via light beams 1334 and 1336. Right center mirror 1324 reflects the reflection of light beams 1330 and 1332 from right mirror 1320, toward optical assembly 1310. Left center mirror 1326 reflects the reflection of light beams 1334 and 1336 from left mirror 1322, toward optical assembly 1310.

Optical assembly 1310 focuses light beams 1330, 1332, 1334 and 1336 on light sensor array 1312. Since the polarization angles of right polarizer 1304 and left polarizer 1306 are approximately 90 degrees apart, main polarizer 1308 blocks light beams 1334 and 1336. Since the polarization angle of main polarizer 1308 is approximately the same as that of right polarizer 1304, main polarizer 1308 passes light beams 1330 and 1332 toward light sensor array 1312. Controller 1314 enables light sensor array 1312 to detect a right side view image of three-dimensional object 1328, according to the polarization angle main polarizer 1308. Controller 1314 stores this right side view image in storage unit 1316.

With reference to FIG. 31B, the polarization angle of main polarizer 1308 is substantially the same as that of left polarizer 1306 and 90 degrees relative to right polarizer 1304. In this case, main polarizer 1308 blocks light beams 1330 and 1332, and passes light beams 1334 and 1336 toward light sensor array 1312. Controller 1314 enables light sensor array 1312 to detect a left side view image of three-dimensional object 1328, according to the polarization angle of main polarizer 1308. Controller 1314 stores this left side view image in storage unit 1316. Image processor 1318 concurrently retrieves the right side view images and the left side view images of three-dimensional object 1328, processes these images and provides a respective video signal to a stereoscopic display, such as stereoscopic display 214 (FIG. 2).

Alternatively, a rotating polarizing disk replaces right polarizer 1304 and left polarizer 1306. The rotating polarizing disk is divided to two polarizing sections. The polarization angle of the first section is substantially equal to the polarization angle of the main polarizer and the polarization angle of the second section is away from the polarization angle of the main polarizer, by substantially 90 degrees. It is noted that certain limitations may apply to such a rotating polarizing disk, whereas the polarizers on the disk physically rotate. Accordingly, the rotating polarizing disk may include dynamic polarizers, which change according to the angular position of the rotating polarizing disk. Alternatively, the rotating polarizing disk is stopped or slowed down at predetermined angular positions, when an image is acquired.

It is noted that different structures of polarizers can be used for separating the images. Such structures include active and passive polarizers, located at various positions such as between the object and the periscope assembly, between the periscope assembly and the optical assembly and between the optical assembly and the light sensor array. The following are mere examples for such structures of polarizes.

Alternatively, main polarizer 1308 is located between three-dimensional object 1328 and periscope assembly 1302, while right polarizer 1304 and left polarizer 1306 are located between periscope assembly 1302 and optical assembly 1310. Further alternatively, right polarizer 1304 and left polarizer 1306 are located between three-dimensional object 1328 and periscope assembly 1302, while main polarizer 1308 is located between periscope assembly 1302 and optical assembly 1310.

Yet further alternatively, right polarizer 1304 and left polarizer 1306 are located between three-dimensional object 1328 and periscope assembly 1302, while main polarizer 1308 is located between optical assembly 1310 and light sensor array 1312. Still further alternatively, main polarizer 1308 is located between periscope assembly 1302 and optical assembly 1310, while right polarizer 1304 and left polarizer 1306 are located between optical assembly 1310 and light sensor array 1312. Yet further alternatively, main polarizer 1308 is located between three-dimensional object 1328 and periscope assembly 1302, while right polarizer 1304 and left polarizer 1306 are located between optical assembly 1310 and light sensor array 1312.

Still further alternatively, right polarizer 1304 and left polarizer 1306 are located between three-dimensional object 1328 and main polarizer 1308. Main polarizer 1308 is located between right polarizer 1304 and left polarizer 1306 on one side and periscope assembly 1302 on the other side.

Yet further alternatively, main polarizer 1308 is located between three-dimensional object 1328 on one side and right polarizer 1304 and left polarizer 1306 on the other side. Right polarizer 1304 and left polarizer 1306 are located between main polarizer 1308 and periscope assembly 1302.

Still further alternatively, right polarizer 1304 and left polarizer 1306 are located between periscope assembly 1302 and main polarizer 1308. Main polarizer 1308 is located between right polarizer 1304 and left polarizer 1306 on one side and optical assembly 1310 on the other side.

Yet further alternatively, main polarizer 1308 is located between periscope assembly 1302 on one side and right polarizer 1304 and left polarizer 1306 on the other side. Right polarizer 1304 and left polarizer 1306 are located between main polarizer 1308 and optical assembly 1310.

Still further alternatively, right polarizer 1304 and left polarizer 1306 are located between optical assembly 1310 and main polarizer 1308. Main polarizer 1308 is located between right polarizer 1304 and left polarizer 1306 on one side and light sensor array 1312 on the other side.

Yet further alternatively, main polarizer 1308 is located between optical assembly 1310 on one side and right polarizer 1304 and left polarizer 1306 on the other side. Right polarizer 1304 and left polarizer 1306 are located between main polarizer 1308 and light sensor array 1312.

Further alternatively, the polarization angle of main polarizer 1308 is fixed and the polarization angle of right polarizer 1304 and left polarizer 1306 can be changed. In this case, controller 1314 is coupled with right polarizer 1304 and left polarizer 1306 instead of main polarizer 1308 and hence, controller 1314 controls the angle of both right polarizer 1304 and left polarizer 1306. The polarization angles of right polarizer 1304 and left polarizer 1306 are changed substantially simultaneously and alternately by substantially 90 degrees each time, while the angle there between is substantially 90 degrees at all times.

According to another aspect of the disclosed technique, the image differentiator includes a combination of polarizers and polarization rotating cells. Each polarization rotating cell sequentially changes the polarization angle of light which exits each of two polarizers.

According to one embodiment, the image differentiator includes a front right polarizer, a front left polarizer, a polarization rotating cell and a main polarizer. The front right polarizer and the front left polarizer are located in the right channel and the left channel, respectively. The polarization rotating cell is located in the common path. The main polarizer is located in the common path between the polarization rotating cell and the light sensor array. The polarization angle of the front right polarizer is substantially equal to the polarization angle of the main polarizer, while the polarization angle of the front left polarizer is approximately 90 degrees away from that of the main polarizer. The polarization rotating cell receives light from both the front right polarizer and the front left polarizer. The polarization rotating cell is coupled with the controller.

A polarization rotating cell is generally in form of a crystal which changes the polarization angle of the incoming light by a selected value. In the present example, the polarization rotating cell alternates between two states. At the first state, the polarization rotating cell rotates any light incident thereon by a zero angle, thereby leaving the polarization angle of that incident light, unchanged. At the second state, the polarization rotating cell rotates any light incident thereon, by a substantially right angle (i.e., 90 degrees).

When the polarization rotating cell is in the first state, the polarization rotating cell leaves the polarization of the light exiting the front right polarizer and the front left polarizer unchanged. Since the polarization of the front right polarizer is substantially equal to the polarization of the main polarizer, the main polarizer admits the light which previously exited the front right polarizer. Since the polarization of the front left polarizer is substantially rotated at 90 degrees away from the polarization of the main polarizer, the main polarizer blocks the light which previously exited the front left polarizer. Thus, the main polarizer admits the right side view image of the three-dimensional object to the light sensor array, while the main polarizer blocks the left side view image of the three-dimensional object.

When the polarization rotating cell is in the second state, the polarization rotating cell rotates the polarization of the light received from the front right polarizer and from the front left polarizer, by substantially 90 degrees. In this case, the polarization of the light which previously exited the front left polarizer, is rotated to be substantially equal to the polarization angle of the main polarizer. Furthermore, the polarization of the light which exited the front right polarizer is rotated to be at substantially 90 degrees away from the polarization of the main polarizer. The main polarizer admits the light which previously exited the front left polarizer, while the main polarizer blocks the light which previously exited the front right polarizer. Thus, the main polarizer admits the left side view image of the three-dimensional object to the light sensor array, while the main polarizer blocks the right side view image of the three-dimensional object. The controller enables the light sensor array to detect the right side view image and the left side view image of the three-dimensional object, according to the rotating state of the polarization rotating cell.

According to another embodiment, a right polarization rotating cell is located between the front right polarizer and the main polarizer, in the right channel and a left polarization rotating cell is located between the front left polarizer and the main polarizer, in the left channel. The main polarizer is located in the common path, between the right polarization rotating cell and the left polarization rotating cell on one side and the light sensor array on the other. The front right polarizer, the front left polarizer and the main polarizer are static polarizers. The polarization angles of the front right polarizer, the front left polarizer and the main polarizer are substantially equal. The right polarization rotating cell and the left polarization rotating cell are coupled with the controller, which alternately provides two states of operation.

In the first state of operation, the controller sets the rotation angle of the right polarization rotating cell to zero degrees and the rotation angle of the left polarization rotating cell to 90 degrees. Accordingly, the polarization of the light which previously exited the front right polarizer remains substantially unchanged, while the polarization of the light which previously exited the front left polarizer is changed by a substantially right angle. The main polarizer admits the light which previously exited the front right polarizer, while the main polarizer blocks the light previously exited the front left polarizer. Thus, the main polarizer admits the right side view image of the three-dimensional object to the light sensor array, while blocking the left side view image of the three-dimensional object.

In the second state of operation, the controller sets the rotation angle of the left polarization rotating cell to zero degrees and the rotation angle of the right polarization rotating cell to 90 degrees. Accordingly, the polarization of the light which previously exited the front left polarizer remains substantially unchanged, while the polarization of the light which previously exited the front right polarizer is changed by substantially 90 degrees. The main polarizer admits the light which previously exited the front left polarizer, while the main polarizer blocks the light previously exited the front right polarizer. Thus, the main polarizer admits the left side view image of the three-dimensional object to the light sensor array, while the main polarizer blocks the right side view image of the three-dimensional object. The controller enables the light sensor array to detect the right side view image and the left side view image of the three-dimensional object, according to the rotating states of the right polarization rotating cell and the left polarization rotating cell.

According to another embodiment, the main polarizer is eliminated, the front right polarizer and the front left polarizer are static polarizers and the polarization angle of the front right polarizer is substantially 90 degrees away from the polarization angle of the front left polarizer. In addition a polarized light source is employed, which is coupled with the controller. The polarized light source alternately illuminates the three-dimensional object with light at a first polarization angle and at a second polarization angle. The first polarization angle of the illuminating light is substantially equal to the polarization angle of the front right polarizer and the second polarization angle of the illuminating light is substantially equal to the polarization angle of the front left polarizer.

When the polarized light source illuminates the three-dimensional object at the polarization angle of the front right polarizer, the periscope assembly directs the right side view image of the three-dimensional object to the front right polarizer, substantially at the polarization angle of the front right polarizer. Simultaneously, the periscope assembly directs the left side view image of the three-dimensional object to the front left polarizer, substantially at the polarization angle of the front right polarizer. Since the polarization angle of the right side view image is substantially equal to the polarization angle of the front right polarizer, the front right polarizer admits the right side view image of the three-dimensional object to the light sensor array, through the optical assembly. Since the polarization angle of the left side view image is substantially 90 degrees away from the polarization angle of the front left polarizer, the front left polarizer blocks the left side view image of the three-dimensional object.

When the polarized light source illuminates the three-dimensional object at the polarization angle of the front left polarizer, the periscope assembly directs the left side view image of the three-dimensional object to the front left polarizer, substantially at the polarization angle of the front left polarizer. Simultaneously, the periscope assembly directs the right side view image of the three-dimensional object to the front right polarizer, substantially at the polarization angle of the front left polarizer. Since the polarization angle of the left side view image is substantially equal to the polarization angle of the front left polarizer, the front left polarizer admits the left side view image of the three-dimensional object to the light sensor array, through the optical assembly. Since the polarization angle of the right side view image is substantially 90 degrees away from the polarization angle of the front right polarizer, the front right polarizer blocks the left side view image of the three-dimensional object. The controller enables the light sensor array to detect the right side view image and the left side view image of the three-dimensional object, according to the illuminating state of the polarized light source.

It is noted that in this case, the three-dimensional object is illuminated only with light at a selected polarization angle at each state of the polarized light source. Thus, the three-dimensional object is heated substantially less and the physical properties thereof remain substantially stable.

Figure 32:
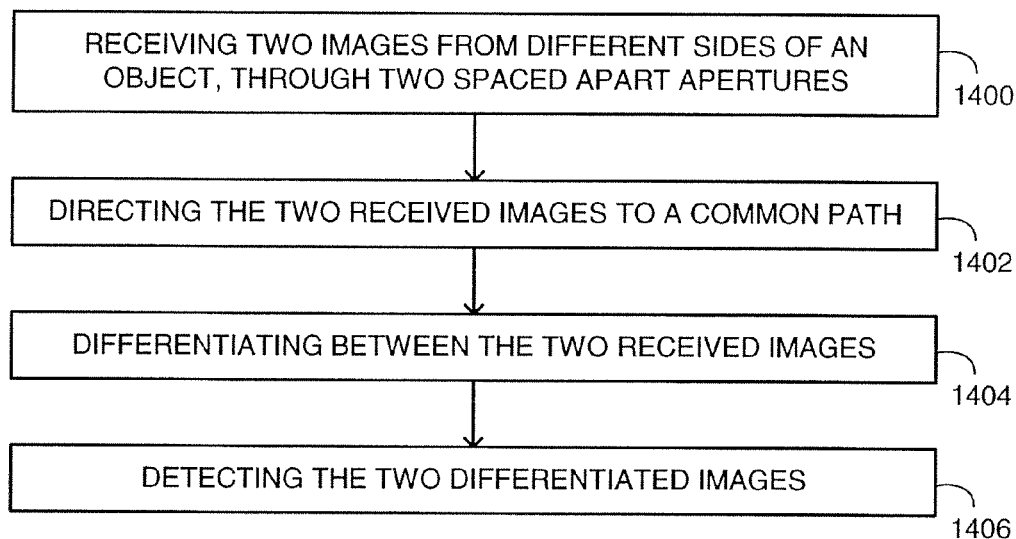
FIG. 32 is a schematic illustration of a method for operating a stereoscopic imaging apparatus, operative in accordance with another embodiment of the disclosed technique.

Reference is now made to FIG. 32, which is a schematic illustration of a method for operating a stereoscopic imaging apparatus, operative in accordance with another embodiment of the disclosed technique. In step 1400, two images are received from different sides of an object, through two spaced apart apertures. With reference to FIG. 28A, periscope assembly 1102 receives a right side view image and a left side view image of three-dimensional object 1118.

In step 1402, the two received images are directed to a common path. With reference to FIG. 28A, periscope assembly 1102 directs the right side view image as light beams 1120C and 1122C, and the left side view image as light beams 1124C and 1126C, through optical assembly 1104, to lenticular lens layer 1106.

In step 1404, the two received images are differentiated. With reference to FIG. 28A, lenticular lens layer 1106 differentiates between the right side view image and the left side view image of three-dimensional object 1118, and directs each differentiated image to light sensor array 1108. Light sensor array 1108, then detects the differentiated images (step 1406).

According to another embodiment of the disclosed technique, the periscope assembly moves between a retracted position and an extended position. Thus, the endoscope is entered into the body of the patient while the periscope assembly is retracted, thereby assuming a narrow shape, capable of entering through narrow passages. When the endoscope is located in a selected region within the body of the patient, the periscope assembly moves to an extended position, thereby separating apart the apertures which receive a right side view and a left side view of the selected region. The periscope, then transfers substantially distinct right side view and left side view images of the selected region, to an image detector via an optical assembly.

Figure 33A:
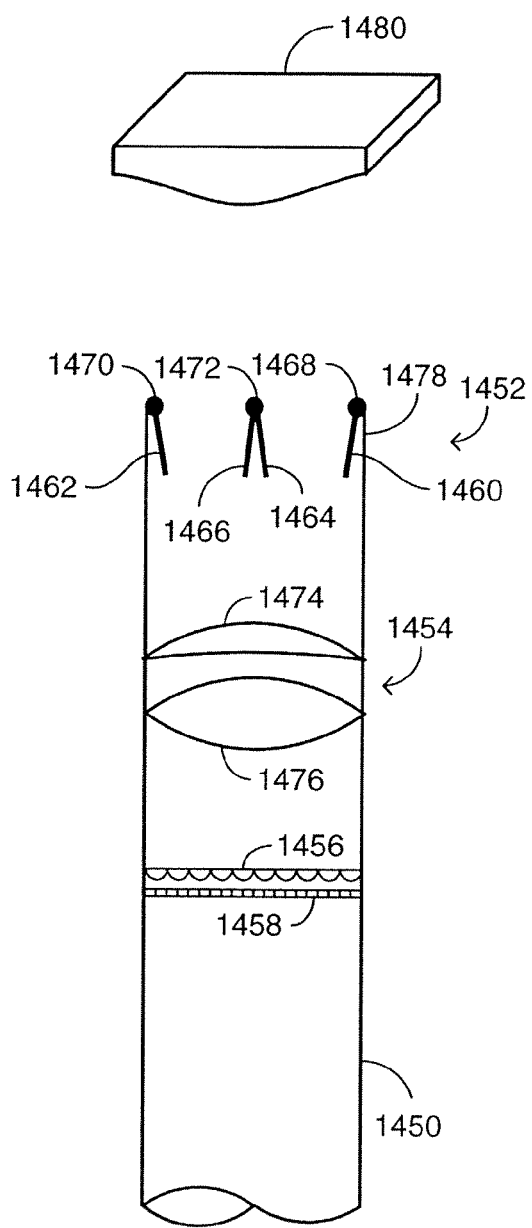
FIG. 33A is a schematic illustration of an endoscope with a periscope assembly thereof in a retracted mode, constructed and operative in accordance with a further embodiment of the disclosed technique.
Figure 33B:
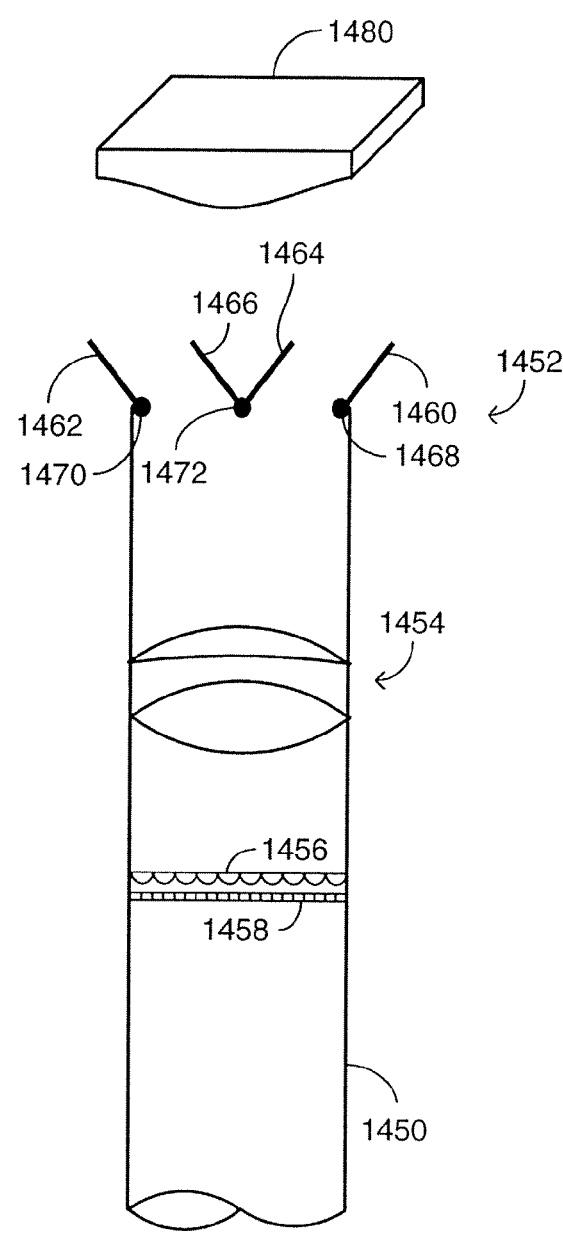
FIG. 33B is a schematic illustration of the periscope of the endoscope of FIG. 33A, in an extended mode.

Reference is now made to FIGS. 33A and 33B. FIG. 33A is a schematic illustration of an endoscope with a periscope assembly thereof in a retracted mode, generally referenced 1450, constructed and operative in accordance with a further embodiment of the disclosed technique. FIG. 33B is a schematic illustration of the periscope of the endoscope of FIG. 33A, in an extended mode.

Endoscope 1450 includes a periscope assembly 1452, an optical assembly 1454, a lenticular lens layer 1456, and a light sensor array 1458. Periscope assembly 1452 includes a right mirror 1460, a left mirror 1462, a right center mirror 1464, a left center mirror 1466, and hinges 1468, 1470 and 1472. Optical assembly 1454 includes a plurality of lenses 1474 and 1476.

Periscope assembly 1452 is located at a distal end 1478 of endoscope 1450. Optical assembly 1454 is located between periscope assembly 1452 and lenticular lens array 1456. Lenticular lens array 1456 is located between optical assembly 1454 and light sensor array 1458. Right mirror 1460 and left mirror 1462 can rotate about hinges 1468 and 1470, respectively. Right center mirror 1464 and left center mirror 1466 can rotate about hinge 1472.

With reference to FIG. 33B, right mirror 1460 and left center mirror 1466 rotate clockwise about hinges 1468 and 1472, respectively. Left mirror 1462 and right center mirror 1464 rotate counterclockwise about hinges 1470 and 1472, respectively. Thus, periscope assembly 1452 moves to an extended position. Right mirror 1460 and left mirror 1462 receive a right side view and a left side view, respectively, of a three-dimensional object 1480. Right center mirror 1464 and left center mirror 1466 reflect a right side view image and a left side view image of three-dimensional object 1480, as reflected from right mirror 1460 and left mirror 1462, respectively, to optical assembly 1454. Optical assembly 1454 focuses the right side view image and the left side view image of three-dimensional object 1480, on lenticular lens layer 1456. Lenticular lens layer 1456 differentiates between the right side view image and the left side view image, and the respective detection elements of light sensor array 1458 detect the right side view image and the left side view image of three-dimensional object 1480.

Figure 34A:
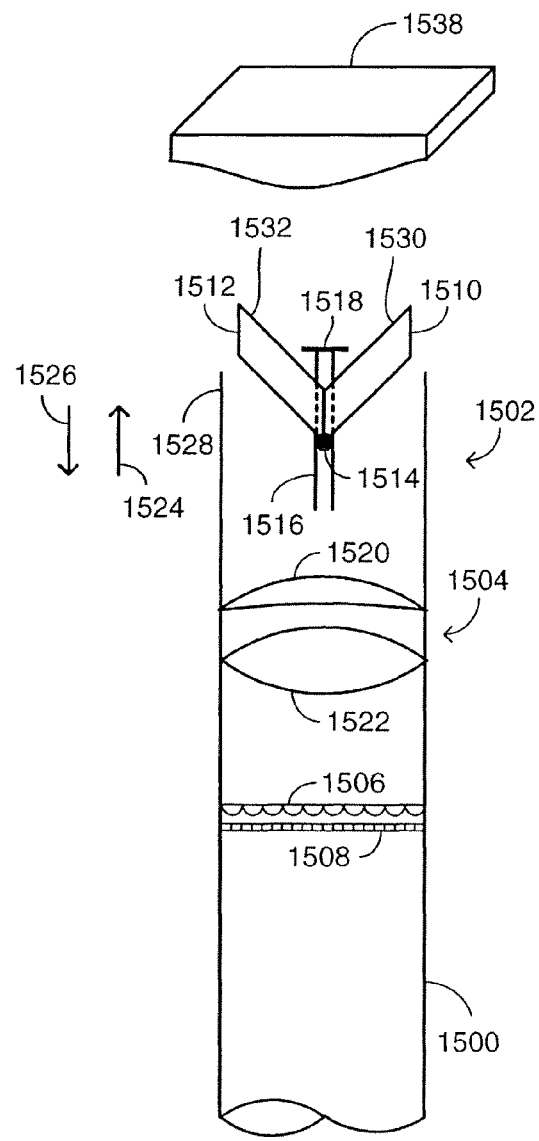
FIG. 34A is a schematic illustration of an endoscope with a periscope assembly thereof in a retracted mode, constructed and operative in accordance with another embodiment of the disclosed technique.
Figure 34B:
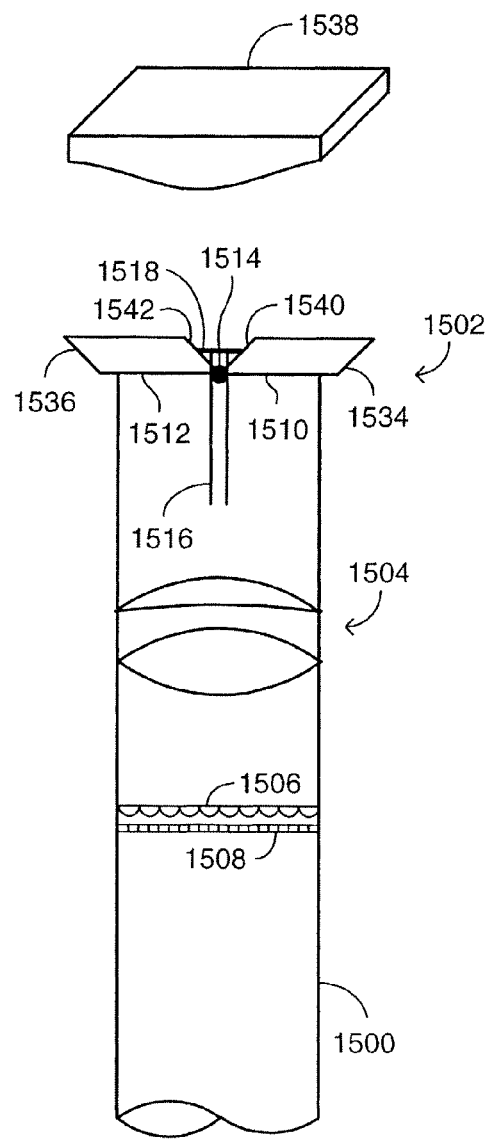
FIG. 34B is a schematic illustration of the periscope assembly of the endoscope of FIG. 34A, in an extended mode.

Reference is now made to FIGS. 34A and 34B. FIG. 34A is a schematic illustration of an endoscope with a periscope assembly thereof in a retracted mode, generally referenced 1500, constructed and operative in accordance with another embodiment of the disclosed technique. FIG. 34B is a schematic illustration of the periscope assembly of the endoscope of FIG. 34A, in an extended mode.

Endoscope 1500 includes a periscope assembly 1502, an optical assembly 1504, a lenticular lens layer 1506, and a light sensor array 1508. Periscope assembly 1502 includes a right prism 1510, a left prism 1512, a hinge 1514, a rail 1516 and a stop 1518. Optical assembly 1504 includes a plurality of lenses 1520 and 1522. Each of right prism 1510 and left prism 1512 is a prism whose longitudinal cross section is a parallelogram. Right prism 1510 and left prism 1512 can rotate about hinge 1514. Hinge 1514 can slide within rail 1516 in directions designated by arrows 1524 and 1526. Stop 1518 is coupled with rail 1516. Periscope assembly 1502 is located at a distal end 1528 of endoscope 1500. Optical assembly 1504 is located between periscope assembly 1502 and lenticular lens layer 1506. Lenticular lens layer 1506 is located between optical assembly 1504 and light sensor array 1508.

With reference to FIG. 34B, hinge 1514 slides within rail 1516 in direction 1524, surfaces 1530 and 1532 of right prism 1510 and left prism 1512, respectively, make contact with stop 1518 and thus, right prism 1510 and left prism 1512 move to an extended position. In this position, reflective surfaces 1534 and 1536 of right prism 1510 and left prism 1512, respectively, located distal to hinge 1514, receive a right side view image and a left side view image of a three-dimensional object 1538. Reflective surface 1540 and 1542 of right prism 1510 and left prism 1512, respectively, located proximal to hinge 1514, reflect the right side view image and the left side view image, as reflected from reflective surfaces 1534 and 1536, respectively, to optical assembly 1504.

Optical assembly 1504 focuses the right side view image and the left side view image of three-dimensional object 1538, on lenticular lens layer 1506. Lenticular lens layer 1506 differentiates between the right side view image and the left side view image, and the respective detection elements of light sensor array 1508 detect the right side view image and the left side view image of three-dimensional object 1538. When hinge 1514 moves in direction 1526, surfaces 1530 and 1532 make contact with stop 1518 and right prism 1510 and left prism 1512 move back to the retracted position of FIG. 34A. It is noted that instead of lenticular lens layer 1506, other types of image differentiators can be employed, such as a pair of filters, a multi-wavelength rotating disk, a partially-transparent rotating disk, a pair of polarizers, a multiple aperture, and the like.

Figure 35A:
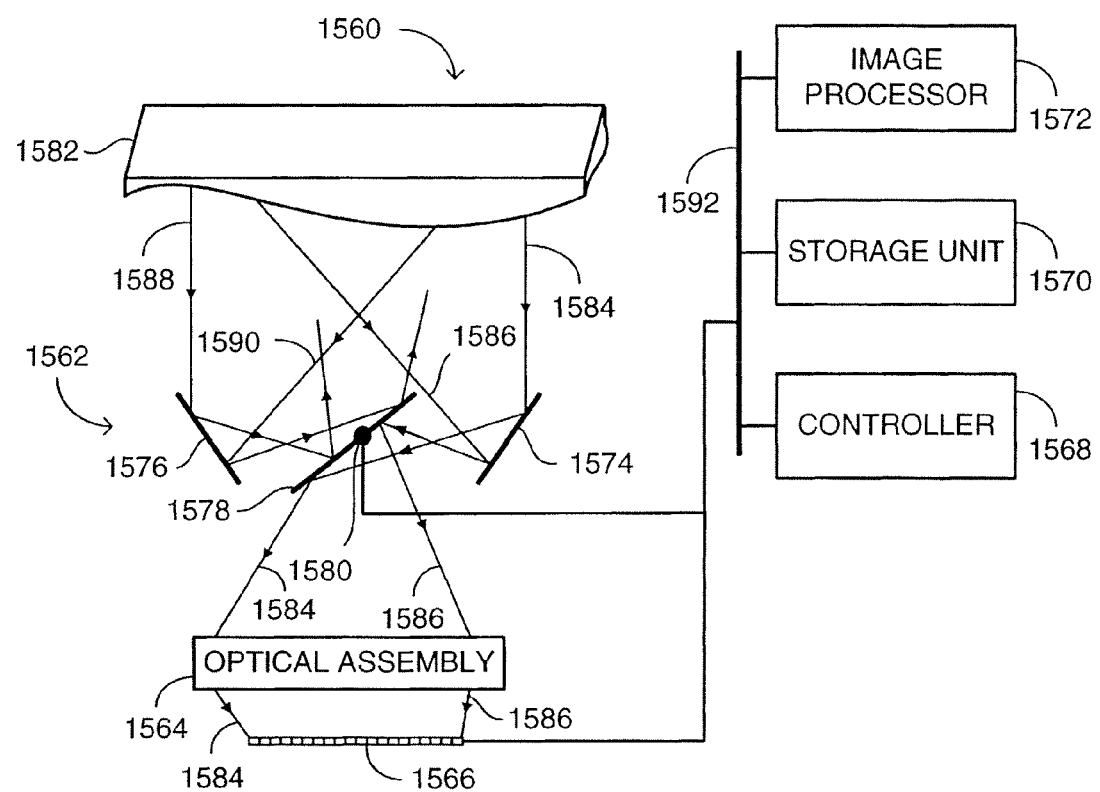
FIG. 35A is a schematic illustration of a stereoscopic imaging apparatus, constructed and operative in accordance with a further embodiment of the disclosed technique.
Figure 35B:
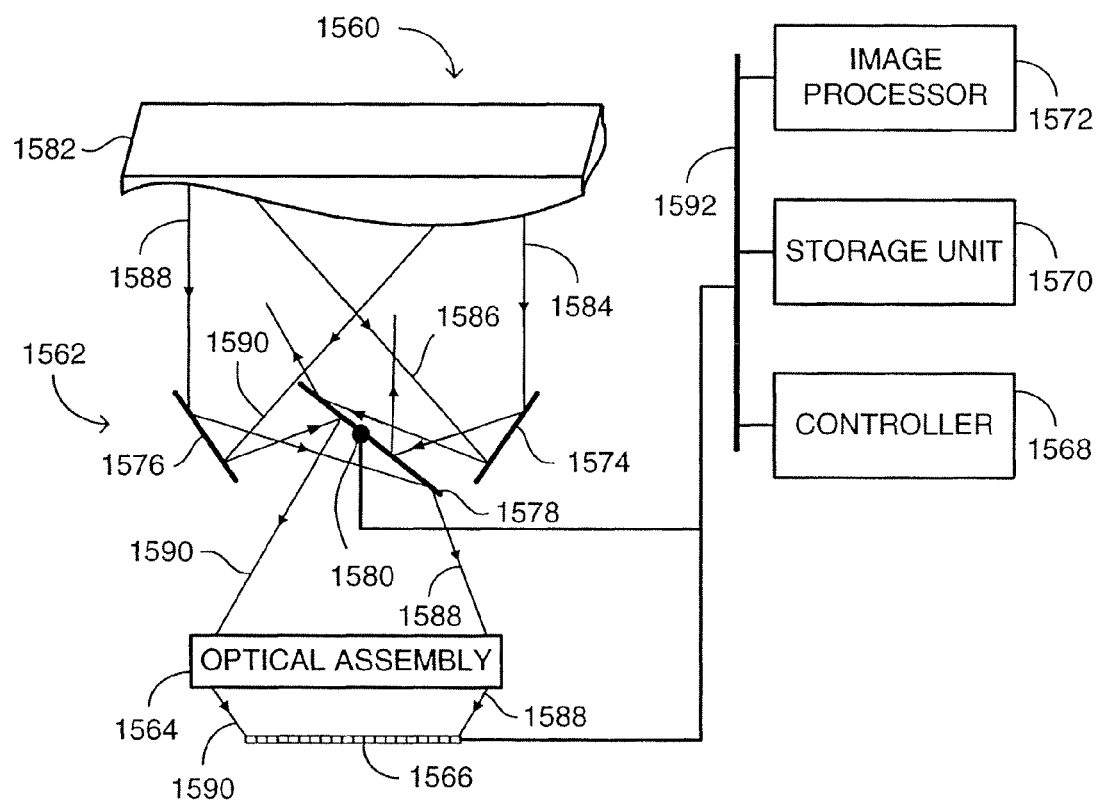
FIG. 35B is a schematic illustration of the apparatus of FIG. 35A, in which the periscope assembly thereof is in a different mode than that of FIG. 35A.

Reference is now made to FIGS. 35A and 35B. FIG. 35A is a schematic illustration of a stereoscopic imaging apparatus, generally referenced 1560, constructed and operative in accordance with a further embodiment of the disclosed technique. FIG. 35B is a schematic illustration of the apparatus of FIG. 35A, in which the periscope assembly thereof is in a different mode than that of FIG. 35A.

Apparatus 1560 includes a periscope assembly 1562, an optical assembly 1564, a light sensor array 1566, a controller 1568, a storage unit 1570 and an image processor 1572. Periscope assembly 1562 includes a right mirror 1574, a left mirror 1576, a rotating mirror 1578 and a hinge 1580. One side of rotating mirror 1578 is reflective and the other side thereof is non-reflective. Periscope assembly 1562 is located between a three-dimensional object 1582 and optical assembly 1564. Optical assembly 1564 is located between periscope assembly 1562 and light sensor array 1566. Hinge 1580 is coupled with a moving element (not shown), such as a piezoelectric element, a pulling force of a cable against a spring, and the like. The moving element, light sensor array 1566, storage unit 1570 and image processor 1572 are interconnected via a bus 1592.

Right mirror 1574 is oriented at a slanted angle with respect to three-dimensional object 1582 and at the right side of three-dimensional object 1582, such that right mirror 1574 receives a right side view image of three-dimensional object 1582. This slanted angle is preferably close to 45 degrees. Left mirror 1576 is oriented at another slanted angle, opposite to the slanted angle of right mirror 1574 and at the left side of three-dimensional object 1582. Left mirror 1576 receives a left side view image of three-dimensional object 1582.

The moving element alternately rotates rotating mirror 1578 about hinge 1580, between two positions. At one position, rotating mirror 1578 is oriented at an angle substantially parallel to the slanted angle of right mirror 1574. In this position, the reflective side of rotating mirror 1578 faces right mirror 1574 while the non-reflective side of rotating mirror 1578 faces left mirror 1576. At another position, rotating mirror 1578 is oriented at an angle substantially parallel to the slanted angle of left mirror 1576. In this position, the reflective side of rotating mirror 1578 faces left mirror 1576 while the non-reflective side of rotating mirror 1578 faces right mirror 1574.

With reference to FIG. 35A, rotating mirror 1578 is oriented at an angle substantially parallel to right mirror 1574 and approximately at 90 degrees relative to the orientation of left mirror 1576, such that the reflective side of rotating mirror 1578 faces right mirror 1574. Right mirror 1574 receives light beams 1584 and 1586, which include information respective of the right side view image of three-dimensional object 1582. Rotating mirror 1578 reflects light beams 1584 and 1586, as reflected by right mirror 1574, to optical assembly 1564. Optical assembly 1564 focuses light beams 1584 and 1586 on light sensor array 1566. Controller 1568 enables light sensor array 1566 to detect a right side view image of three-dimensional object 1582, according to the position of rotating mirror 1578. Controller 1568 stores this right side view image in storage unit 1570.

Left mirror 1576 receives light beams 1588 and 1590, which include information respective of the left side view image of three-dimensional object 1582. Since the non-reflective side of rotating mirror 1578 is facing left mirror 1576, this non-reflective side absorbs light beams 1588 and 1590. Thus, light beams 1588 and 1590 reach neither optical assembly 1564 nor light sensor array 1566, nor is reflected or refracted light incident upon the three-dimensional object 1582, and light sensor array 1566 does not detect the left side view image of three-dimensional object 1582.

With reference to FIG. 35B, rotating mirror 1578 rotates 90 degrees counterclockwise relative to the position illustrated in FIG. 35A. In the position illustrated in FIG. 35B, rotating mirror 1578 is oriented at an angle substantially parallel to left mirror 1576 and approximately at 90 degrees relative to the orientation of right mirror 1574. The reflective side of rotating mirror 1578 faces left mirror 1576 and the non-reflective side thereof faces right mirror 1574. Rotating mirror 1578 reflects light beams 1588 and 1590, as reflected by left mirror 1576, to optical assembly 1564. Optical assembly 1564 focuses light beams 1588 and 1590 on light sensor array 1566. Controller 1568 enables light sensor array 1566 to detect a left side view image of three-dimensional object 1582, according to the position of rotating mirror 1578. Controller 1568 stores this left side view image in storage unit 1570.

Since the non-reflective side of rotating mirror 1578 faces right mirror 1574, this non-reflective side absorbs light beams 1584 and 1586. Thus, light beams 1584 and 1586 reach neither optical assembly 1564 nor light sensor array 1566, nor is reflected or refracted light incident upon the three-dimensional object 1582, and light sensor array 1566 does not detect the right side view image of three-dimensional object 1582. Rotating mirror 1578, then rotates 90 degrees clockwise to the position illustrated in FIG. 35A and provides another right side view image of three-dimensional object 1582 to light sensor array 1566. Image processor 1572 provides a video signal for a stereoscopic display, such as stereoscopic display 214 (FIG. 2), by retrieving the right side and left side view images from storage unit 1570 and processing them.

Alternatively, an optical element, such as an optical diaphragm, prism, mirror and the like, replaces rotating mirror 1578. Half of the optical diaphragm is transparent and the other half is opaque. The optical diaphragm oscillates about an axis, by an electronic element, such as piezoelectric element, and the like, such that the transparent and the opaque portions of the diaphragm are alternately located above right mirror 1574 and left mirror 1576.

According to another aspect of the disclosed technique, two fiberscopes are employed whose inlets are substantially spaced apart relative to the outlets thereof. One fiberscope obtains a right side view image of the three-dimensional object, while the other fiberscope obtains a left side view image of the three-dimensional object.

Figure 36:
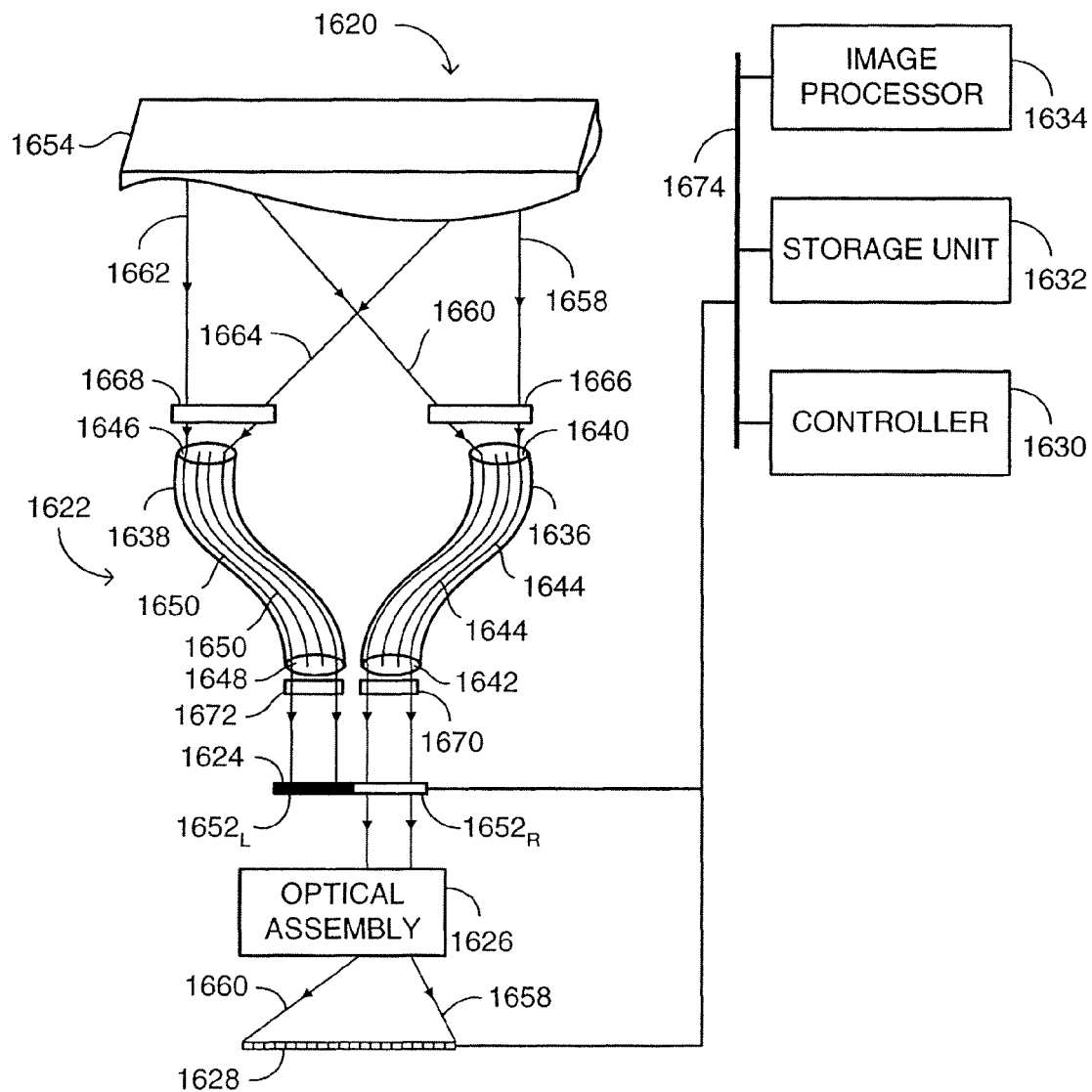
FIG. 36 is a schematic illustration of a stereoscopic imaging apparatus, constructed and operative in accordance with another embodiment of the disclosed technique.

Reference is now made to FIG. 36, which is a schematic illustration of a stereoscopic imaging apparatus, generally referenced 1620, constructed and operative in accordance with another embodiment of the disclosed technique. Apparatus 1620 includes inlet lenses 1666 and 1668, a light directing assembly 1622, outlet lenses 1670 and 1672, a multiple aperture 1624, an optical assembly 1626, a light sensor array 1628, a controller 1630, a storage unit 1632 and an image processor 1634. Light directing assembly 1622 includes a right fiberscope 1636 and a left fiberscope 1638.

A fiberscope is a flexible longitudinal element, which is generally employed for obtaining an image of an object which is obstructed by other objects and can not be viewed directly. The fiberscope includes a substantially large number of fibers. One end of each fiber receives the image of a substantially small portion of the object at the inlet of the fiberscope and conveys this image to the other end of the same fiber, at the outlet of the fiberscope. Thus, the plurality of the fibers, together provide a complete image of the object at the outlet of the fiberscope, duplicating the image detected by the fiberscope at the inlet thereof.

The relative positions of the ends of the fibers at the outlet of the fiberscope, are the same as the relative positions of the fibers at the inlet of the fiberscope (i.e., substantially no twist of the fibers along the length of the fiberscope is allowed). Otherwise, the image of the object at the outlet of the fiberscope will be skewed and different from the image of the object as viewed by the inlet of the fiberscope.

Right fiberscope 1636 includes an image inlet 1640, an image outlet 1642 and a plurality of fibers 1644. Left fiberscope 1638 includes an image inlet 1646, an image outlet 1648 and a plurality of fibers 1650. Multiple aperture 1624 includes a right aperture $1652_R$ and a left aperture $1652_L$. Multiple aperture 1624 is similar to multiple aperture 804, as described herein above in connection with FIG. 20A. Multiple aperture 1624, light sensor array 1628, controller 1630, storage unit 1632 and image processor 1634 are interconnected via a bus 1674. Controller 1630 controls the alternate closure and opening of right aperture $1652_R$ and left aperture $1652_L$.

Light directing assembly 1622 is located between a three-dimensional object 1654 and multiple aperture 1624. Multiple aperture 1624 is located between light directing assembly 1622 and optical assembly 1626. Optical assembly 1626 is located between multiple aperture 1624 and light sensor array 1628. Inlet lenses 1666 and 1668 are located between three-dimensional object 1654 and image inlets 1640 and 1646, respectively. Outlet lenses 1670 and 1672 are located between multiple aperture 1624 and image outlets 1642 and 1648, respectively.

Right fiberscope 1636 and left fiberscope 1638 are bent, such that image inlets 1640 and 1646 are spaced apart and image inlets 1642 and 1648 are located close together. In this manner, right fiberscope 1636 obtains an image of three-dimensional object 1654 from the right side thereof, which is substantially different from another image obtained by left fiberscope 1638, from the left side of three-dimensional object 1654.

Light beams 1658 and 1660 include information respective of the right side view image of three-dimensional object 1654. Inlet lens 1666 focuses light beams 1658 and 1660 on image inlet 1640. Fibers 1644 convey light beams 1658 and 1660 to image outlet 1642. Outlet lens 1670 focuses light beams 1658 and 1660 on right aperture $1652_R$. Since right aperture $1652_R$ is open, light beams 1658 and 1660 reach optical assembly $1626_R$, optical assembly $1626_R$ focuses light beams 1658 and 1660 on light sensor array 1628. Controller 1630 enables light sensor array 1628 to detect a right side view image of three-dimensional object 1654, according to the state of multiple aperture 1624 (i.e., when right aperture $1652_R$ is open). Controller 1630 stores this right side view image in storage unit 1632.

Light beams 1662 and 1664 include information respective of the left side view image of three-dimensional object 1654. Inlet lens 1668 focuses light beams 1662 and 1664 on image inlet 1646. Fibers 1650 convey light beams 1662 and 1664 to image outlet 1648. Outlet lens 1672 focuses light beams 1662 and 1664 on left aperture $1652_L$. Since left aperture $1652_L$ is closed, light beams 1662 and 1664 are blocked and light sensor array 1628 does not detect the left side view image of three-dimensional object 1654.

In another mode of apparatus 1620 (not shown), right aperture $1652_R$ is closed and left aperture $1652_L$ is open. Thus, left aperture $1652_L$ allows light beams 1662 and 1664 to pass there through and reach optical assembly 1626. Optical assembly 1626 focuses light beams 1662 and 1664 on light sensor array 1628. Controller 1630 enables light sensor array 1628 to detect a left side view image of three-dimensional object 1654, according to the state of multiple aperture 1624 (i.e., when left aperture $1652_L$ is open). Controller 1630 stores this left side view image in storage unit 1632. Image processor 1634 produces a video signal for a stereoscopic display, such as stereoscopic display 214 (FIG. 2), by retrieving these images from storage unit 1632 and processing them.

According to another aspect of the disclosed technique, a plurality of an arm of Y-junction fibers are spaced from a plurality of another arm of the Y-junction fibers. The plurality of each arm of the Y-junction fibers alternately transfer an image of a three-dimensional object, as viewed from the respective side, to the plurality of the legs of the Y-junction fibers.

Figure 37A:
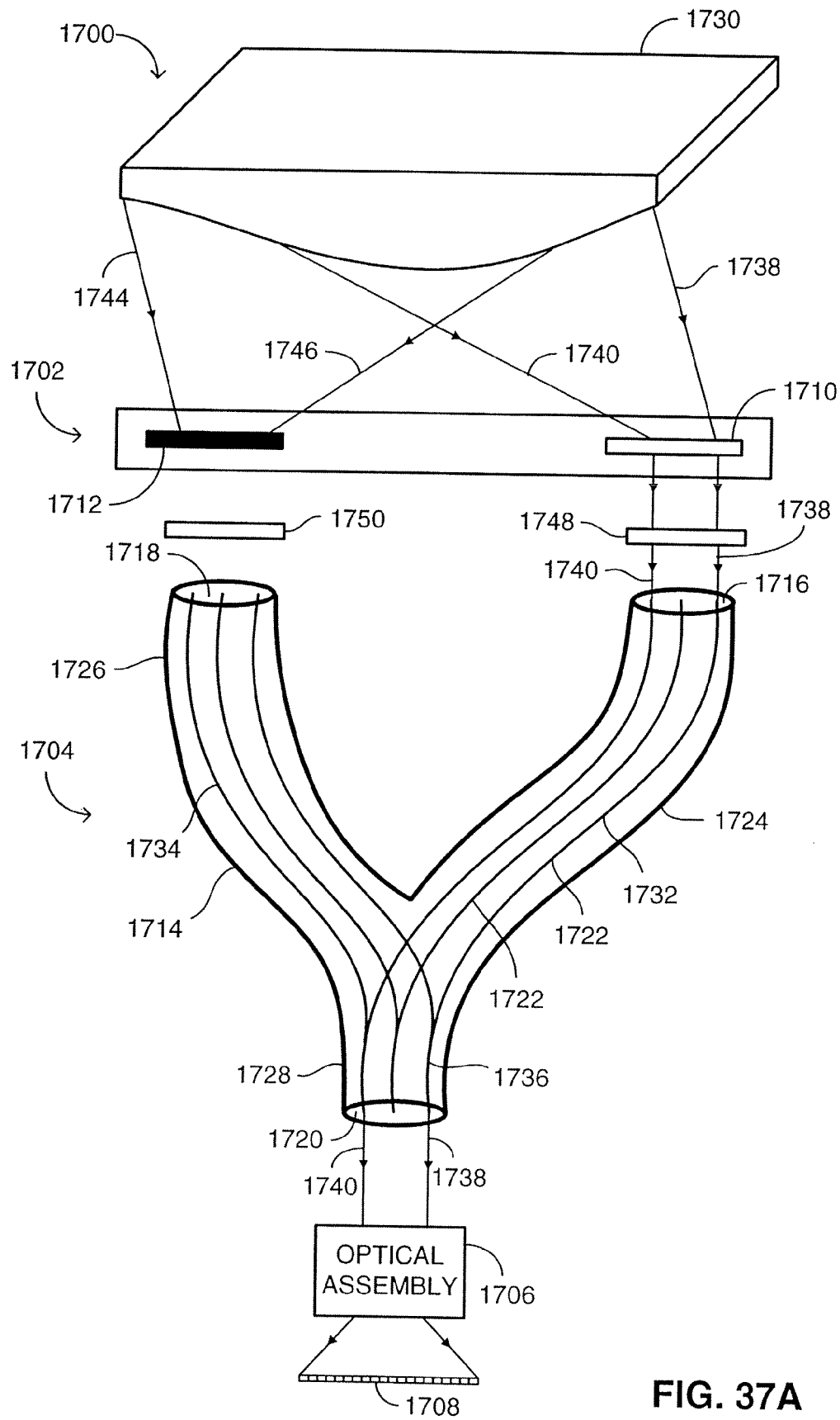
FIG. 37A is a schematic illustration of a stereoscopic imaging apparatus, constructed and operative in accordance with a further embodiment of the disclosed technique.
Figure 37B:
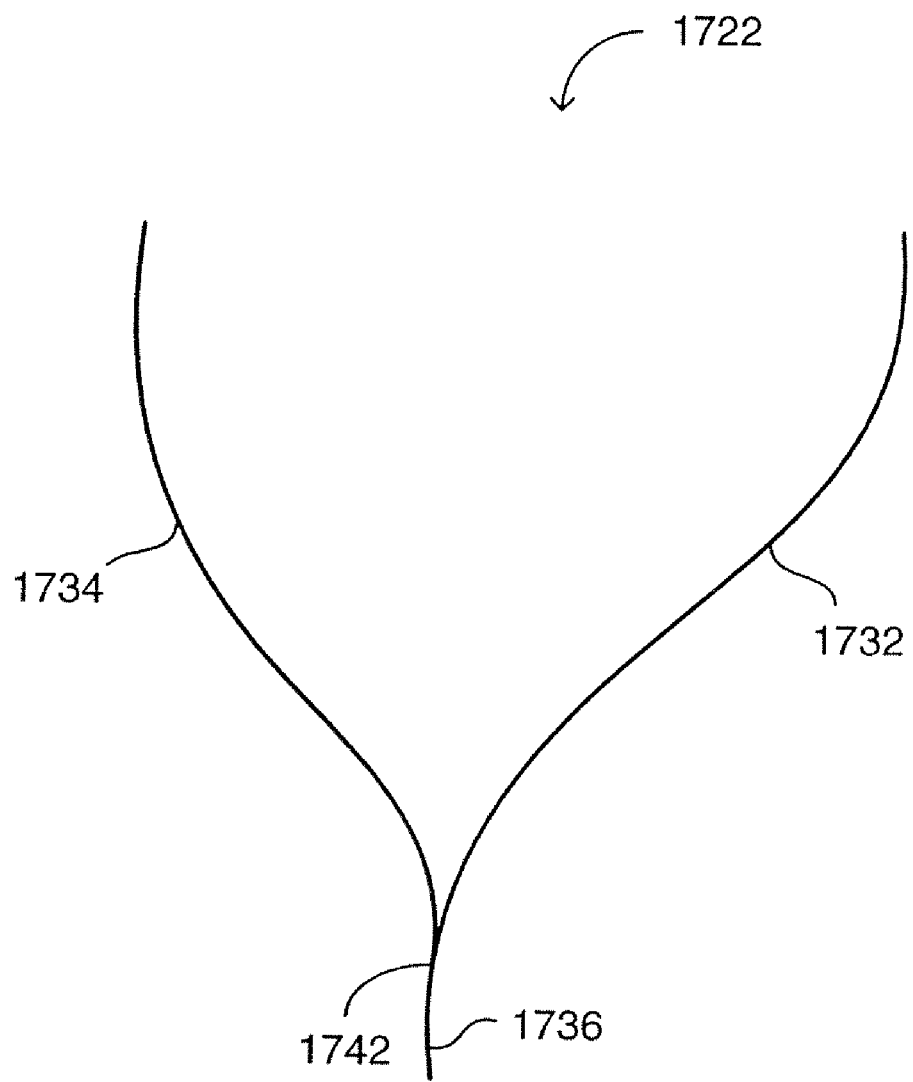
FIG. 37B is a schematic illustration of a split fiber of the light directing assembly of the apparatus of FIG. 37A.

Reference is now made to FIGS. 37A and 37B. FIG. 37A is a schematic illustration of a stereoscopic imaging apparatus, generally referenced 1700, constructed and operative in accordance with a further embodiment of the disclosed technique. FIG. 37B is a schematic illustration of a split fiber of the light directing assembly of the apparatus of FIG. 37A.

Apparatus 1700 includes an image differentiator 1702, a right lens 1748, a left lens 1750, a light directing assembly 1704, an optical assembly 1706 and a light sensor array 1708. Image differentiator 1702 can include a right side filter 1710 and a left side filter 1712, similar to right side filter 1202 and left side filter 1204, respectively, as described herein above in connection with FIG. 30A. Alternatively, image differentiator 1702 is a multiple aperture such as multiple aperture 1154 (FIG. 29A).

If image differentiator 1702 is a filter type image differentiator, then image differentiator 1702 includes right side filter 1710 and left side filter 1712. In this case, apparatus 1700 further includes two illuminators (not shown) similar to illuminators 1212 and 1214 as described herein above in connection with FIG. 30A. The two illuminators are coupled with a controller, such as controller 1216 (FIG. 30A). In the foregoing discussion, image differentiator 1702 is a filter type differentiator.

Light directing assembly 1704 includes a sleeve 1714, a right inlet 1716, a left inlet 1718, an outlet 1720 and a plurality of split fibers 1722. Sleeve 1714 includes a right section 1724, a left section 1726 and a common section 1728.

Image differentiator 1702 is located between a three-dimensional object 1730, and right lens 1748 and left lens 1750. Right lens 1748 is located in front of right inlet 1716 and it produces a right side view image of three-dimensional object 1730 on right inlet 1716. Left lens 1750 is located in front of left inlet 1718 and it produces a left side view image of three-dimensional object 1730 on left inlet 1718. Light directing assembly 1704 is located between right lens 1748 and left lens 1750, on the one side, and optical assembly 1706, on the other side. Optical assembly 1706 is located between light directing assembly 1704 and light sensor array 1708.

With reference to FIG. 37B, split fiber 1722 is in the form of a Y-junction. Split fiber 1722 includes a right arm 1732, a left arm 1734 and a common arm 1736. Right arm 1732 and left arm 1734 merge into common arm 1736, such that light can enter common arm 1736 through both right arm 1732 and left arm 1734. Sleeve 1714 is constructed in the form of a Y-junction, such that right inlet 1716 and left inlet 1718 are located at the right and left apex of the letter "Y", respectively, and outlet 1720 is located on the leg of the letter "Y". Split fibers 1722 are arranged within sleeve 1714, such that right arm 1732 of each split fiber 1722 is located in right section 1724 of sleeve 1714 and left arm 1734 of the respective split fiber 1722 is located in left section 1726 of sleeve 1714. Common arm 1736 of all split fibers 1722 are located in common section 1728 of sleeve 1714.

Right inlet 1716 can receive a right side view image of three-dimensional object 1730 and left inlet 1718 can receive a left side view image thereof. The controller controls the operation of image differentiator 1702 and the two illuminators, such that right inlet 1716 and left inlet 1718 alternately receive the right side view image and the left side view image, respectively, of three-dimensional object 1730.

Each of a plurality of the right arms 1732 receives a substantially small portion of the right side view image of three-dimensional object 1730 and transfers this portion of the image to the respective common arm 1736. The plurality of the common arms 1736, together produce the complete right side view image of three-dimensional object 1730, as received by the plurality of the right arms 1732. In the same manner, a plurality of left arms 1734 transfers the left side view image of three-dimensional object 1730, to the plurality of common arms 1736. The common arms 1736 together produce the complete left side view image of three-dimensional object 1730, as received by the plurality of the left arms 1734.

The relative positions of common arms 1736 of split fibers 1722 within common section 1728, are substantially the same as the relative positions of right arms 1732 within right section 1724, and the relative positions of left arms 1734 within left section 1726. Otherwise, the image of three-dimensional object 1730 at outlet 1720 will be skewed and different from the image of three-dimensional object 1730 as viewed by either right inlet 1716 or left inlet 1718.

If the split fibers 1722 are placed within sleeve 1714, such that junctions 1742 (FIG. 37B) of all the split fibers 1722 are located side by side, a substantially large space will be consumed. To mitigate this problem, the split fibers 1722 are placed within sleeve 1714, such that junctions 1742 of each split fibers 1722 are periodically and sequentially located on the top of each other, at different heights.

In the example set forth in FIG. 37A, right side filter 1710 lets the light through. Therefore, right inlet 1716 receives light beams 1738 and 1740, which include information respective of the right side view image of three-dimensional object 1730, through right side filter 1710. Right lens 1748 focuses light beams 1738 and 1740 on right inlet 1716, wherein right lens 1748 images the points on three-dimensional object 1730 from which light beams 1738 and 1740 have arrived, on right inlet 1716. The plurality of right arms 1732 transfer light beams 1738 and 1740 to outlet 1720, via the respective plurality of common arms 1736. Optical assembly 1706 receives light beams 1738 and 1740 from outlet 1720 and optical assembly 1706 focuses light beams 1738 and 1740 on light sensor array 1708. A processor, such as processor 208 (FIG. 2), enables light sensor array 1708 to detect a right side view image of three-dimensional object 1730, according to the state of image differentiator 1702 (i.e., when right side filter 1710 is open).

Light beams 1744 and 1746, which include information respective of the left side view image of three-dimensional object 1730, reach left side filter 1712. Since left side filter 1712 is not operative, light beams 1744 and 1746 are blocked and do not reach light sensor array 1708.

In another mode of apparatus 1700 (not shown), right side filter 1710 blocks light beams 1738 and 1740, while left side filter 1712 lets through the light beams 1744 and 1746. Left lens 1750 focuses light beams 1744 and 1746 on left inlet 1718, wherein left lens 1750 images the points on three-dimensional object 1730 from which light beams 1744 and 1746 have arrived, on left inlet 1718. In this case, the plurality of left arms 1734 transfer light beams 1744 and 1746 to outlet 1720, via the respective plurality of common arms 1736. Optical assembly 1706 receives light beams 1744 and 1746 from outlet 1720 and optical assembly 1706 focuses light beams 1744 and 1746 on light sensor array 1708. The processor enables light sensor array 1708 to detect a left side view image of three-dimensional object 1730, according to the state of image differentiator 1702 (i.e., when left side filter 1712 is open).

Figure 38A:
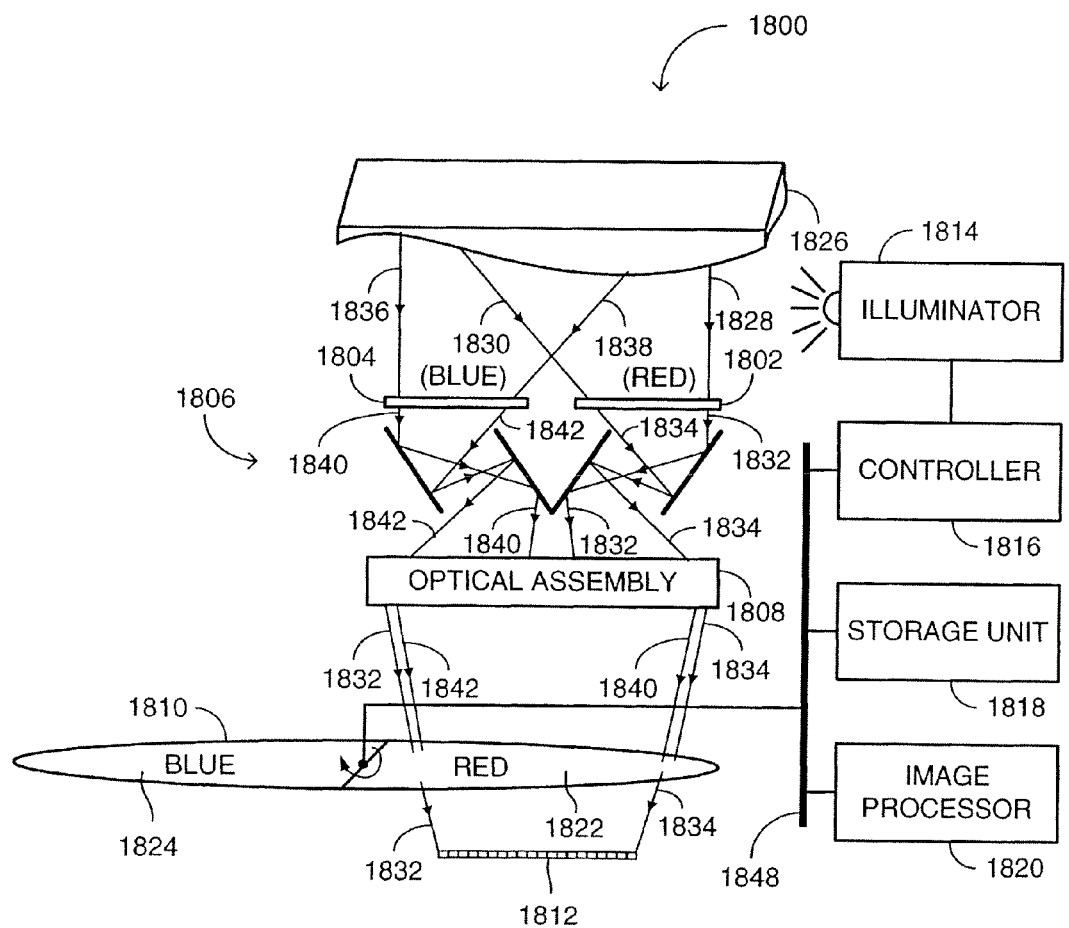
FIG. 38A is a schematic illustration of a stereoscopic imaging apparatus, constructed and operative in accordance with another embodiment of the disclosed technique.
Figure 38B:
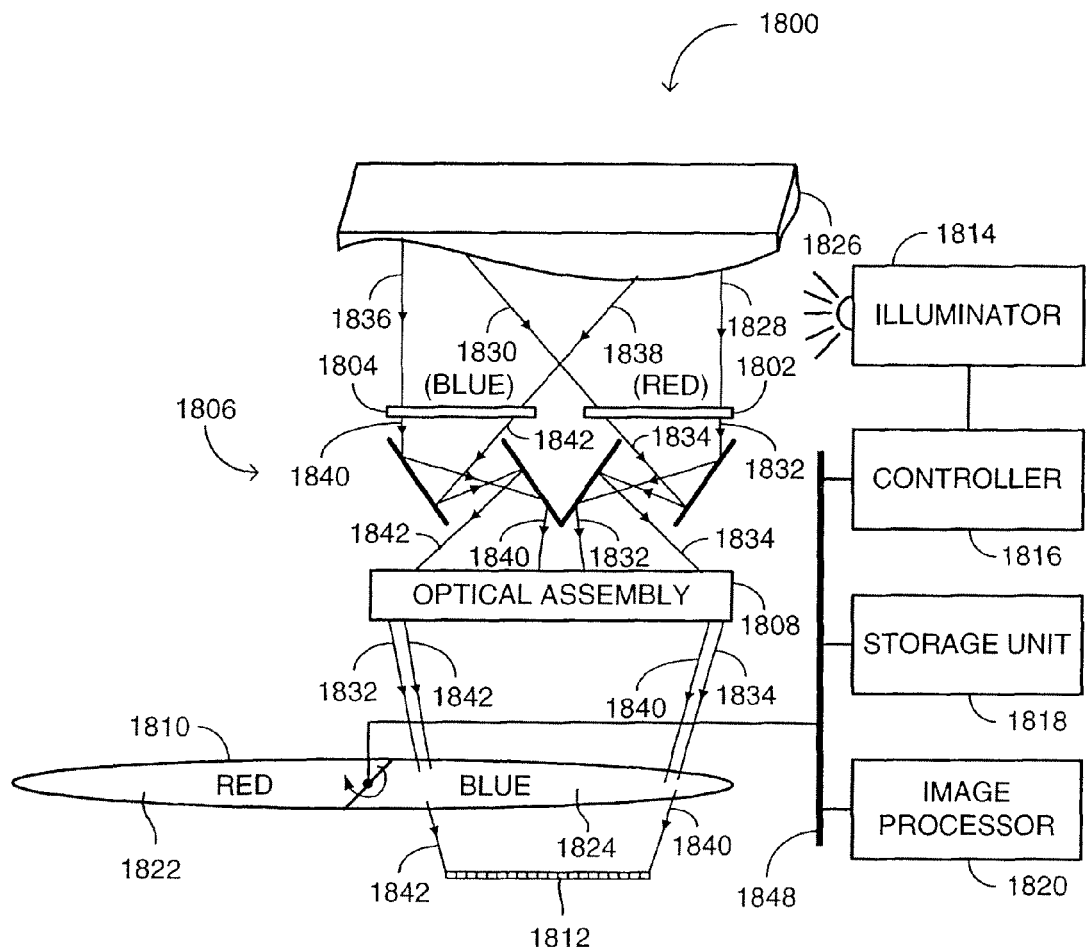
FIG. 38B is a schematic illustration of the apparatus of FIG. 38A, in another mode of operation.

Reference is now made to FIGS. 38A and 38B. FIG. 38A is a schematic illustration of a stereoscopic imaging apparatus, generally referenced 1800, constructed and operative in accordance with another embodiment of the disclosed technique. FIG. 38B is a schematic illustration of the apparatus of FIG. 38A, in another mode of operation.

Apparatus 1800 includes a right side filter 1802, a left side filter 1804, a periscope assembly 1806, an optical assembly 1808, a duo-tone rotating disk 1810, a light sensor array 1812, an illuminator 1814, a controller 1816, a storage unit 1818 and an image processor 1820. Right side filter 1802 is a light filter, which admits light in only a predetermined range of wavelengths. Left side filter 1804 is a light filter which admits light in another predetermined range of wavelengths, different than the range of wavelengths which is set for right side filter 1802. Periscope assembly 1806 is similar to periscope assembly 1206, as described herein above in connection with FIG. 30A. Duo-tone rotating disk 1810 includes two filtering portions 1822 and 1824. Filtering portion 1822 admits light in a range of wavelengths which matches the range of wavelengths of right side filter 1802 and filtering portion 1824 admits light in another range of wavelengths which matches the range of wavelengths of left side filter 1804.

Illuminator 1814 provides light in at least the range of wavelengths defined by filtering portions 1822 and 1824. In the example set forth in FIGS. 38A and 38B, right side filter 1802 admits only red light, whereas left side filter 1804 admits only blue light. Hence, filtering portion 1822 is red (i.e., admits only red light radiation), and filtering portion 1824 is blue (i.e., admits only blue light radiation). Light sensor array 1812 detects light in at least the range of wavelengths defined by filtering portions 1822 and 1824.

Right side filter 1802 and left side filter 1804 are located between a three-dimensional object 1826 and periscope assembly 1806. Periscope assembly 1806 is located between right side filter 1802 and left side filter 1804, and optical assembly 1808. Optical assembly 1808 is located between periscope assembly 1806 and duo-tone rotating disk 1810. Duo-tone rotating disk 1810 is located between optical assembly 1808 and light sensor array 1812. Duo-tone rotating disk 1810, light sensor array 1812, controller 1816, storage unit 1818 and image processor 1820 are interconnected via a bus 1848.

With reference to FIG. 38A, right side filter 1802 receives light beams 1828 and 1830, which include information respective of the right side view image of three-dimensional object 1826. Right side filter 1802 directs light beams 1828 and 1830 to periscope assembly 1806, as light beams 1832 and 1834, respectively, which have a red tone. Left side filter 1804 receives light beams 1836 and 1838, which include information respective of the left side view image of three-dimensional object 1826. Left side filter 1804 directs light beams 1836 and 1838 to periscope assembly 1806, as light beams 1840 and 1842, respectively, which have a blue tone. Periscope assembly 1806 directs light beams 1832, 1834, 1840 and 1842 to optical assembly 1808.

Optical assembly 1808 receives light beams 1832, 1834, 1840 and 1842 at inlets thereof (not shown), and directs light beams 1832, 1834, 1840 and 1842 from an outlet thereof (not shown) to duo-tone rotating disk 1810. In the example set forth in FIG. 38A, duo-tone rotating disk 1810 is shown in an instant during the rotation thereof, such that filtering portion 1822 (red) is located above light sensor array 1812. Filtering portion 1822 admits only red beams of light. Thus, filtering portion 1822 admits light beams 1832 and 1834, which include information respective of the right side view image of three-dimensional object 1826. It is noted that filtering portion 1822 blocks light beams 1840 and 1842 which include information respective of the left side view image of three-dimensional object 1826.

Controller 1816 enables light sensor array 1812 to detect a right side view image of three-dimensional object 1826, according to the position of duo-tone rotating disk 1810 relative to light sensor array 1812 (i.e., when filtering portion 1822 is located above light sensor array 1812). Controller 1816 stores this right side view image in storage unit 1818.

With reference to FIG. 38B, duo-tone rotating disk 1810 is in an instant during the rotation thereof, such that filtering portion 1824 (blue) is located above light sensor array 1812. Filtering portion 1824 admits only blue beams of light. Thus, filtering portion 1824 admits light beams 1840 and 1842, which include information respective of the left side view image of three-dimensional object 1826. It is noted that filtering portion 1824 blocks light beams 1832 and 1834 which include information respective of the right side view image of three-dimensional object 1826. Controller 1816 enables light sensor array 1812 to detect a left side view image of three-dimensional object 1826, according to the position of duo-tone rotating disk 1810 relative to light sensor array 1812 (i.e., when filtering portion 1824 is located above light sensor array 1812). Controller 1816 stores this left side view image in storage unit 1818. Image processor 1820 produces a video signal for a stereoscopic display, such as stereoscopic display 214 (FIG. 2), by retrieving these images from storage unit 1818 and processing them.

Reference is now made to FIGS. 39A and 39B. FIG. 39A is a schematic illustration of a partially-transparent rotating disk, generally referenced 1900, constructed and operative in accordance with a further embodiment of the disclosed technique. FIG. 39B is a schematic illustration of a partially-transparent rotating disk, generally referenced 1910, constructed and operative in accordance with another embodiment of the disclosed technique.

With reference to FIG. 39A, partially-transparent rotating disk 1900 is made of plastic, glass, and the like. Partially-transparent rotating disk 1900 is divided into a transparent portion 1902 and an opaque portion 1904. Transparent portion 1902 and opaque portion 1904 are divided by a diameter 1906 of partially-transparent rotating disk 1900. Transparent portion 1902 admits light of a selected range of wavelength (either in the visible range or the invisible range), while opaque portion 1904 blocks light at this selected range of wavelength.

With reference to FIG. 39B, partially-transparent rotating disk 1910 includes a transparent portion 1912 and an opaque portion 1914. Transparent portion 1912 occupies one quadrant of partially-transparent rotating disk 1910, while opaque portion 1914 occupies the rest. The properties of transparent portion 1912 and opaque portion 1914 are similar to properties of transparent portion 1902 and opaque portion 1904, respectively.

Reference is now made to FIGS. 40A and 40B. FIG. 40A is a schematic illustration of a multi-wavelength rotating disk, generally referenced 1930, constructed and operative in accordance with a further embodiment of the disclosed technique. FIG. 40B is a schematic illustration of a multi-wavelength rotating disk, generally referenced 1950, constructed and operative in accordance with another embodiment of the disclosed technique.

With reference to FIG. 40A, multi-wavelength rotating disk 1930 is divided to a transparent portion 1932 and an opaque portion 1934. Transparent portion 1932 and opaque portion 1934 are divided by a diameter 1936 of multi-wavelength rotating disk 1930. Transparent portion 1932 is divided to a plurality of filtering sectors 1938, 1940 and 1942. Filtering sectors 1938, 1940 and 1942 occupy substantially equal areas. Each of the filtering sectors 1938, 1940 and 1942 admits light at a different range of wavelengths (either in the visible range or the invisible range), while opaque portion 1934 blocks light at all of these different range of wavelengths. In the example set forth in FIG. 40A, filtering sectors 1938, 1940 and 1942 admit red, green and blue light, respectively.

With reference to FIG. 40B, multi-wavelength rotating disk 1950 includes a plurality of filtering sectors 1952, 1954 and 1956 and a plurality of opaque sectors 1958, 1960 and 1962. Filtering sectors 1952, 1954 and 1956, and opaque sectors 1958, 1960 and 1962, occupy substantially equal areas. Each of the filtering sectors 1952, 1954 and 1956 admits light at a different range of wavelengths (either in the visible range or the invisible range), while opaque sectors 1958, 1960 and 1962 block light at all of these different range of wavelengths. In the example set forth in FIG. 40B, filtering sectors 1952, 1954 and 1956 admit red, green and blue light, respectively.

According to another aspect of the disclosed technique, the two-dimensional light sensor array is replaced by a one-dimensional light sensor array and a rotating mirror, which swivels about an axis perpendicular to the stereoscopic axis. The rotating mirror rotates about an axis which is parallel to the one-dimensional light sensor array, thereby continuously scanning the surface of a three-dimensional body. The rotating mirror directs the scanned image to the one-dimensional light sensor array, via an image differentiator, a light directing assembly and an optical assembly. A controller coupled with the one-dimensional light sensor array enables the one-dimensional light sensor array to detect images of different regions of the three-dimensional object in sequence. The image differentiator differentiates between a line of the right side view image and a line of the left side view image of each of these different regions, before these lines of image reach the one-dimensional light sensor array.

Figure 41A:
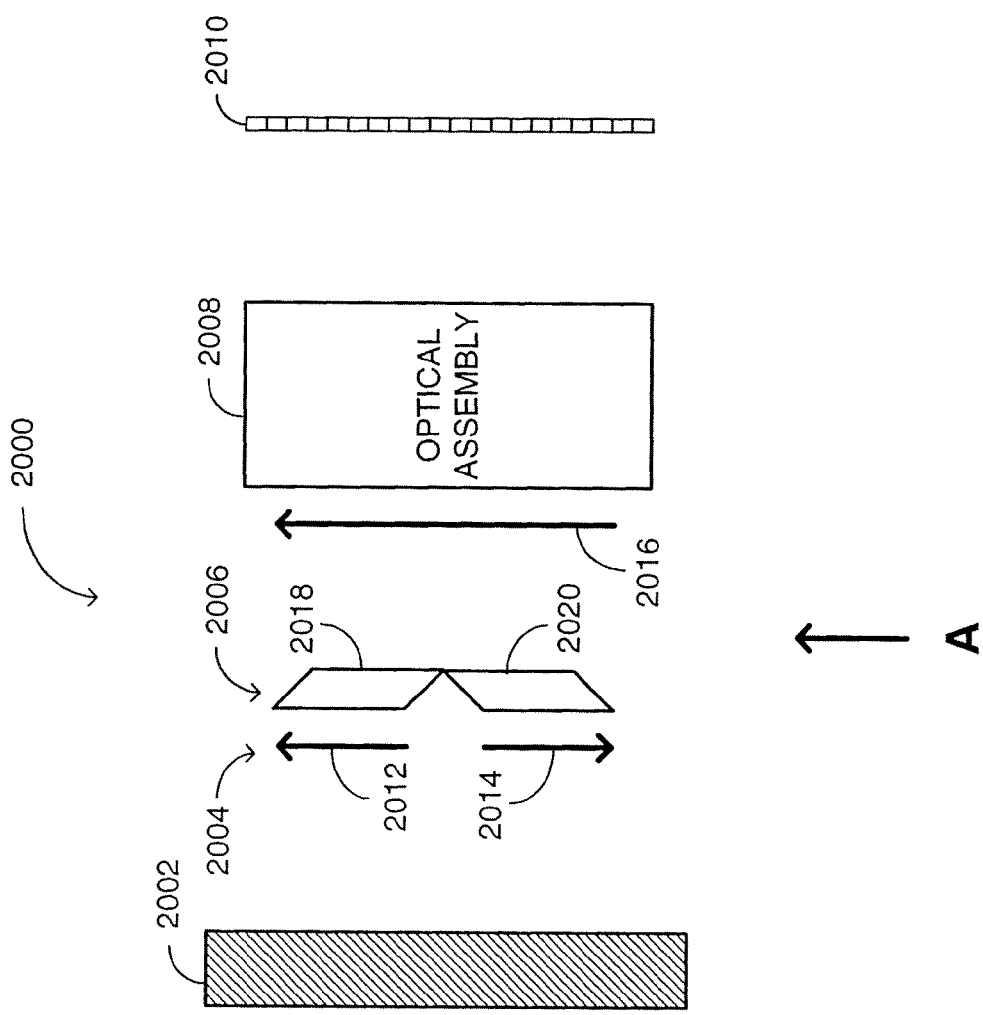
FIG. 41A is a schematic illustration of a top view of a stereoscopic image scanning apparatus, constructed and operative in accordance with a further embodiment of the disclosed technique.
Figure 41B:
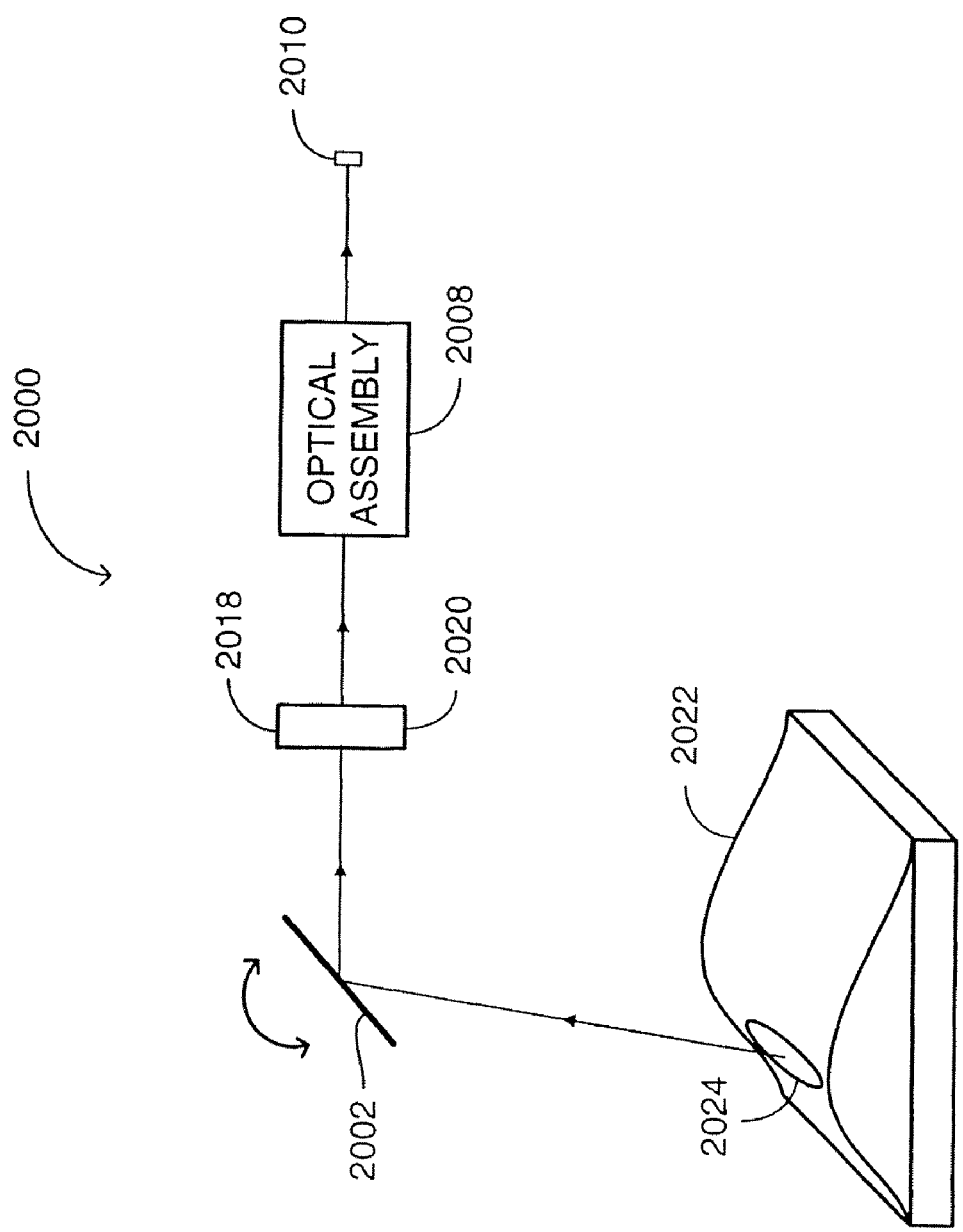
FIG. 41B is a schematic illustration of side view (referenced A in FIG. 41A) of the apparatus of FIG. 41A, in one mode of scanning.
Figure 41C:
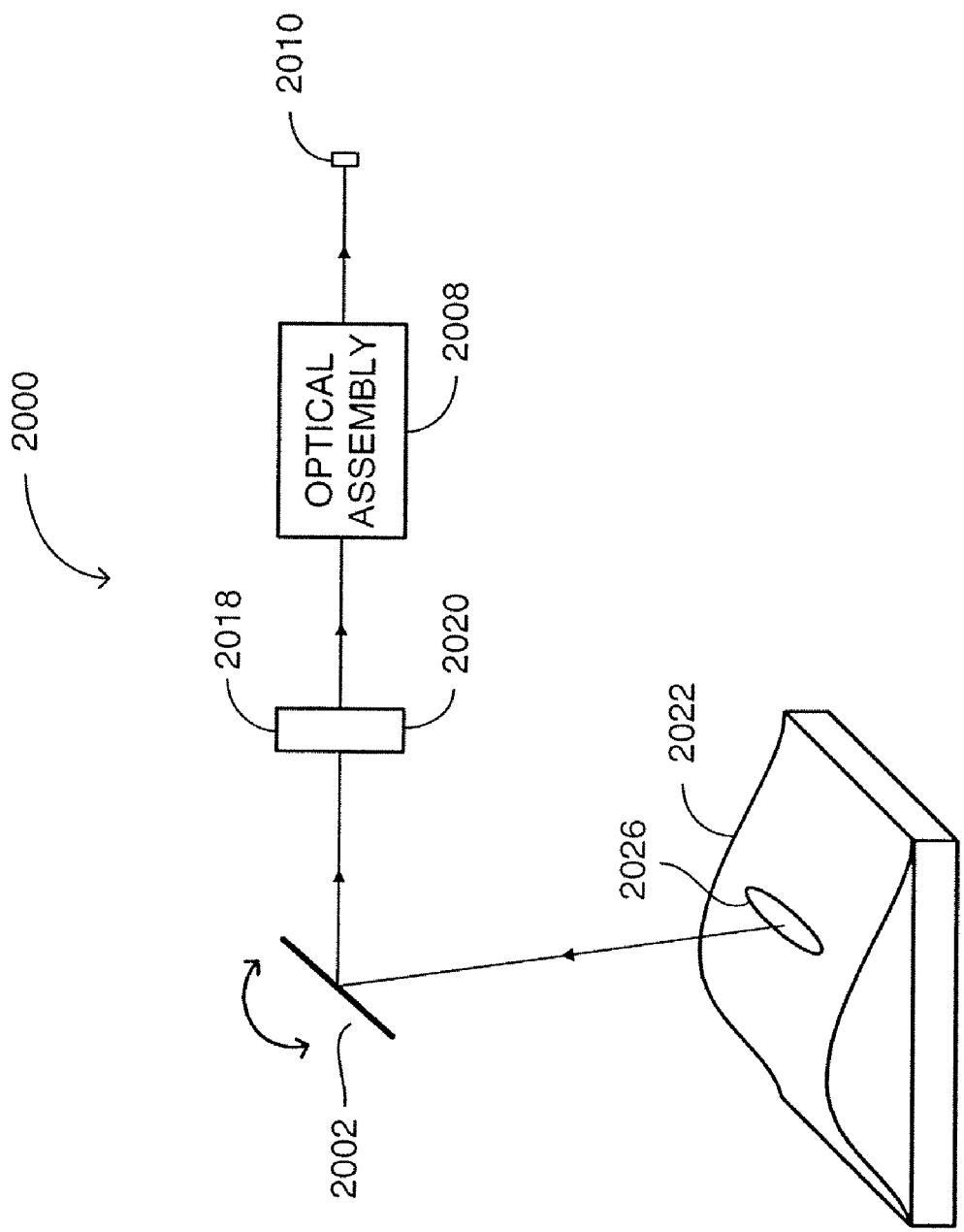
FIG. 41C is a schematic illustration of the apparatus of FIG. 41B, in another mode of scanning.

Reference is now made to FIGS. 41A, 41B and 41C. FIG. 41A is a schematic illustration of a top view of a stereoscopic image scanning apparatus, generally referenced 2000, constructed and operative in accordance with a further embodiment of the disclosed technique. FIG. 41B is a schematic illustration of side view (referenced A in FIG. 41A) of the apparatus of FIG. 41A, in one mode of scanning. FIG. 41C is a schematic illustration of the apparatus of FIG. 41B, in another mode of scanning.

With reference to FIG. 41A, apparatus 2000 includes a scanning element 2002, an image differentiator 2004, an image directing assembly 2006, an optical assembly 2008 and an image detector 2010. Image differentiator 2004 includes static polarizers 2012 and 2014, and a dynamic polarizer 2016. Image directing assembly 2006 includes a right periscopic prism 2018 and a left periscopic prism 2020. Image detector 2010 includes a one-dimensional light sensor array, which is essentially a plurality of light sensors, arranged in a row. Scanning element 2002 can be in form of a flat mirror, prism, lens, spherical mirror, aspherical mirror, holographic element, and the like. In the examples described according to FIGS. 41B and 41C, scanning element 2002 is in form of a mirror.

Static polarizers 2012 and 2014 are located between scanning element 2002 and image directing assembly 2006. Image directing assembly 2006 is located between static polarizers 2012 and 2014 on one side and dynamic polarizer 2016 on the other side. Dynamic polarizer 2016 is located between image directing assembly 2006 and optical assembly 2008. Optical assembly 2008 is located between dynamic polarizer 2016 and image detector 2010.

With further reference to FIG. 41B, a three-dimensional object 2022 is located at a side of apparatus 2000. In this configuration the longitudinal axis of apparatus 2000 is approximately perpendicular to the viewing direction of three-dimensional object 2022, by apparatus 2000.

Scanning element 2002 being at a certain angular position, directs an image line of a region 2024 of three-dimensional object 2022, to static polarizers 2012 and 2014. Right periscopic prism 2018 receives a line of the right side view image of region 2024 via static polarizer 2012 and left periscopic prism 2020 receives a line of the left side view image of region 2024 via static polarizer 2014. Right periscopic prism 2018 and left periscopic prism 2020 direct the line of the right side view image and the line of the left side view image of region 2024 to dynamic polarizer 2016. In the example set forth in FIG. 41A, the polarization angle of dynamic polarizer 2016 is substantially the same as the polarization angle of static polarizer 2012. Hence, the light beams which define the line of the right side view image, pass through dynamic prism 2016 and enter optical assembly 2008. Optical assembly 2008 directs the line of the right side view image on one-dimensional light sensor array 2010. Since the polarization angle of dynamic polarizer 2016 is approximately 90 degrees away from the polarization angle of static polarizer 2014, dynamic polarizer 2016 blocks the light beams which define the line of the left side view image and the line of left side view image does not reach one-dimensional light sensor array 2010.

With further reference to FIG. 41C, scanning element 2002 is at another angular position relative to the one illustrated in FIG. 41B. Hence, scanning element 2002 directs a line of an image of a region 2026 of three-dimensional object 2022, to static polarizers 2012 and 2014. Right periscopic prism 2018 and left periscopic prism 2020 receive a line of a right side view image and a line of a left side view image of the image of region 2026, via static polarizers 2012 and 2014, respectively. Right periscopic prism 2018 and left periscopic prism 2020 direct the line of the right side view image and the line of the left side view image, respectively, to dynamic polarizer 2016. In the example set forth in FIG. 41A, the polarization angle of dynamic polarizer 2016 is substantially the same as the polarization angle of static polarizer 2012 and the polarization angle of dynamic polarizer 2016 is approximately 90 degrees away from that of static polarizer 2014.

Hence, the light beams which define the line of the right side view image of region 2026 pass through dynamic polarizer 2016 and reach one-dimensional light sensor array 2010, while the light beams which define the line of the left side view image of region 2026 are blocked by dynamic polarizer 2016 and do not reach one-dimensional light sensor array 2010. A controller which is coupled with scanning element 2002 and to one-dimensional light sensor array 2010, enables one-dimensional light sensor array 2010 to detect a line of an image of three-dimensional object 2022, according to the angular position of scanning element 2002. It is noted that scanning element 2002 can either rotate continuously, or rotate back and forth between two angular positions.

Alternatively, the image detector is a two-dimensional light sensor array operating in time delay integration (TDI) mode. The scanning element scans a plurality of successive two-dimensional regions of the three-dimensional object. The scanning element directs the two-dimensional images of these two-dimensional regions, in succession, to the image detector. A controller is coupled with the scanning element and to the image detector. The controller successively shifts the electronic charges from one row of the image detector to the other row in turn, along the columns of the image detector in synchrony with the scanning movement of the scanning element. After shifting the electronic charges from a first row to a second row, the controller resets the first row. In this manner, the sum of the electronic charges of all the rows are accumulated in the last row of the two-dimensional light sensor array. The controller delivers the charges from the last row of the image detector, in sequence and in synchrony with the scanning movement of the scanning element, to an image processor. The image processor produces a substantially sharp stereoscopic image of the region of the three-dimensional object, which the scanning element repeatedly scans.

It is noted, that if the image detector does not operate in TDI mode (i.e., the controller does not shift the charges from one column to the other), then the image processor produces a blurred stereoscopic image of the three-dimensional object. This is so, because the scanning element provides images of successive regions of the three-dimensional object to the image detector. The image processor produces a stereoscopic image of the three-dimensional object and the stereoscopic image is blurred according to the scanning speed of the scanning element.

According to another aspect of the disclosed technique, a right side filter and a left side filter are employed, each admitting an image at two different ranges of wavelengths. When the three-dimensional body is sequentially illuminated with light at each of the first ranges of wavelengths, the right side filter sequentially directs a right side view image of the three-dimensional object to the image detector, at each one of the first ranges of wavelengths. Likewise, when the three-dimensional body is sequentially illuminated at each of the second ranges of wavelengths, the left side filter sequentially directs a left side view image of the three-dimensional object to the image detector, at each one of the second ranges of wavelengths.

Figure 42A:
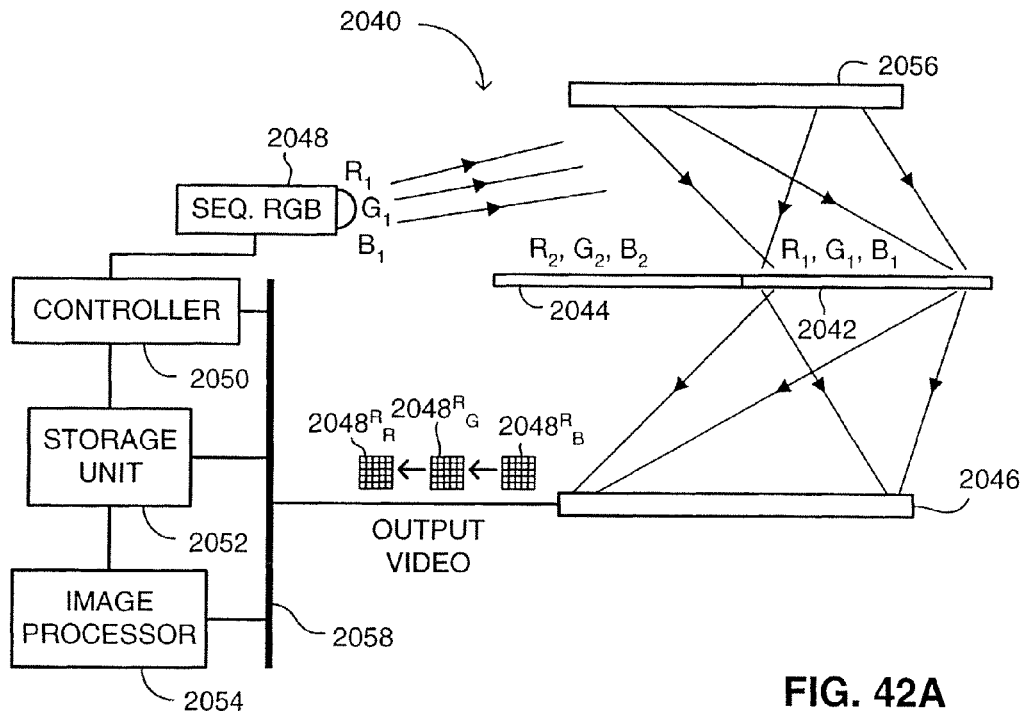
FIG. 42A is a schematic illustration of a stereoscopic imaging apparatus, constructed and operative in accordance with another embodiment of the disclosed technique.
Figure 42B:
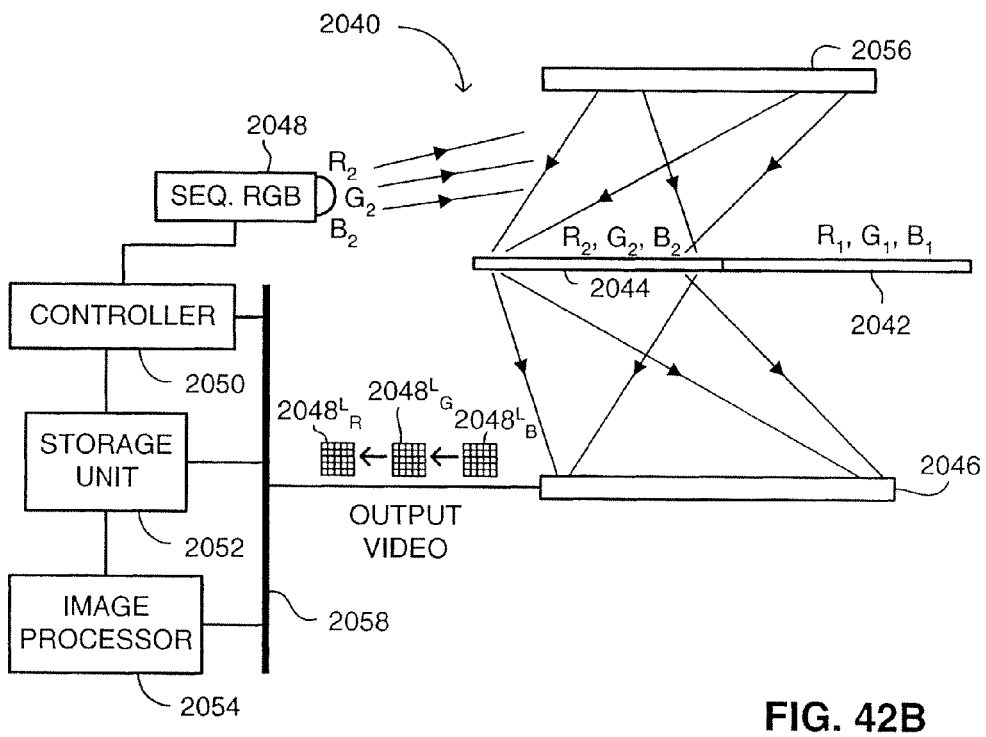
FIG. 42B is a schematic illustration of the stereoscopic imaging apparatus of FIG. 42A, in another mode of operation.

Reference is now made to FIGS. 42A and 42B. FIG. 42A is a schematic illustration of a stereoscopic imaging apparatus, generally referenced 2040, constructed and operative in accordance with another embodiment of the disclosed technique. FIG. 42B is a schematic illustration of the stereoscopic imaging apparatus of FIG. 42A, in another mode of operation.

Apparatus 2040 includes a right side filter 2042, a left side filter 2044, an image detector 2046, an illuminator 2048, a controller 2050, a storage unit 2052 and an image processor 2054. Right side filter 2042 and left side filter 2044 are located between a three-dimensional object 2056 and image detector 2046. Controller 2050 is coupled with illuminator 2048. Image detector 2046 controller 2050, storage unit 2052 and image processor 2054 are coupled together via a bus 2058.

Right side filter 2042 admits light within the ranges of wavelengths $\Delta R_1$, $\Delta G_1$ and $\Delta B_1$. Left side filter 2044 admits light within the ranges of wavelengths $\Delta R_2$, $\Delta G_2$ and $\Delta B_2$. Illuminator 2048 sequentially emits light at each of the ranges of wavelengths $\Delta R_1$, $\Delta G_1$, $\Delta B_1$, $\Delta R_2$, $\Delta G_2$ and $\Delta B_2$.

With reference to FIG. 42A, illuminator 2048 sequentially emits light at each of the ranges of wavelengths $\Delta R_1$, $\Delta G_1$ and $\Delta B_1$. Right side filter 2042 sequentially directs right side view images $2048^R_R$, $2048^R_G$ and $2048^R_B$ in red, green and blue, respectively, to image detector 2046 and controller 2050 enables image detector 2046 to detect these images in sequence. Controller 2050 stores these images in storage unit 2052. Image processor 2054 produces a video signal respective of a full color right side view image of three-dimensional object 2056, by retrieving right side view images $2048^R_R$, $2048^R_G$ and $2048^R_B$ from storage unit 2052 and processing these images. Since left side filter 2044 admits light only within the ranges of wavelengths $\Delta R_2$, $\Delta G_2$ and $\Delta B_2$, left side filter 2044 does not direct the left side view image of three-dimensional object 2056 to image detector 2046.

With reference to FIG. 42B, illuminator 2048 sequentially provides light at each of the ranges of wavelengths $\Delta R_2$, $\Delta G_2$ and $\Delta B_2$. In this case, left side filter 2044 sequentially directs left side view images $2048^L_R$, $2048^L_G$ and $2048^L_B$ in red, green and blue, respectively, to image detector 2046 and controller 2050 enables image detector 2046 to detect these images in sequence. Controller 2050 stores these images in storage unit 2052. Image processor 2054 produces a video signal respective of a full color left side view image of three-dimensional object 2056, by retrieving left side view images $2048^L_R$, $2048^L_G$ and $2048^L_B$ from storage unit 2052 and processing these images. Since right side filter 2042 admits light only within the ranges of wavelengths $\Delta R_1$, $\Delta G_1$ and $\Delta B_1$, right side filter 2042 does not direct the right side view image of three-dimensional object 2056 to image detector 2046.

Alternatively, illuminator 2048 is replaced by a sequential multi-wavelength illuminator which emits light at a mixture of the ranges of wavelengths $\Delta R_1$, $\Delta G_1$ and $\Delta B_1$ and at a mixture of the ranges of wavelengths $\Delta R_2$, $\Delta G_2$ and $\Delta B_2$. The sequential multi-wavelength illuminator sequentially emits light at each of the mixtures of the ranges of wavelengths $\Delta R_1$, $\Delta G_1$ and $\Delta B_1$, and at each of the mixtures of the ranges of wavelengths $\Delta R_2$, $\Delta G_2$ and $\Delta B_2$. When the sequential multi-wavelength illuminator emits light at the mixture of the ranges of wavelengths $\Delta R_1$, $\Delta G_1$ and $\Delta B_1$, right side filter 2042 directs a full color right side view image of three-dimensional object 2056, at the mixture of the ranges of wavelengths $\Delta R_1$, $\Delta G_1$ and $\Delta B_1$, to image detector 2046. When the sequential multi-wavelength illuminator emits light at the mixture of the ranges of wavelengths $\Delta R_2$, $\Delta G_2$ and $\Delta B_2$, left side filter 2044 directs a full color left side view image of three-dimensional object 2056, at the mixture of the ranges of wavelengths $\Delta R_2$, $\Delta G_2$ and $\Delta B_2$, to image detector 2046.

Further alternatively, illuminator 2048 is replaced by a multi-wavelength illuminator which emits light at a range of wavelengths which encompasses the ranges of wavelengths $\Delta R_1$, $\Delta G_1$, $\Delta B_1$, $\Delta R_2$, $\Delta G_2$ and $\Delta B_2$ and a duo-tone rotating disk in located between the right side filter and the left side filter at one side and the image detector at the other. The duo-tone rotating disk is divided to two transparent portions. One transparent portion of the duo-tone rotating disk admits light at the ranges of wavelengths $\Delta R_1$, $\Delta G_1$ and $\Delta B_1$, and the other transparent portion thereof, admits light at the ranges of wavelengths $\Delta R_2$, $\Delta G_2$ and $\Delta B_2$. The multi-wavelength illuminator continuously illuminates the three-dimensional object. As the duo-tone rotating disk rotates, the right side filter and the left side filter sequentially direct a full color right side view image and a full color left side view image, respectively, of the three-dimensional object, to the image detector.

Alternatively, right side filter 2042 and left side filter 2044 are spaced apart. In this case right side filter 2042 receives a right side view image of three-dimensional object 2056, which is considerably more distinct than a left side view image thereof, thereby allowing image processor 2054 to produce a more realistic full color stereoscopic image of three-dimensional object 2056. It is noted that instead of the duo-tone rotating disk, other types of rotating disks can be employed, such as a multi-wavelength rotating disk (FIGS. 40A and 40B), defined according to $\Delta R_1$, $\Delta G_1$, $\Delta B_1$, $\Delta R_2$, $\Delta G_2$ and $\Delta B_2$.

Figure 43:
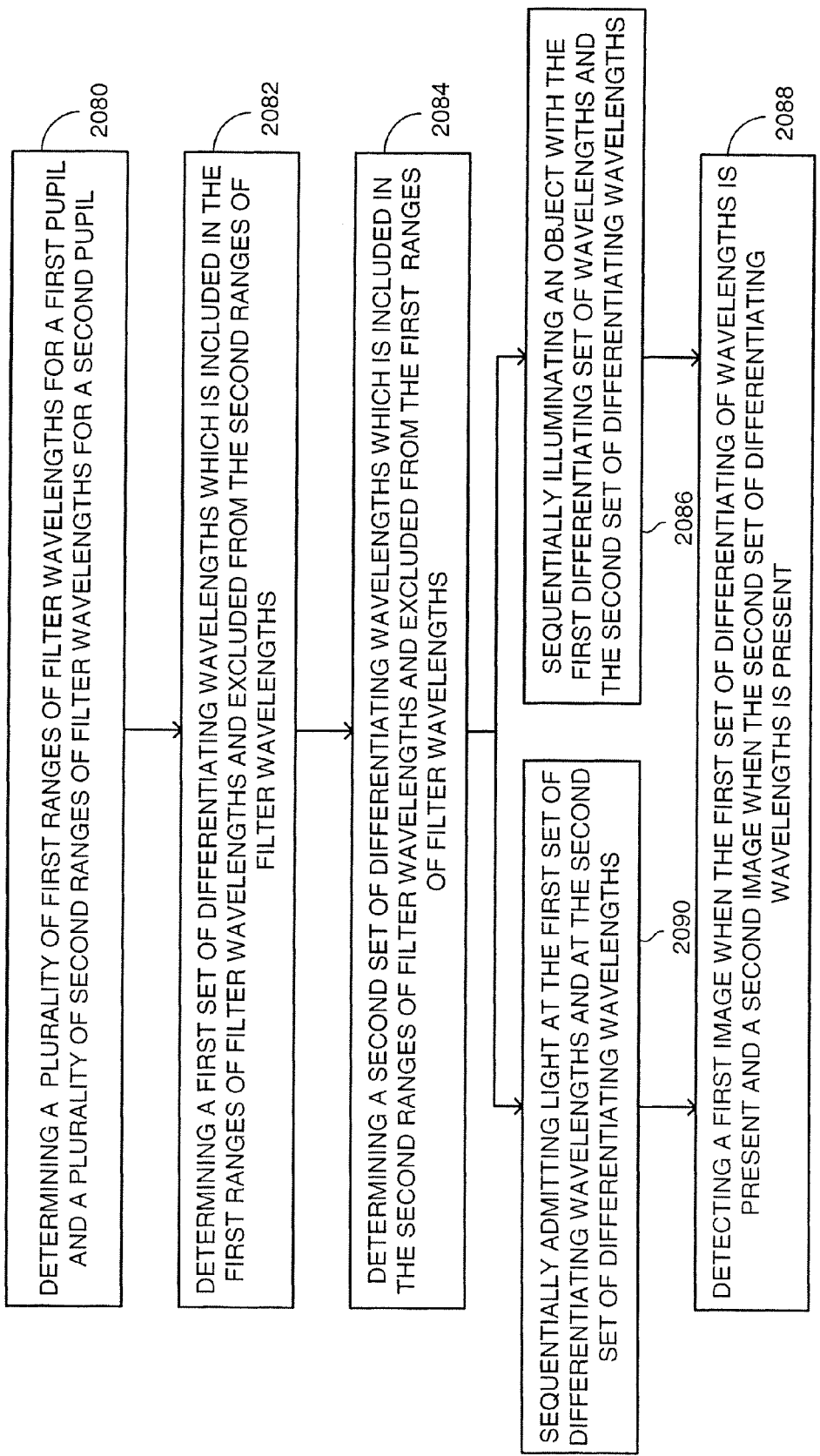
FIG. 43 is a schematic illustration of a method for operating a stereoscopic imaging apparatus, operative in accordance with a further embodiment of the disclosed technique.

Reference is now made to FIG. 43, which is a schematic illustration of a method for operating a stereoscopic imaging apparatus, operative in accordance with a further embodiment of the disclosed technique. In procedure 2080, a plurality of first ranges of filter wavelengths and a plurality of second ranges of filter wavelengths are determined for a first pupil and a second pupil, respectively. With reference to FIG. 30A, right side filter 1202 admits light at the ranges of wavelengths $\Delta R_1$, $\Delta G_1$, and $\Delta B_1$ and left side filter 1204 admits light at the ranges of wavelengths $\Delta R_1$, $\Delta G_1$, and $\Delta B_1$.

In procedure 2082, a first set of differentiating wavelengths which is included in the first ranges of filter wavelengths and excluded from the second ranges of filter wavelengths, is determined. With reference to FIG. 30A, illuminating unit 1240 is associated with the group of wavelengths $RGB_1$ which is included in the ranges of wavelengths $\Delta R_1$, $\Delta G_1$, and $\Delta B_1$ and excluded from the ranges of wavelengths $\Delta R_2$, $\Delta G_2$, and $\Delta B_2$. In procedure 2082, a second set of differentiating wavelengths, which is included in the second ranges of filter wavelengths and excluded from the first ranges of filter wavelengths, is determined. With reference to FIG. 30A, illuminating unit 1240 is associated with the group of wavelengths $RGB_2$ which is included in the ranges of wavelengths $\Delta R_2$, $\Delta G_2$, and $\Delta B_2$ and excluded from the ranges of wavelengths $\Delta R_1$, $\Delta G_1$, and $\Delta B_1$.

In procedure 2086, an object is sequentially illuminated with the first set of differentiating wavelengths and with the second set of differentiating wavelengths. With reference to FIGS. 30A and 30B, illuminating unit 1240 sequentially illuminates three-dimensional object 1230 at the group of wavelengths $RGB_1$ and at the group of wavelengths $RGB_1$.

In procedure 2088, a first image is detected when the first set of differentiating wavelengths is present and a second image is detected when the second set of differentiating wavelengths is present. With reference to FIG. 30A, controller 1216 enables light sensor array 1210 to detect the right side view image of three-dimensional object 1230, when illuminating unit 1240 emits light at the group of wavelengths $RGB_1$. With reference to FIG. 30B, controller 1216 enables light sensor array 1210 to detect the left side view image of three-dimensional object 1230, when illuminating unit 1240 emits light at the group of wavelengths $RGB_2$.

According to another embodiment, differentiation is performed by sequentially admitting light at the different sets of wavelengths, by a sequential filtering device, such as a rotating disk, an alternating filter, and the like. According to this embodiment, procedure 2090 replaces procedure 2086. In procedure 2090, light is admitted sequentially at the first set of differentiating wavelengths and at the second set of differentiating wavelengths.

The light differentiator can be any optical device which can differentiate between different wavelengths (e.g., by means of illumination, reflection or filtration). For example, the light differentiator can be a rotating disk divided into filtering sectors, wherein each filtering sector filters light at wavelengths which are included in one of the right side filter and the left side filter and excluded from the other of these two filters. Alternatively, a reflective rotating disk can be employed, which is divided into a plurality of reflecting sectors, where each reflecting sector reflects light at a different wavelength. Further alternatively, a multi-state flipping filter can be employed, which is mechanically flipped from one light filter to the other, in sequence. Other types of sequential filters, such as those which are operated electrically rather than mechanically, are applicable to this embodiment. Alternatively, the light differentiator can be a set of partially reflective mirrors that can be operated sequentially, each reflecting light at wavelengths which are included in one of the right side filter and the left side filter and excluded from the other of these two filters (e.g., a partially reflective mirror which reflects light at $CYMG_1$ and another partially reflective mirror which reflects light at $CYMG_2$).

Figure 44A:
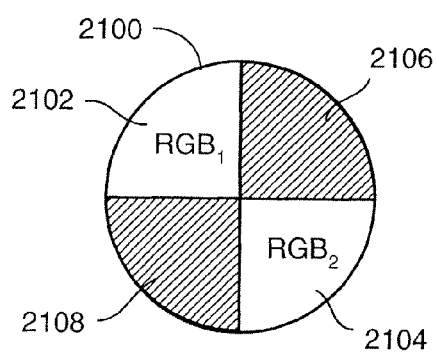
FIG. 44A is a schematic illustration of a rotating disk, constructed and operative in accordance with another embodiment of the disclosed technique.
Figure 44B:
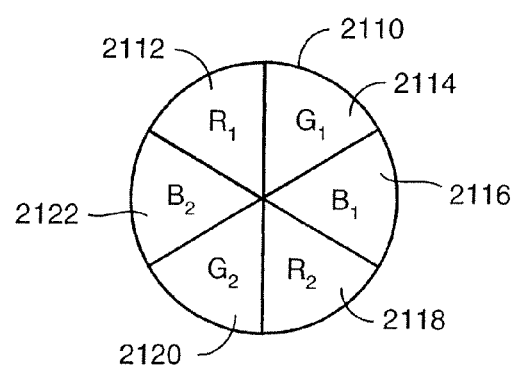
FIG. 44B is a schematic illustration of a rotating disk, constructed and operative in accordance with a further embodiment of the disclosed technique.

Reference is further made to FIGS. 44A and 44B. FIG. 44A is a schematic illustration of a rotating disk, generally referenced 2100, constructed and operative in accordance with another embodiment of the disclosed technique. FIG. 44B is a schematic illustration of a rotating disk, generally referenced 2110, constructed and operative in accordance with a further embodiment of the disclosed technique.

With reference to FIG. 44A, rotating disk 2100 includes two filtering sectors 2102 and 2104, and two opaque sectors 2106 and 2108. Filtering sector 2102 admits light at a group of wavelengths $R_1$, $G_1$ and $B_1$ (i.e., $RGB_1$), whereas filtering sector 2104 admits light at a group of wavelengths $R_2$, $G_2$ and $B_2$ (i.e., $RGB_2$). With reference to FIG. 44B, rotating disk 2110 includes filtering sectors 2112, 2114, 2116, 2118, 2120 and 2122, which admit light at wavelengths $R_1$, $G_1$, $B_1$, $R_2$, $G_2$ and $B_2$, respectively.

In examples described above, the light differentiator differentiates between two groups of wavelengths, where each group of wavelengths includes three wavelengths (i.e., R, G and B). Thus, the light differentiator of the stereoscopic imaging apparatus differentiates between two red wavelengths ($R_1$ and $R_2$), two green wavelengths ($G_1$ and $G_2$) and two blue wavelengths ($B_1$ and $B_2$). As noted above, the light differentiator can be for example, an illuminator, a light filtering element or a light reflecting element.

However, it is noted that each of the two groups of wavelengths can include more than three wavelengths and for that matter, any number of wavelengths. For example, high quality spectrometers are capable to split the light to 20 or 40 or more different wavelengths (e.g., $IR_1$, $IR_2$, $IR_3$, $IR_4$, ... $IR_n$, $R_1$, $R_2$, $R_3$, ..., $R_m$, $G_1$, $G_2$, $G_3$, ... $G_p$, $B_1$, $B_2$, $B_3$, ..., $B_q$, $UV_1$, $UV_2$, $UV_3$, ..., $UV_s$, and the like).

Figure 45A:
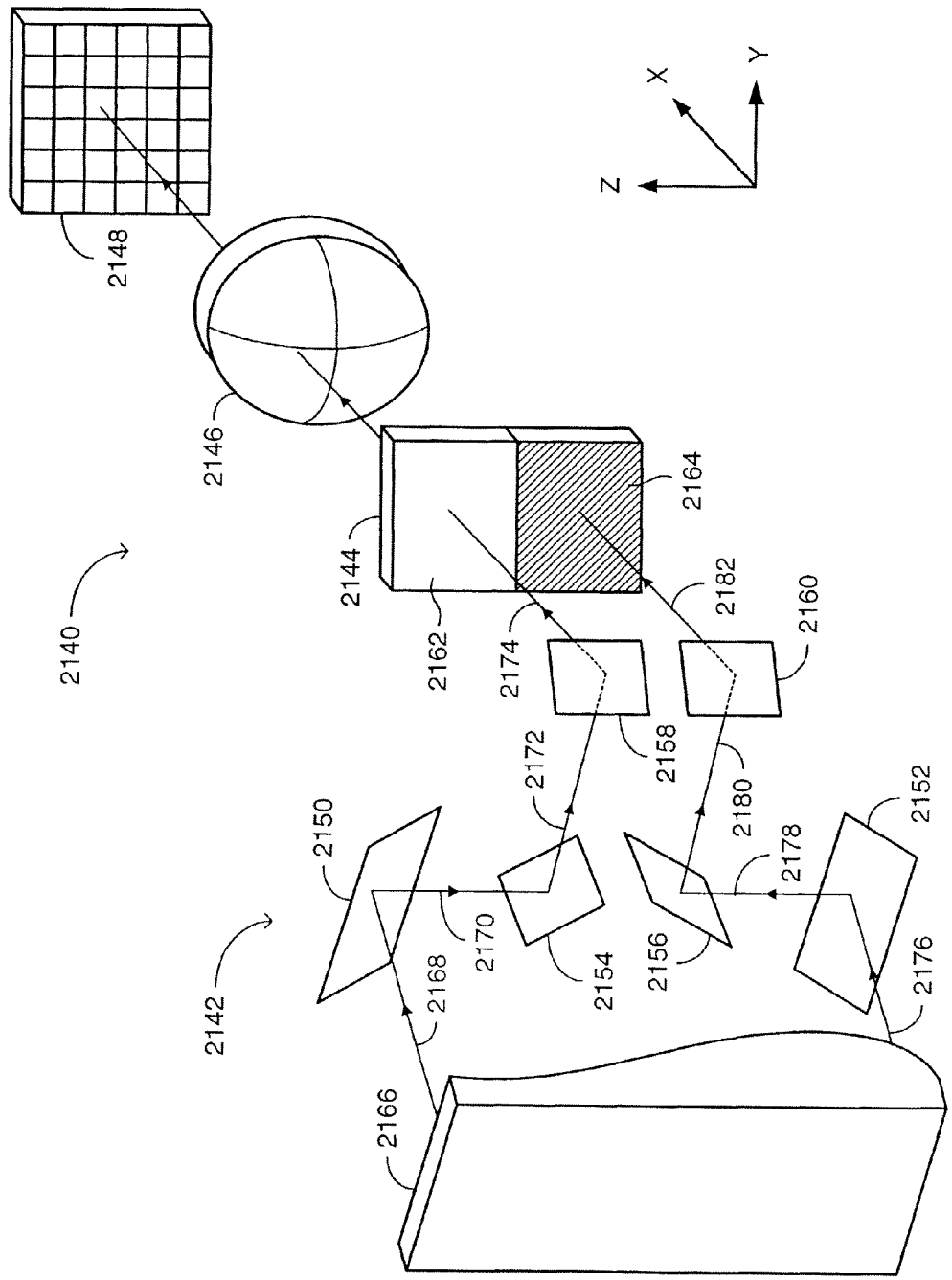
FIG. 45A is a schematic illustration of a stereoscopic imaging apparatus, constructed and operative in accordance with another embodiment of the disclosed technique.
Figure 45B:
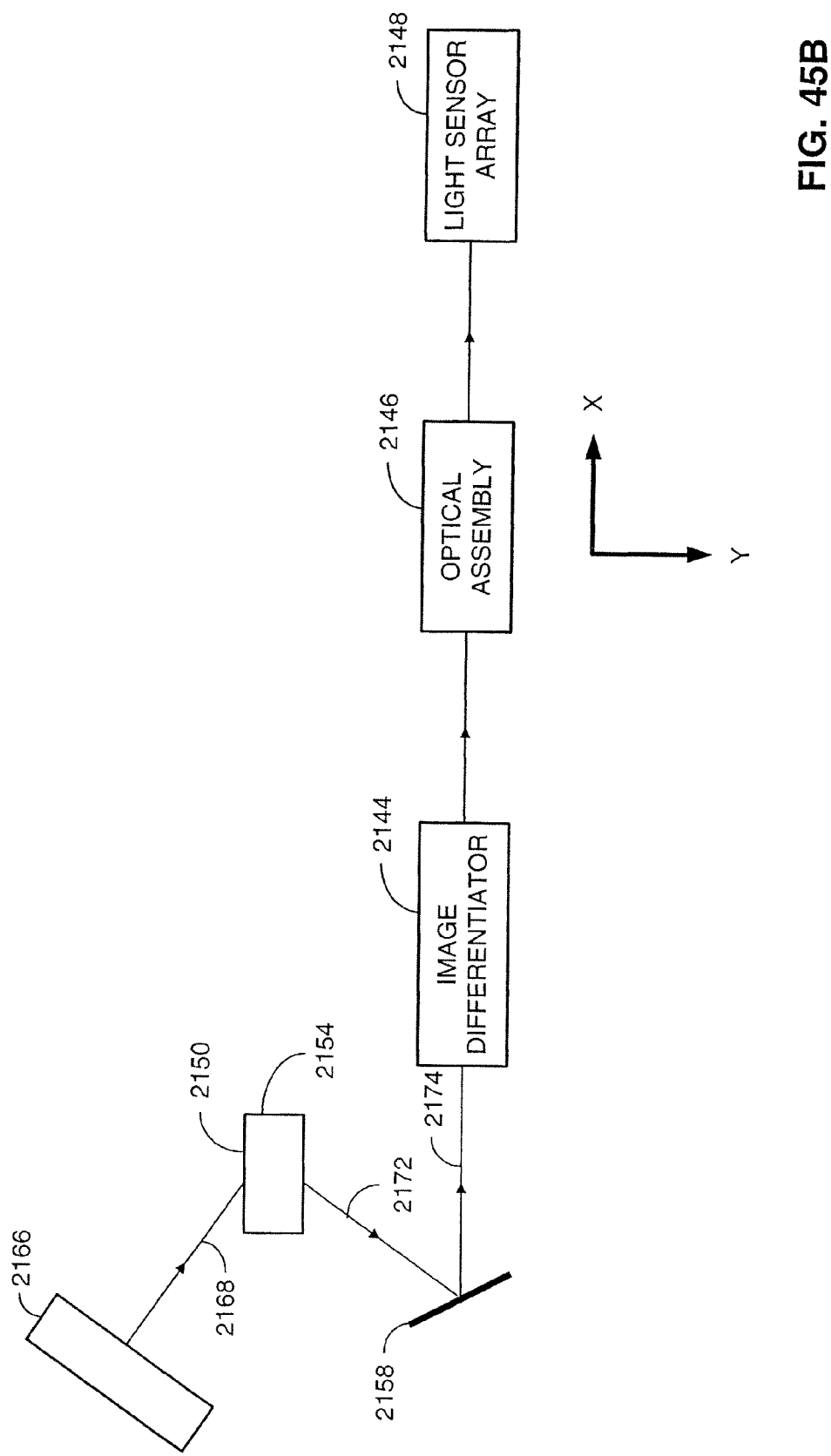
FIG. 45B is a schematic illustration of a top view of the apparatus of FIG. 45A.

Reference is now made to FIGS. 45A and 45B. FIG. 45A is a schematic illustration of a stereoscopic imaging apparatus, generally referenced 2140, constructed and operative in accordance with another embodiment of the disclosed technique. FIG. 45B is a schematic illustration of a top view of the apparatus of FIG. 45A.

With reference to FIG. 45A, apparatus 2140 includes a periscope assembly 2142, an image differentiator 2144, an optical assembly 2146 and a light sensor array 2148. Periscope assembly 2142 includes a right front mirror 2150, a left front mirror 2152, a right middle mirror 2154, a left middle mirror 2156, a right rear mirror 2158 and a left rear mirror 2160. In the example set forth in FIG. 45A, image differentiator 2144 is a multiple aperture similar to multiple aperture 1154 (FIG. 29A). Image differentiator 2144 includes a right aperture 2162 and a left aperture 2164.

Periscope assembly 2142 is located between a three-dimensional object 2166 and image differentiator 2144. Image differentiator 2144 is located between periscope assembly 2142 and optical assembly 2146. Optical assembly 2146 is located between image differentiator 2144 and light sensor array 2148.

The X axis designates the longitudinal axis of apparatus 2140. The X axis together with the Y and Z axes, form a rectilinear coordinate system. In the following description, the right hand rule applies to this coordinate system. For example, the phrase "a tilt of positive 45 degrees about the Z axis", means a tilt of 45 degrees about the Z axis in the direction of the fingers, when the thumb points in the direction of the Z axis. On the other hand, the phrase "a tilt of negative 45 degrees about the Z axis", means a tilt of 45 degrees about the Z axis in the direction of the fingers, when the thumb points in a direction opposite to the Z axis.

The reflecting surface of right front mirror 2150 is tilted by preferably positive 45 degrees about the Y axis from the Z-Y plane and by preferably negative 30 degrees about the Z axis, from the Z-X plane. The reflecting surface of left front mirror 2152 is tilted by preferably positive 45 degrees about the Y axis from the X-Y plane and by preferably negative 30 degrees about the Z axis, from the Z-X plane.

The reflecting surface of right middle mirror 2154 is tilted by preferably negative 45 degrees about the X axis from the Z-X plane and by preferably negative 30 degrees about the Z axis, from the Z-X plane. The reflecting surface of left middle mirror 2156 is tilted by preferably positive 45 degrees about the X axis from the Z-X plane and by preferably negative 30 degrees about the Z axis, from the Z-X plane.

The reflecting surfaces of right rear mirror 2158 and left rear mirror 2160 are tilted by preferably negative 60 degrees about the Z axis from the Z-X plane. Hence, periscope assembly 2142 is tilted preferably by negative 30 degrees about the Z axis from the Z-X plane.

Right front mirror 2150 receives a light beam 2168 respective of a right side view image of three-dimensional object 2166. Since periscope assembly 2142 is tilted by substantially negative 30 degrees about the Z axis, light beam 2168 is located on a plane which is tilted by substantially negative 30 degrees from the Z-X plane, about the Z axis. Right front mirror 2150 directs a reflection of light beam 2168 toward right middle mirror 2154, as a light beam 2170. Light beam 2170 is located on the Z-X plane.

Right middle mirror 2154 directs a reflection of light beam 2170 toward right rear mirror 2158, as a light beam 2172. Light beam 2172 is located at the intersection of the X-Y plane and a plane which is tilted about the Z axis by approximately positive 60 degrees from the Z-X plane. Right rear mirror 2158 directs a reflection of light beam 2172 toward image differentiator 2144, as a light beam 2174. Light beam 2174 points in a direction substantially parallel to the X axis. In the example set forth in FIG. 45A, right aperture 2162 is open while left aperture 2164 is closed. Thus, image differentiator 2144 admits light beam 2174 and optical assembly 2146 directs light beam 2174 toward light sensor array 2148.

With reference to FIG. 45B, right front mirror 2150 receives light beam 2168 at an angle of approximately 30 degrees relative to the X axis. Right middle mirror 2154 reflects light beam 2168 as light beam 2170 (not shown in FIG. 45B) in a direction pointing into the drawing and right middle mirror 2154 reflects light beam 2170 as light beam 2172. As shown in FIG. 45B, light beam 2172 points in a direction of approximately 90 degrees relative to that of light beam 2168. Right rear mirror 2158 is tilted approximately 60 degrees relative to the X axis, whereby right rear mirror 2158 reflects light beam 2172 as light beam 2174 in a direction substantially parallel to the X axis.

Referring back to FIG. 45A, left front mirror 2152 receives a light beam 2176 respective of a left side view image of three-dimensional object 2166 and directs a reflection of light beam 2176 toward left middle mirror 2156, as a light beam 2178. Light beam 2176 is located on the same plane as that of light beam 2168 and light beam 2178 is located on the same plane as that of light beam 2170. Left middle mirror 2156 directs a reflection of light beam 2178 toward left rear mirror 2160, as a light beam 2180. Light beam 2180 is located on the same plane as that of light beam 2172. Left rear mirror directs a reflection of light beam 2180 toward image differentiator 2144, as a light beam 2182. Light beam 2182 points in a direction substantially parallel to the X axis. Since left aperture 2164 is closed, image differentiator 2144 blocks light beam 2182.

It is noted that right front mirror 2150, right middle mirror 2154 and right rear mirror 2158 can be incorporated in a right prism, wherein the right prism is titled sideways relative to the longitudinal axis of the apparatus. In this case, each of the right front mirror 2150, right middle mirror 2154 and right rear mirror 2158 represents the respective reflective surface of the right prism. Likewise, right front mirror 2152, right middle mirror 2156 and right rear mirror 2160 can be incorporated in a left prism, wherein the left prism is titled sideways relative to the longitudinal axis of the apparatus, by the same amount as the right prism. Thus, the right prism receives a right side view image of a three-dimensional object which is located at a side of the apparatus, while the left prism receives a left side view image of the three-dimensional.

It is noted that above optical structure provides a clear, straight and undistorted image at each of the right and left channels.

Figure 46A:
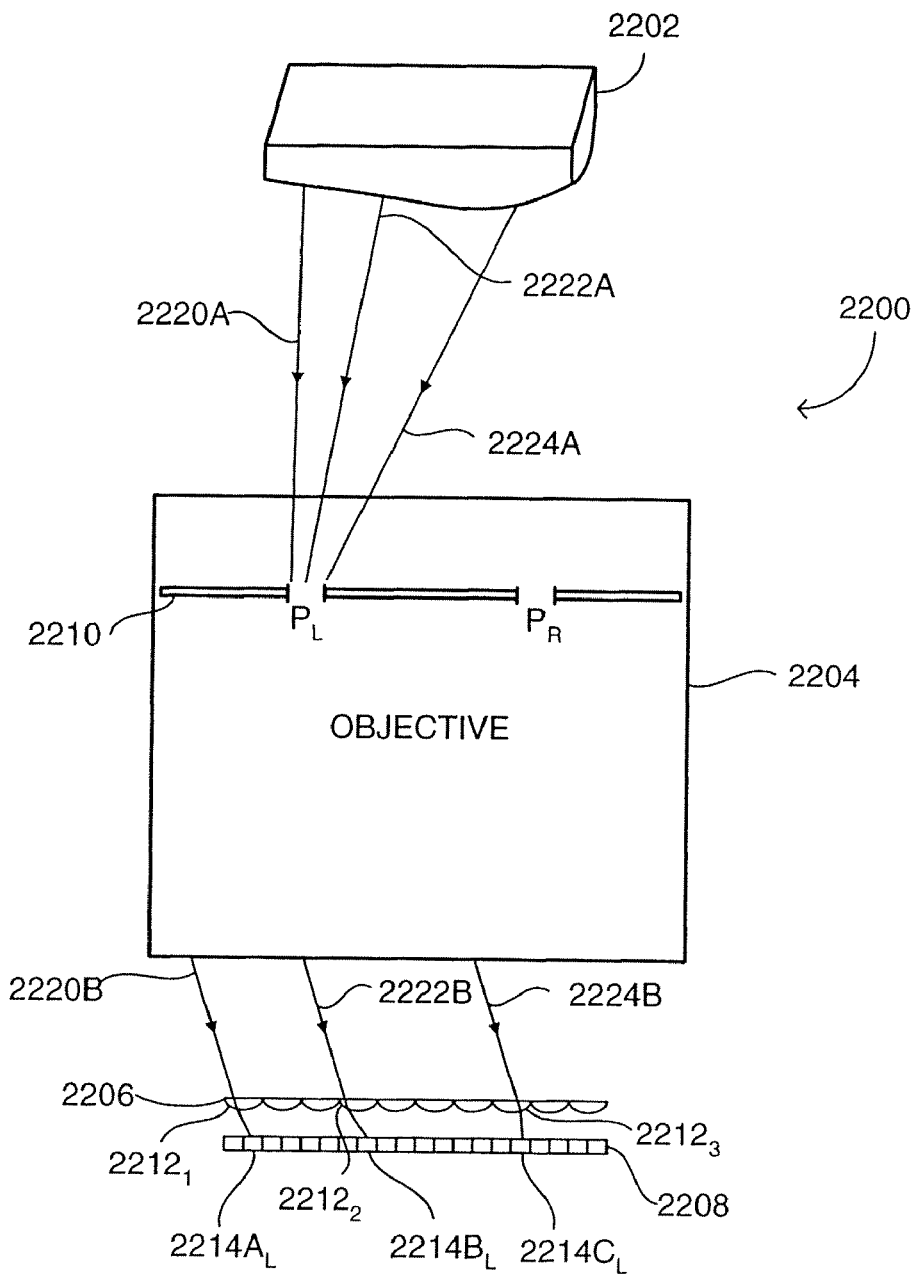
FIG. 46A is a schematic illustration of a physical object and a stereoscopic imaging apparatus, constructed and operative in accordance with a further embodiment of the disclosed technique.
Figure 46B:
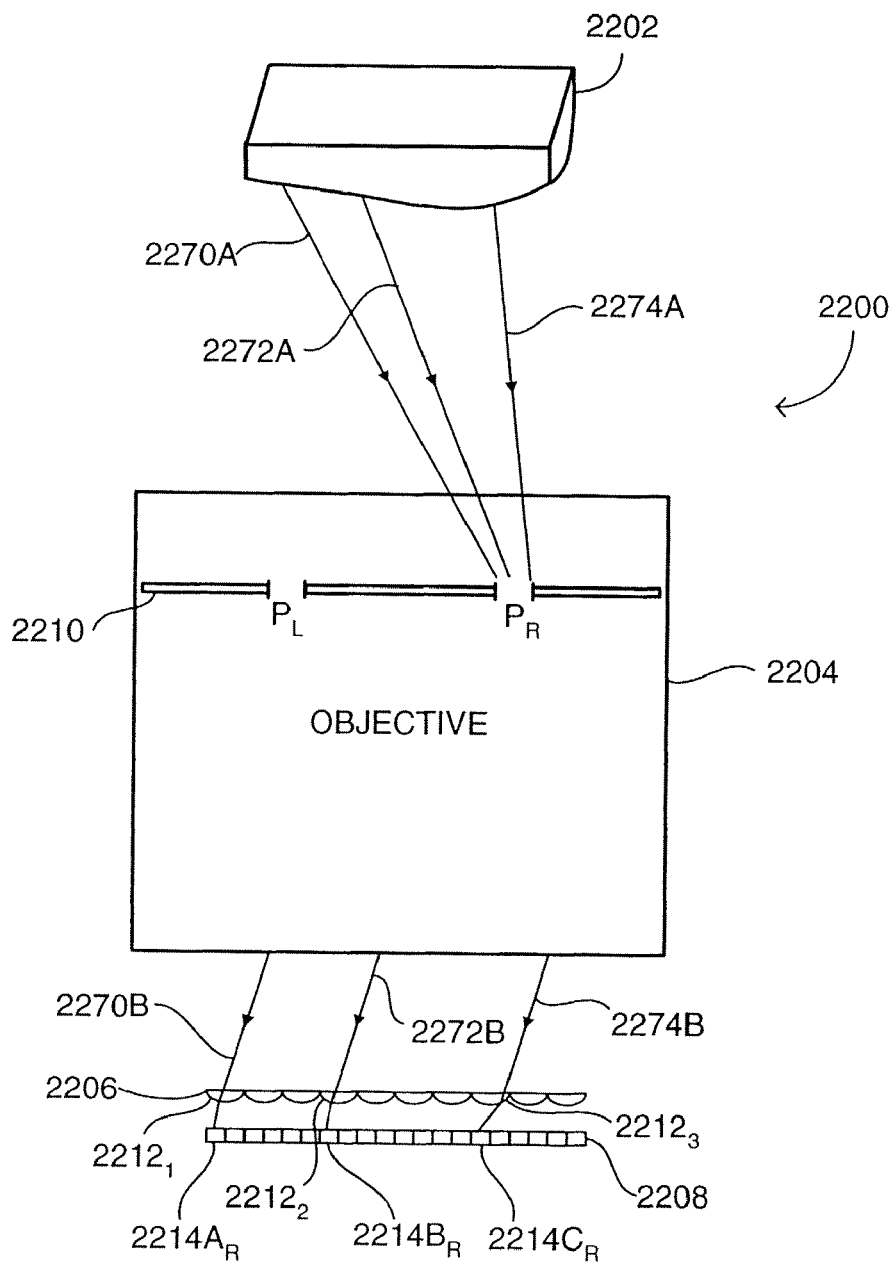
FIG. 46B is a schematic illustration of the apparatus of FIG. 46A, with a different set of light rays shown.

Reference is now made to FIG. 46A and FIG. 46B. FIG. 46A is a schematic illustration of a physical object 2202 and a stereoscopic imaging apparatus, generally referenced 2200, constructed and operative in accordance with a further embodiment of the disclosed technique. FIG. 46B is a schematic illustration of the apparatus of FIG. 46A, with a different set of light rays shown.

With reference to FIG. 46A, apparatus 2200 includes an objective lens assembly 2204, a lenticular lens layer 2206 and a light sensor array 2208. Lenticular lens layer 2206 and light sensor array 2208 are generally similar to lenticular lens layer 1106 and light sensor array 1108 of FIG. 28A. Objective lens assembly 2204 includes an aperture stop 2210, including a left pupil $P_L$ and a right pupil $P_R$. Aperture stop 2210 transmits light incident upon left pupil $P_L$ and a right pupil $P_R$, and substantially reflects or absorbs all other incident light.

Objective lens assembly 2204 generates two overlapping images on the image plane (i.e., on the plane defined by the light sensor array 2208). One of these images arrives from left pupil $P_L$ and the other image arrives from right pupil $P_R$. With reference to FIG. 46A, objective lens assembly 2204 receives light beams 2220A, 2222A and 2224A from physical object 2202, at left pupil $P_L$. Objective lens assembly 2204 emits light beams 2220A, 2222A and 2224A as light beams 2220B, 2222B and 2224B, respectively. Objective lens assembly 2204 directs light beams 2220B, 2222B and 2224B towards lenticular lenses $2212_1$, $2212_2$ and $2212_3$ of lenticular lens array 2206, respectively. Lenticular lenses $2212_1$, $2212_2$ and $2212_3$ direct light beams 2220B, 2222B and 2224B towards light sensors $2214A_L$, $2214B_L$ and $2214C_L$, respectively, in a similar manner as described in FIG. 28A.

Similarly, referring to FIG. 46B, objective lens assembly 2204 receives light beams 2270A, 2272A and 2274A from physical object 2202, at right pupil $P_R$. Light beams 2270A, 2272A and 2274A originate from the same points on physical object 2202 as light beams 2220A, 2222A and 2224A, respectively. Objective lens assembly 2204 emits light beams 2270A, 2272A and 2274A as light beams 2270B, 2272B and 2274B, respectively. Light beams 2270B, 2272B and 2274B are emitted at a substantially opposite direction, relative to an axis perpendicular to the image plane, from light beams 2220B, 2222B and 2224B (FIG. 46A). Light beams 2270B, 2272B and 2274B reach lenticular elements $2214A_R$, $2214B_R$ and $2214C_R$, respectively. Lenticular lenses $2212_1$, $2212_2$ and $2212_3$ direct light beams 2270B, 2272B and 2274B towards light sensors $2214A_R$, $2214B_R$ and $2214C_R$, respectively.

It is noted that in the present example, objective lens assembly 2204 is telecentric. Accordingly, light beams 2270B, 2272B and 2274B are parallel there between, as are light beams 2220B, 2222B and 2224B. Hence, each lenticular lens receives light beams at one of two specific directions, and directs these light beams to one of two specific light sensors. Alternatively, the objective lens assembly may be nearly telecentric, in which case these light beams are only approximately parallel, but the lenticular lens still separates between the two groups of light beams. In general, the objective lens assembly should direct the light beams from the left pupil in a direction from a first set of directions, and the light beams from the right pupil in a direction from a second set of directions.

According to the present embodiment, the pupils $P_L$ and $P_R$ define the "eyes" of the optical device, which are required for stereoscopic vision. It is noted that the light beams arrive at the lenticular elements substantially in one of two specific directions. Hence, each lenticular element distinguishes precisely between the light received from the left pupil and that received from the right pupil.

Figure 47:
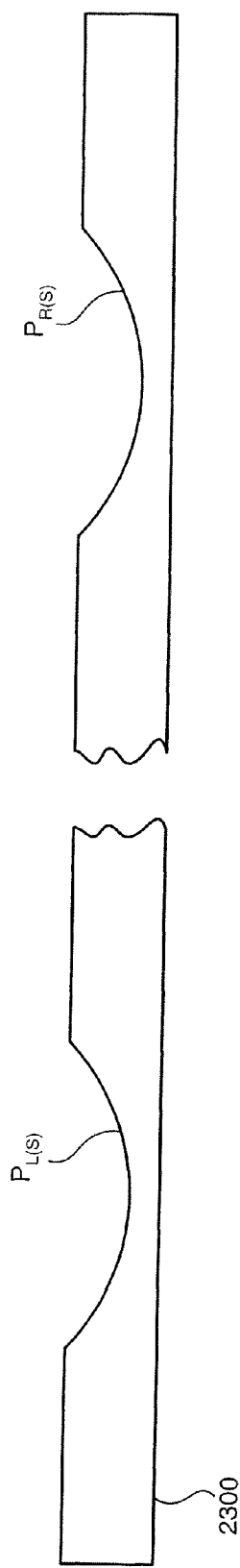
FIG. 47 is a schematic illustration of an aperture stop, constructed and operative in accordance with another embodiment of the disclosed technique.

Alternatively, the aperture stop includes "soft" pupils, instead of the pupils $P_L$ and $P_R$. Reference is now made to FIG. 47, which is a schematic illustration of an aperture stop, generally referenced 2300, constructed and operative in accordance with another embodiment of the disclosed technique. Aperture stop 2300 includes a left soft pupil $P_{L(S)}$ and a right soft pupil $P_{R(S)}$. Each of pupils $P_{L(S)}$ and $P_{R(S)}$ are in the form of a dent (instead of an aperture as in the case of ordinary "hard" pupils) in aperture stop 2300. Hence, the aperture stop is thinner at the soft pupils than at is at the rest of the plane, and therefore transmits more light at the pupils than at the rest of the plane. The light transmission through aperture stop 2300 is spatially variable, but not binary as in the case of "hard pupils".

Further alternatively, the left and right pupils may be "virtual pupils". Accordingly, the plane of aperture stop 2210 (FIG. 46A) transmits light there through at different locations thereon. The transmitted light reaches a lenticular lens array. Each lenticular lens receives light beams from various locations on the plane, and directs each of these light beams accordingly towards a light sensor array. However, only those light beams which are incident from two specific locations on the plane, namely, the left virtual pupil and the right virtual pupil, are taken into account in forming the stereoscopic image. For example, some of the light sensors, which receive light beams incident from other locations on the plane, may be removed, replaced, or ignored. Furthermore, the light sensors may be given different weights according to the certainty as to the location on the plane of the respective incident light beams.

It will be appreciated by persons skilled in the art that the disclosed technique is not limited to what has been particularly shown and described here in above. Rather the scope of the disclosed technique is defined only by the claims which follow.

The invention claimed is:

1. Stereoscopic device, comprising:
   an image directing assembly, having a first light inlet for receiving a first image and a second light inlet for receiving a second image, said first light inlet being spaced apart from said second light inlet;
   an image differentiator, differentiating between said first image and said second image, said image differentiator having a first state and a second state;
   an image detector,
   wherein said image directing assembly directs said first image to said image detector via a common path,
   wherein said image directing assembly directs said second image to said image detector via said common path;
   an optical assembly located in front of said image detector; and
   a controller coupled with said image detector and with said image differentiator, said controller controlling the state of said image differentiator, said controller enabling said image detector to detect said first image when said image differentiator is in said first state and said controller enabling said image detector to detect said second image when said image differentiator is in said second state.

2. The stereoscopic device according to claim 1, wherein said image differentiator is a partially-transparent rotating disk located where said first image and said second image are two distinct images, in front of said common path,
   wherein said partially-transparent rotating disk has a transparent portion and an opaque portion,
   wherein said partially-transparent rotating disk admits said first image through said transparent portion when said partially-transparent rotating disk rotates to a first position, corresponding to said first state of said image differentiator, and said partially-transparent rotating disk admits said second image through said transparent portion when said partially-transparent rotating disk rotates to a second position,
   corresponding to said second state of said image differentiator.

3. The stereoscopic device according to claim 2, further comprising an illuminator which emits light at a predetermined illuminating wavelength.

4. The stereoscopic device according to claim 3, wherein said predetermined illuminating wavelength is selected from the list consisting of:
   substantially visible red color light;
   substantially visible green color light;
   substantially visible blue color light;
   substantially visible cyan color light;
   substantially visible yellow color light;
   substantially visible magenta color light;
   substantially infra-red light;
   substantially ultra-violet light; and
   visible light.

5. The stereoscopic device according to claim 2, further comprising an illuminator which sequentially emits light at different predetermined illuminating wavelengths, said illuminator coupled with said controller,
   wherein said controller controls the operation of said illuminator,
   wherein said controller enables said image detector to detect said first image at each one of said different predetermined illuminating wavelengths, and said second image at each one of said different predetermined illuminating wavelengths, according to the angular position of said partially-transparent rotating disk and according to the state of said illuminator.

6. The stereoscopic device according to claim 5, wherein each of said different predetermined illuminating wavelengths is selected from the list consisting of:
   substantially visible red color light;
   substantially visible green color light;
   substantially visible blue color light;
   substantially visible cyan color light;
   substantially visible yellow color light;
   substantially visible magenta color light;
   substantially infra-red light;
   substantially ultra-violet light; and
   visible light.

7. The stereoscopic device according to claim 1,
wherein said image differentiator is a multi-wavelength rotating disk located where said first image and said second image are two distinct images, in front of said common path, said multi-wavelength rotating disk comprises a plurality of filtering sectors,
wherein each of said filtering sectors admits light in a different predetermined range of filter wavelengths, each angular position of said multi-wavelength rotating disk corresponding to a selected one of said first state and said second state of said image differentiator, and
wherein said controller enables said image detector to detect said first image and said second image at each one of said different predetermined ranges of filter wavelengths, according to the angular position of said multi-wavelength rotating disk.

8. The stereoscopic device according to claim 7, wherein said multi-wavelength rotating disk further comprises at least one opaque sector.

9. The stereoscopic device according to claim 7, further comprising an illuminator.

10. The stereoscopic device according to claim 1, wherein said image differentiator is located where said first image and said second image are two distinct images, in front of said common path,
wherein said image differentiator is a multiple aperture having a first aperture and a second aperture,
wherein an opening of said first aperture corresponds to said first state of said image differentiator and an opening of said second aperture corresponds to said second state of said image differentiator,
wherein said controller alternately controls the opening of said first aperture and said second aperture,
to control the state of said image differentiator.

11. The stereoscopic device according to claim 10, further comprising an illuminator which sequentially emits light at different predetermined illuminating wavelengths, wherein said controller enables said image detector to detect images, corresponding to a predetermined combination of an open state of a selected aperture of said multiple aperture and a selected one of said different predetermined illuminating wavelengths.

12. The stereoscopic device according to claim 1, wherein said controller is further coupled with said image differentiator, said image differentiator comprising:
a first polarizer located in the path of said first image, before said common path;
a second polarizer located in the path of said second image, before said common path; and
a third polarizer located in front of said image detector,
wherein similar polarization angle of said first polarizer and said third polarizer corresponds to said first state of said image differentiator, and similar polarization angle of said second polarizer and said third polarizer corresponds to said second state of said image differentiator,
wherein said controller controls the polarization angle of at least one of said first polarizer, said second polarizer and said third polarizer, to control the state of said image differentiator.

13. The stereoscopic device according to claim 12, wherein said first polarizer and said second polarizer are static and said third polarizer is dynamic.

14. The stereoscopic device according to claim 12, wherein said first polarizer and said second polarizer are dynamic and said third polarizer is static.

15. The stereoscopic device according to claim 12, wherein said first polarizer and said second polarizer are located on a rotating disk.

16. The stereoscopic device according to claim 12, wherein said image differentiator further comprises at least one polarization rotating cell.

17. The stereoscopic device according to claim 1, wherein said image differentiator is a lenticular lens layer, including a plurality of lenticular elements, located in front of said image detector,
wherein said lenticular elements enable said lenticular lens layer to differentiate between said first image and said second image,
wherein said lenticular lens layer directs said first image and said second image to said image detector, and
wherein said controller enables said image detector to detect said first image and said second image.

18. The stereoscopic device according to claim 1, wherein said image directing assembly further comprises:
a first mirror for receiving said first image;
a second mirror for receiving said second image;
a first center mirror for directing said first image from said first mirror to said common path; and
a second center mirror for directing said second image from said second mirror to said common path.

19. The stereoscopic device according to claim 1, said image directing assembly comprising:
a first parallelogramic prism for directing said first image to said common path; and
a second parallelogramic prism for directing said second image to said common path.

20. The stereoscopic device according to claim 19, further comprising:
a rail; and
a hinge sliding in said rail,
wherein said first parallelogramic prism and said second parallelogramic prism are coupled with said hinge,
wherein said first parallelogramic prism and said second parallelogramic prism move from a retracted position to an extended position, by rotating about said hinge when said hinge moves within said rail.

21. The stereoscopic device according to claim 1, said image directing assembly comprising:
a first fiberscope located between said first light inlet and said common path, said first fiberscope having a first light outlet; and
a second fiberscope located between said second light inlet and said common path, said second fiberscope having a second light outlet,
wherein said first fiberscope directs said first image from said first light inlet to said first light outlet,
wherein said second fiberscope directs said second image from said second light inlet to said second light outlet.

22. The stereoscopic device according to claim 1, said image directing assembly comprising:
a plurality of split fibers located between said first light inlet, said second light inlet and said common path, said split fibers having a light outlet, each said split fibers having a first arm, a second arm and a common arm,
wherein said first arms direct said first image from said first light inlet to said common path via said light outlet,
wherein said second arms direct said second image from said second light inlet to said common path via said light outlet.

23. The stereoscopic device according to claim 1, wherein said image detector comprises:
a one-dimensional light sensor array; and
a scanner,
wherein said scanner scans an object and directs a plurality of lines of an image of said object to said one-dimensional light sensor array,
wherein said controller is further coupled with said scanner, and wherein said controller enables said one-dimensional light sensor array to detect each of said lines, according to the angular position of said scanner.

24. The stereoscopic device according to claim 1, wherein said image detector comprises:
- a two-dimensional light sensor array; and
- a scanner,
- wherein said scanner scans an object and directs a plurality of two-dimensional images of said object to said two-dimensional light sensor array,
- wherein said controller is further coupled with said scanner,
- wherein said controller controls the operation of said two-dimensional light sensor array in a time delay integration mode, and
- wherein said controller enables said two-dimensional light sensor array to detect said two-dimensional images, according to the angular position of said scanner.

* * * * *

UNITED STATES PATENT AND TRADEMARK OFFICE
CERTIFICATE OF CORRECTION

PATENT NO. : 8,212,858 B2
APPLICATION NO. : 11/932417
DATED : July 3, 2012
INVENTOR(S) : Schechterman et al.

It is certified that error appears in the above-identified patent and that said Letters Patent is hereby corrected as shown below:

In the Specifications:

Col. 5, Line 56: "at least" should read --at at least--

Col. 5, Line 57: "at least" should read --at at least--

Signed and Sealed this
Fourth Day of June, 2013

Teresa Stanek Rea
*Acting Director of the United States Patent and Trademark Office*